(12) United States Patent
Kiel et al.

(10) Patent No.: US 6,303,316 B1
(45) Date of Patent: Oct. 16, 2001

(54) ORGANIC SEMICONDUCTOR RECOGNITION COMPLEX AND SYSTEM

(75) Inventors: Johnathan L. Kiel, Universal City; John G. Bruno, San Antonio; Jill E. Parker, Floresville; John L. Alls, San Antonio, all of TX (US); Charles R. Batishko, Richland, WA (US); Eric A. Holwitt, San Antonio, TX (US)

(73) Assignee: Conceptual Mind Works, Inc., San Antonio, TX (US)

( * ) Notice: Subject to any disclaimer, the term of this patent is extended or adjusted under 35 U.S.C. 154(b) by 0 days.

(21) Appl. No.: 09/608,706

(22) Filed: Jun. 30, 2000

Related U.S. Application Data

(60) Provisional application No. 60/199,620, filed on Apr. 25, 2000, and provisional application No. 60/142,301, filed on Jul. 2, 1999.

(51) Int. Cl.[7] .............................. C12Q 1/68; C12P 19/34; C07H 21/04
(52) U.S. Cl. .............................. 435/6; 435/7.1; 435/91.2; 436/94; 536/23.1
(58) Field of Search .............................. 435/6, 91.2, 7.1; 536/23.1; 436/94

(56) References Cited

U.S. PATENT DOCUMENTS

| | | | |
|---|---|---|---|
| 3,970,518 | 7/1976 | Giaever et al. | 435/239 |
| 4,230,685 | 10/1980 | Senyei et al. | 436/526 |
| 4,677,055 | 6/1987 | Dodin et al. | 435/7.32 |

(List continued on next page.)

FOREIGN PATENT DOCUMENTS

| | | | |
|---|---|---|---|
| WO91/19813 | 12/1991 | (WO) | C12Q/1/68 |
| WO96/40991 | 6/1996 | (WO) | C12Q/1/68 |
| WO99/31275 | 6/1999 | (WO) | C12Q/1/68 |

OTHER PUBLICATIONS

Bruno & Yu, "Immunomagnetic–electrochemiluminescent detection of *Bacillus anthracis* spores in soil matrices", *Appl. Environ. Microbio.*, 62:3474–76, 1996.

Bruno et al., "Preliminary electrochemiluminescence studies of metal ion–bacterial diazoluminomelanin (DALM) interactions", *J. Biolumin, Chemilum.*, 13:117–123, 1998.

Bruno, John G., "In vitro selection of DNA to chloroaromatics using magnetic microbead–based affinity separation and fluorescence detection", *Biochim. Biophys. Res. Comm.*, 234:117–120, 1997.

Bruno, John G., "A colorimetric inhibition study of single–stranded DNA decamer sequence interactions with dinitrotoluene", *Biochem. and Biophy Res. Comm.*, 236:344–346, 1997.

(List continued on next page.)

*Primary Examiner*—Kenneth R. Horlick
(74) *Attorney, Agent, or Firm*—Blakely, Sokoloff, Taylor & Zafman

(57) ABSTRACT

In a recognition complex system, nucleic acid ligands comprising random DNA sequences are operatively coupled to an organic semiconductor and distributed so as to form an array of recognition complexes. When an unknown chemical or biological analyte is applied to the array, the electrical and/or photochemical properties of one or more of the recognition complexes are altered upon binding of the nucleic acid ligand to the analyte. The degree to which the electrical and/or photochemical properties change is a function of the affinity of the nucleic acid ligand sequence for the analyte. The electrical and photochemical changes associated with the array, as a whole, can be used as a unique signature to identify the analyte. In certain embodiments, an iterative process of selection and amplification of nucleic acid ligands that bind to the analyte can be used to generate a new array with greater affinity and specificity for a target analyte, or to produce one or more nucleic acid ligands with high binding affinity for an analyte. The present invention also provides methods for preparing nucleic acid ligands that bind with high affinity to an analyte and using such nucleic acid ligands to neutralize the analyte.

62 Claims, 15 Drawing Sheets

U.S. PATENT DOCUMENTS

Figure 1:
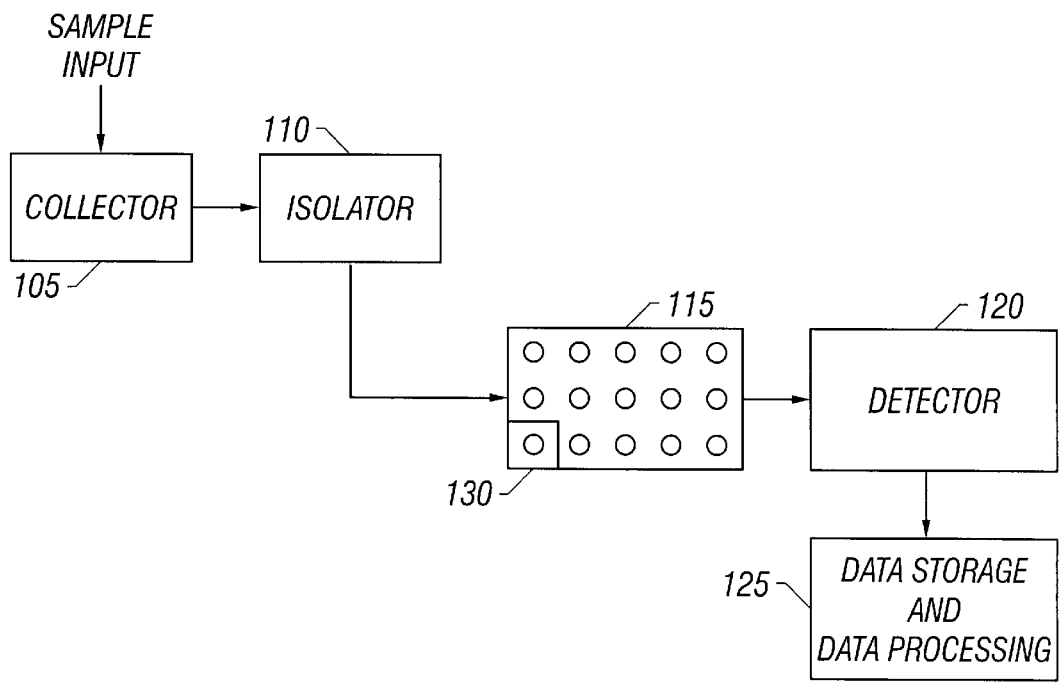

| | | | |
|---|---|---|---|
| 4,695,393 | 9/1987 | Chagnon et al. | 252/62.54 |
| 4,777,019 * | 10/1988 | Dandekar | 422/68 |
| 5,003,050 | 3/1991 | Kiel et al. | 534/573 |
| 5,156,971 | 10/1992 | Kiel et al. | 435/252.31 |
| 5,270,163 | 12/1993 | Gold et al. | 435/436 |
| 5,376,963 | 12/1994 | Zortea | 348/222 |
| 5,424,545 | 6/1995 | Block et al. | 250/343 |
| 5,446,543 | 8/1995 | Nakagawa et al. | 356/405 |
| 5,464,768 | 11/1995 | Kiel et al. | 435/240.2 |
| 5,475,096 | 12/1995 | Gold et al. | 536/23.1 |
| 5,567,588 | 10/1996 | Gold et al. | 435/436 |
| 5,578,832 | 11/1996 | Trulson et al. | 250/458.1 |
| 5,580,737 | 12/1996 | Polisky et al. | 435/436 |
| 5,582,981 | 12/1996 | Toole et al. | 435/436 |
| 5,595,877 | 1/1997 | Gold et al. | 435/436 |
| 5,632,957 | 5/1997 | Heller et al. | 422/68.1 |
| 5,637,459 | 6/1997 | Burke et al. | 435/436 |
| 5,641,629 | 6/1997 | Pitner et al. | 435/436 |
| 5,650,275 | 7/1997 | Pitner et al. | 435/436 |
| 5,658,673 | 8/1997 | Holwitt et al. | 428/423.1 |
| 5,670,637 | 9/1997 | Gold et al. | 536/22.1 |
| 5,683,867 | 11/1997 | Biesecker et al. | 435/436 |
| 5,696,249 | 12/1997 | Gold et al. | 536/23.1 |
| 5,707,796 | 1/1998 | Gold et al. | 435/436 |
| 5,712,375 | 1/1998 | Jensen et al. | 530/412 |
| 5,763,177 | 6/1998 | Gold et al. | 435/436 |
| 5,789,157 | 8/1998 | Jensen et al. | 435/436 |
| 5,817,785 | 10/1998 | Gold et al. | 536/23.1 |
| 5,818,044 | 10/1998 | Sodickson et al. | 250/339.06 |
| 5,837,832 | 11/1998 | Chee et al. | 536/22.1 |
| 5,837,860 | 11/1998 | Anderson et al. | 536/25.3 |
| 5,843,653 | 12/1998 | Gold et al. | 435/436 |
| 5,853,984 | 12/1998 | Davis et al. | 435/436 |
| 5,856,108 | 1/1999 | Kiel et al. | 435/7.32 |
| 5,861,242 | 1/1999 | Chee et al. | 435/5 |
| 5,861,254 | 1/1999 | Schneider et al. | 435/436 |
| 5,864,026 | 1/1999 | Jensen et al. | 536/23.1 |
| 5,867,265 | 2/1999 | Thomas | 356/328 |
| 5,874,218 | 2/1999 | Drolet et al. | 435/436 |
| 5,902,728 | 5/1999 | Parker et al. | 435/437 |
| 5,958,691 | 9/1999 | Pieken et al. | 435/436 |
| 5,972,721 | 10/1999 | Bruno et al. | 435/526 |
| 5,989,823 | 11/1999 | Jayasena et al. | 435/436 |
| 5,990,479 * | 11/1999 | Weiss et al. | 250/307 |
| 6,001,577 | 12/1999 | Gold et al. | 435/436 |
| 6,013,520 | 1/2000 | Parker et al. | 435/354 |
| 6,028,311 | 2/2000 | Sodickson et al. | 250/343 |
| 6,030,776 | 2/2000 | Eaton et al. | 435/436 |
| 6,043,909 | 3/2000 | Holub | 358/504 |
| 6,072,464 | 6/2000 | Ozeki | 345/154 |

OTHER PUBLICATIONS

Bruno, John G., "Broad applications of electrochemiluminescence technology to the detection and quantitation of microbiological, biochemical and chemical analytes", *Recent Res. Devel. in Microbiology,* 1:25–46, 1997.

Famulok and Mayer, "Aptamers as Tools in Molecular Biology and Immunology", *Curr. Topics in Microb. and Immun.,* 243:123–136, 1999.

Jayasena, S.D., "Aptamers: An Emerging Class of Molecules That Rival Antibodies in Diagnostics", *Clin. Chem.,* 34:1628–1650, 1999.

Kiel, Johnathan et al., "Diazoluminomelanin: A Synthetic Electron and Nonradiative Transfer Biopolymer", Proceedings of the 1989 International Symposium on Charge and Field Effects in Biosystems–2. Held Jun 4–9, 1989 in Richmond, Virginia, pp. 293–300, M.J. Allen et al., Editors.

Yu and Bruno, "Immunomagnetic–electrochemi–luminescent detection of *Escherichia coli* 0157 and *Salmonella typhimurium* in foods and environmental water samples", *Appl. Environ. Microbiol.,* 62:587–92, 1996.

Bruno & Yu, "Immunomagnetic–electrochemiluminescent detection of *Bacillus anthracis* Spores in Soil Matrices", *Appl. and Environ. Microb.,* 62(9):3474–3476, 1996.

Drolet, D.W. et al., A high throughput platform for systematic evolution of ligands exponential enrichment (SELEX), *Comb. Chem. High Throughput Screen,* Oct. 2(5):271–278, 1999.

Ellington & Szostak, "In vitro selection of RNA molecules that bind specific ligands", *Nature,* 346:818–822, 1990.

Ellington & Szostak, "Selection in vitro of single straded DNA molecules that fold into specific ligand–binding structures", *Nature,* 355:850–52, 1992.

Kiel, J.L. et al., "Diazoluminomelanin: a synthetic electron and nonradiative transfer biopolymer", In *Charge and Field Effects in Biosystems–2,* J.J. Allen, S.F. Cleary, F.M. Hawkridge, editors; Plenum Press, New York, 1989.

Kiel, J.L. et al., "Diazoluminomelanin: a synthetic luminescent biopolymer", *Free Radic. Res. Commun.,* 8(2):115–21, 1990.

Klug and Famulok, "All you wanted to know about SELEX", *Mol. Biol. Reports,* 20:97–107, 1994.

Kugler et al., "Photoelectron spectroscopy and quantum chemical modeling applied to polymer surfaces and interfaces in light–emitting devices", *Accounts of Chemical Research,* 32:225–234, 1999.

Tuerk, "In vitro evolution of functional nucleic acids: high–affinity RNA ligands of HIV–1 proteins", *Gene* 137:33–39, 1993.

Tuerk, "Using the SELEX combinatorial chemistry process to find high affinity nucleic acid ligands to target molecules", *Meth. Mol. Biol.* 67:219–30, 1997.

Gatto–Menking et al., "Sensitive detection of biotoxoids and bacterial spores using an immunomagnetic electrochemiluminescence sensor", *Biosensors & Bioelectronics,* 10:501–507, 1995.

Hacia et al., "Detection of heterozygous mutations in BRCA1 using high density oligonucleotide arrays and two–olour fluorescence analysis", *Nature Genetics,* 14:441–447, 1996.

Brody, E.N. et al., "The use of Aptamers in large arrays for molecular diagnostics", *Mol. Diagn.,* Dec., 4(4):381–388, 1999.

Lorsch and Szostak, "In vitro selection of nucleic acid sequences that bind small molecules." In: *Combinatorial Libraries: Synthesis Screening and Application Potential* (R. Cortese, ed.), Walter de Gruyter Publishing Co., New York, pp. 69–86, 1996.

Shoemaker et al., "Quantitative phenotypic analysis of yeast deletion mutants using ahighly parallel molecular bar–coding strategy", *Nature Genetics,* 14:450–456, 1996.

Tuerk, C. and Gold, L., "Systematic evolution of ligands by exponential enrichment: RNA ligands to bacteriophage T4 DNA Polymerase", *Science,* 249:505–510, 1990.

Yu and Bruno, "Immunomagnetic–electrochemiluminescent detection of *Escheria coli* O157 and *Salmonella typhimurium* in Foods and Environmental Water Samples", *App. and Environ. Microbiology,* 62(2):587–592, 1996.

\* cited by examiner

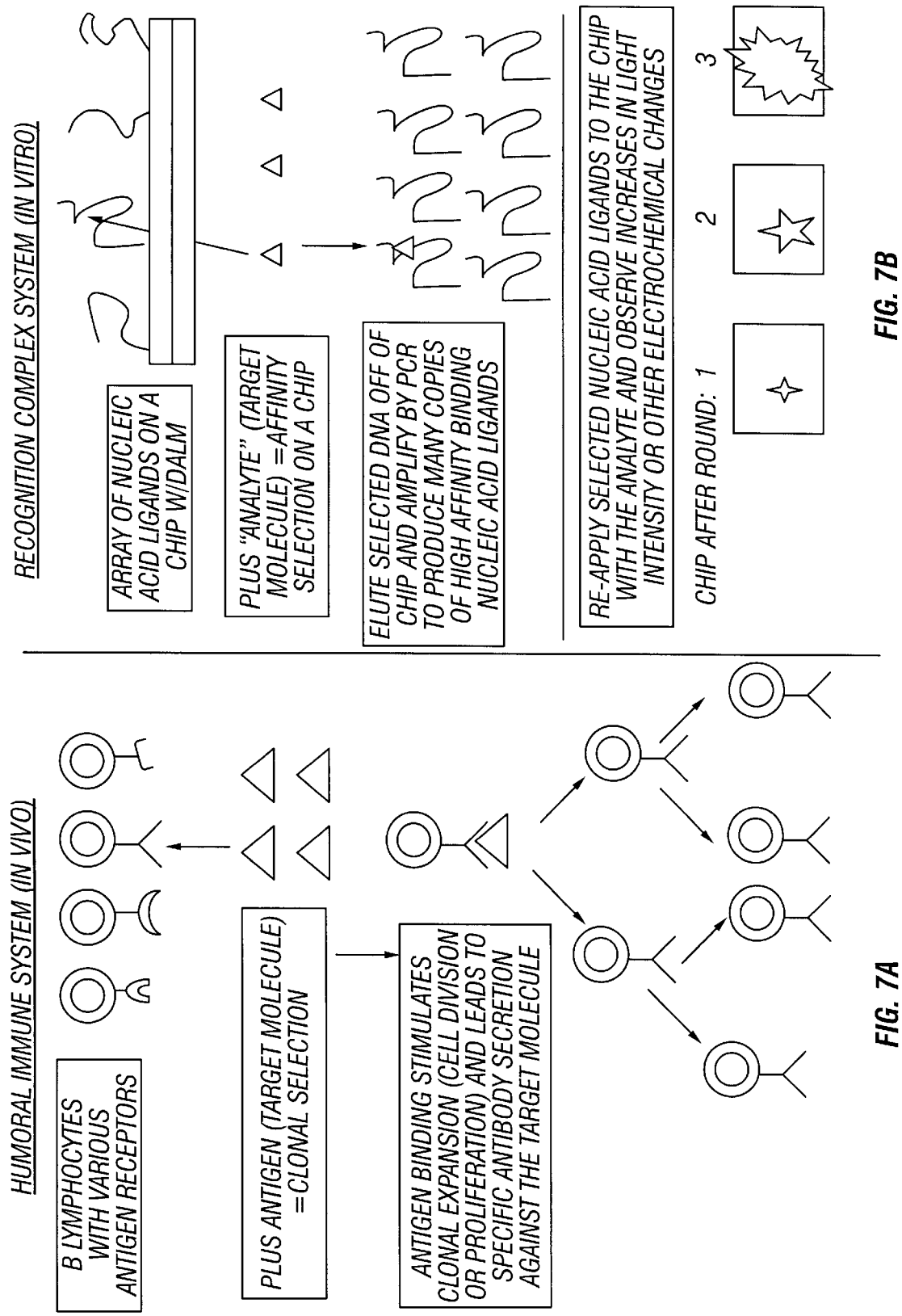

PCR PRODUCTS
FOLLOWING
SELEX ROUND:    1    2    3

PCR REACTANTS:

5'-AAAAAAAA-[RANDOM 40mer REGION]-TTTTTTTTT-3' (TEMPLATE)

-AAAAAAAAAA-5'-BIOTIN OR AMINO GROUP (PRIMER)

"MIRROR IMAGE" PRODUCTS:

5'-AAAAAAAA-[RANDOM 40mer REGION]-TTTTTTTTT-3' (TEMPLATE)

3'-TTTTTTTTT-[RANDOM 40mer REGION]-AAAAAAAAAA-5'-BIOTIN OR AMINO GROUP (NASCENT STRAND)

FIG. 13

CONTROL SPORE

HPM EXPOSED WITH DALM

ORGANIC SEMICONDUCTOR RECOGNITION COMPLEX AND SYSTEM

CROSS REFERENCE TO RELATED APPLICATIONS

This application claims the benefit under 35 U.S.C. §119 (e) of provisional Patent Application Serial Nos. 60/142,301, filed Jul. 2, 1999, and 60/199,620, filed Apr. 25, 2000. The invention described herein was made with Government support under contracts F41622-96-D-008 and F41824-00-D-700 awarded by the Department of the Air Force and Department of Energy contract number DE-AC06-76RL01830. The Federal Government has a nonexclusive, nontransferable, irrevocable, paid-up license to practice or have practiced for or on behalf of the United States the subject invention.

BACKGROUND OF THE INVENTION

1. Field of the Invention

The present invention relates to the field of detection and identification of analytes, using novel compositions and apparatus comprising one or more nucleic acid ligands operably coupled to an organic semiconductor. More particularly the present invention relates to methods of use of organic semiconductor chip technology, flow cell technology or magnetic filter separation technology, along with compositions comprising nucleic acid ligands, to identify analytes. The present invention further relates to the detection, identification and neutralization of chemical and biological warfare agents.

2. Description of Related Art

There is a great need for the development of methods and apparatus capable of detecting and identifying unknown chemical and biological agents (herein referred to as analytes), which include but are not limited to nucleic acids, proteins, illicit drugs, explosives, toxins, pharmaceuticals, carcinogens, poisons, allergens and infectious agents. Possible approaches to this problem include the use of nucleic acid microchip technology or magnetic bead technology. Although these technologies are known for various applications (e.g., Hacia et al, 1996; Shoemaker et al., 1996; U.S. Pat. Nos. 3,970,518; 4,230,685; 4,677,055; 4,695,393; 5,861,242; 5,578,832), the present invention provides a novel and unexpected use of these technologies to detect and identify unknown analytes.

As one skilled in the art will readily appreciate, any method, technique or device capable of such detection and identification would have numerous medical, industrial and military applications. For instance, such methods, techniques and devices could be employed in the diagnosis and treatment of disease, to develop new compounds for pharmaceutical, medical or industrial purposes, or to identify chemical and biological warfare agents.

Current methods, techniques and devices that have been applied to identification of chemical and biological analytes typically involve capturing the analyte through the use of a non-specific solid surface or through capture deoxyribonucleic acids (DNA) or antibodies. A number of known binding agents must then be applied, particularly in the case of biological analytes, until a binding agent with a high degree of affinity for the analyte is identified. A labeled antiligand (e.g., labeled DNA or labeled antibodies) must be applied, where the antiligand causes, for example, the color or fluorescence of the analyte to change if the binding agent exhibits affinity for the analyte (i.e., the binding agent binds with the analyte). The analyte may be identified by studying which of the various binding agents exhibited the greatest degree of affinity for the analyte.

There are a number of problems associated with current methods of chemical and biological agent identification. It takes a great deal of time and effort to repetitiously apply each of the known labeled antiligands, until an antiligand exhibiting a high degree of affinity is found. Accordingly, these techniques are not conducive to easy automation. Current methods are also not sufficiently robust to work in the heat, dust, humidity or other environmental conditions that might be encountered, for example, on a battlefield or in a food processing plant. Portability and ease of use are also problems seen with current methods for chemical and biological agent identification.

SUMMARY OF THE INVENTION

The present invention fulfills an unresolved need in the art, by providing a recognition complex and a recognition complex system that are capable of identifying an unknown chemical or biological agent (hereafter, "analyte") and, if desired, identifying and amplifying a neutralizing agent capable of inactivating or destroying the analyte. The recognition complex and recognition complex system and the corresponding techniques should be capable of full automation.

In one embodiment, the recognition complex system of the present invention employs organic semiconductor chip technology, wherein nucleic acid ligands are distributed across the surface of the chip so as to form an array of recognition complexes, each recognition complex comprised of a nucleic acid ligand attached to an organic semiconductor. In a preferred embodiment, the organic semiconductor is DALM (diazoluminomelanin), although the use of other organic semiconductors, such as polyphenylenes, is contemplated within the scope of the invention. For certain applications, the recognition complexes may be positioned between a pair of electrodes. Binding of analyte to a recognition complex may be detected by changes in the electrical or photochemical properties of the nucleic acid ligand/organic semiconductor couplet upon binding to the analyte. The degree to which the electrical and photochemical properties change is a function of the degree to which the nucleic acid ligand binds the analyte. Accordingly, the electrical and photochemical changes that occur across all of the recognition complexes, when taken as a whole, can be used as a unique signature to identify the analyte.

In certain embodiments, the analyte to be identified may be added to the array in the form of a complex mixture that may include, for example, aqueous or organic solvent, proteins, lipids, nucleic acids, detergents, particulates, intact cells, bacteria, viruses and spores, as well as other components. In other embodiments, the analyte may be partially or fully purified before exposure to the array.

In another embodiment, the nucleic acid ligand sequences that bind to the analyte may be isolated, amplified (e.g., using a polymerase chain reaction) and redistributed across a clean chip surface and attached to the organic semiconductor to form a new array. The nucleic acid ligand sequences that do not bind to the analyte may be discarded. The new array is exposed to the analyte and binding of analyte to nucleic acid ligands produces an enhanced electrical and photochemical signature, as the nucleic acid ligand sequences present on the new array more specifically compliment the analyte. This procedure may be repeated, with each iteration producing a more unique or enhanced signature.

In a further embodiment, this iterative process may be used to identify and amplify one or more nucleic acid ligand sequences that exhibit the highest degree of affinity for the analyte. Production of a nucleic acid ligand that binds to the analyte with high affinity (dissociation constant of 1.0 $\mu$M or lower) would have utility in a variety of applications. For certain embodiments, production of a nucleic acid ligand with a dissociation constant of 10 nM or lower is preferred.

In another embodiment, nucleic acid ligands that bind to the analyte with high affinity can be reproduced (synthesized or amplified) for use as a neutralizing agent to inactivate or destroy the analyte. A high affinity nucleic acid ligand may be attached to a variety of agents that could be used to neutralize the analyte. In certain embodiments, the high affinity nucleic acid ligand can be attached to an organic semiconductor, such as DALM. The DALM/nucleic acid ligand couplet, after binding to the analyte, may be activated by a variety of techniques, including exposure to sunlight, heat, or irradiation of various types, including laser, microwave, radiofrequency, ultraviolet and infrared. Activation of the DALM/nucleic acid ligand couplet results in absorption of energy, which may be transmitted to the analyte, inactivating or destroying it. It is contemplated within the scope of the invention that the nucleic acid ligand could be attached to other agents that would inactivate the analyte, such as toxic proteins, enzymes capable of activating protoxins, or other molecules or reactive moieties including organic or inorganic compounds.

In other embodiments, the high affinity nucleic acid ligand could be incorporated into an apparatus capable of being carried into the field, for example, by soldiers or vehicles entering a battlefield. As an example, the high affinity nucleic acid ligand could be incorporated into a patch or card to be worn by an individual. Exposure of the individual to the specific analyte for which the nucleic acid ligand exhibits high affinity could be indicated by a color change of the patch, or by a change in the electrical or photochemical properties of a nucleic acid ligand/organic semiconductor couplet. Alternatively, the high affinity nucleic acid ligand could be incorporated into an apparatus to be carried by a vehicle, that could be used to cover a wide area to detect and identify unknown chemical or biological agents. The skilled artisan will realize that the scope of the present invention is not limited to applications in chemical or biological warfare, but rather includes a broad variety of potential applications in industry and medicine, where early detection and identification of exposure to chemical or biological agents is desired.

In certain embodiments, the nucleic acid ligands are attached to magnetic beads instead of to a chip. An array of nucleic acid ligands may be assembled, each attached to a magnetic bead. In certain embodiments, each nucleic acid ligand attached to a single magnetic bead has the same nucleic acid sequence, while in other embodiments a single magnetic bead may be attached to nucleic acid ligands of different sequences. In a preferred embodiment, the magnetic bead is attached to an organic semiconductor, preferably DALM, and the nucleic acid ligand is attached to the organic semiconductor, forming an array of recognition complexes. Although any method may be employed within the scope of the present invention to attach the organic semiconductor to the magnetic bead and the nucleic acid ligand to the organic semiconductor, in a preferred embodiment the organic semiconductor is covalently attached to the magnetic bead and the nucleic acid ligand is attached to the organic semiconductor is non-covalently attached to the organic semiconductor. In a more preferred embodiment, the attachment of nucleic acid ligand to organic semiconductor is an electrostatic interaction, preferably mediated by magnesium ion.

In certain embodiments, an array of recognition complexes attached to magnetic beads is exposed to an analyte and binding of analyte to nucleic acid ligand may be detected, for example, by photochemical changes in the nucleic acid ligand/DALM couplet upon binding to the analyte. The skilled artisan will realize that magnetic beads would be particularly useful for separating recognition complexes that bind to the analyte from recognition complexes that do not bind the analyte. In one embodiment, a magnetic flow cell, such as is described in U.S. Pat. No. 5,972,721, the entire text of which is incorporated herein by reference, could be used in conjunction with the recognition complex system to identify and separate analyte-binding recognition complexes from recognition complexes that do not bind the analyte. In preferred embodiments, the recognition complexes attached to magnetic beads may be used in the same manner as discussed above for recognition complexes attached to chips, to identify an unknown analyte, to produce nucleic acid ligands with high affinity for a specific analyte, or to generate an array of nucleic acid complexes with increased affinity and/or specificity for a target analyte.

Figure 6:
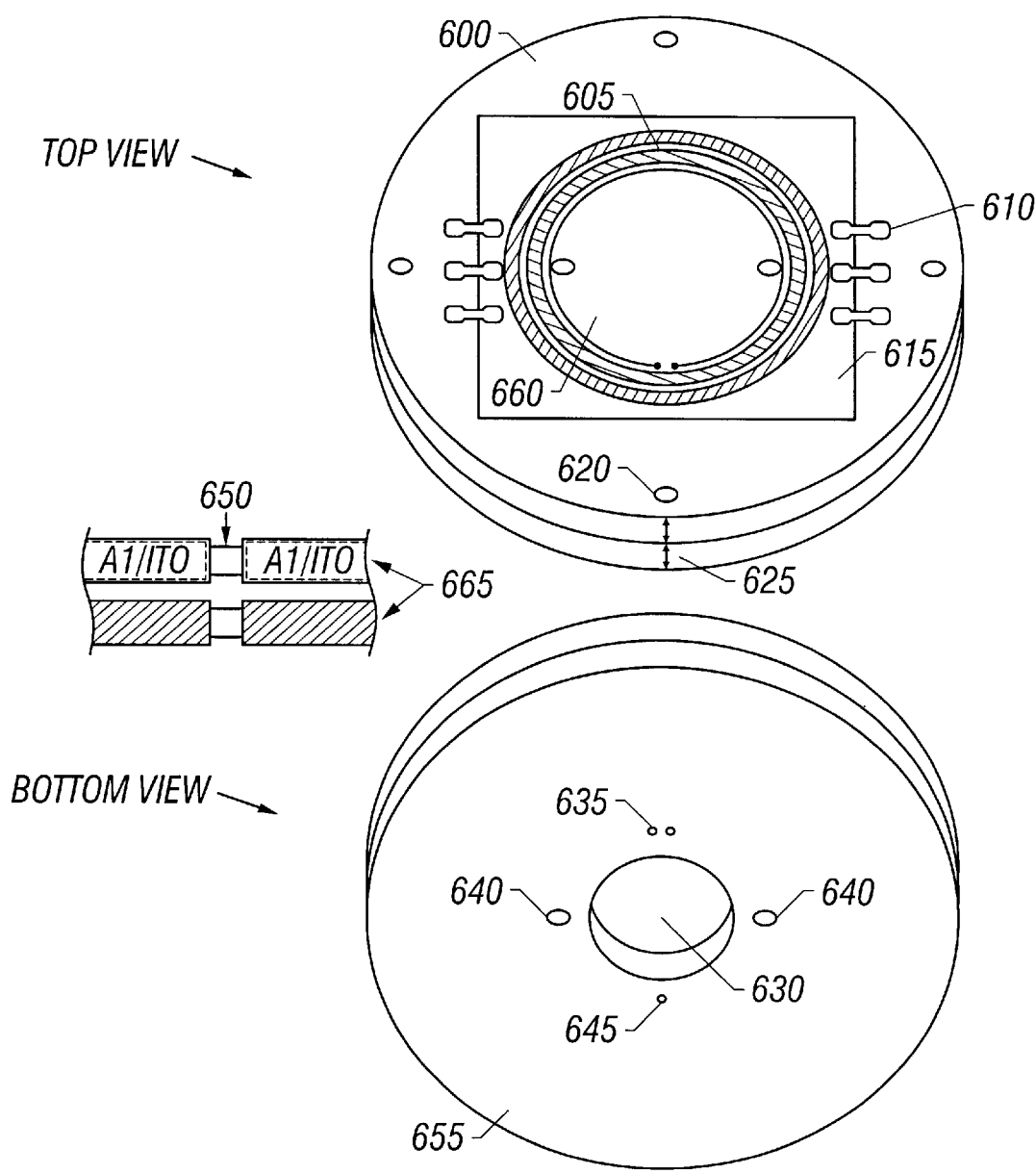

In other embodiments, the recognition complexes of the present invention may be used in a flow cell apparatus, for example, as illustrated in FIG. 6.

In preferred embodiments, the nucleic acid ligand is DNA, although it is contemplated within the scope of the invention that other nucleic acids comprised of RNA or synthetic nucleotide analogs could be utilized as well. In certain embodiments, the nucleic acid ligand sequences are random, or may be generated from libraries of random DNA sequences. In other embodiments, the nucleic acid ligand sequences may not be random, but may rather be designed to react with specific target analytes. In a preferred embodiment, the nucleic acid ligand sequences are aptamers (Lorsch and Szostak, 1996; Jayasena, 1999; U.S. Pat. Nos. 5,270,163; 5,567,588; 5,650,275; 5,670,637; 5,683,867; 5,696,249; 5,789,157; 5,843,653; 5,864,026; 5,989,823 and PCT application WO 99/31275, each incorporated herein by reference).

Certain embodiments of the present invention concern a recognition complex system that is capable of detecting and identifying unknown analytes. Other embodiments of the present invention concern a recognition complex system and methods of use of a recognition complex system that can detect and identify an unknown analyte in an automated, single binding step procedure. In preferred embodiments, the recognition complex system may be used in a method to detect explosives or illegal drugs in an airport detection system, to detect air-borne pathogens in an air conditioner monitoring system, to detect water-borne pathogens, carcinogens, teratogens or toxins in a water quality monitoring system, to detect pathogens in a hospital operating room monitoring system, to screen for pathogens in samples of human tissues or fluids, to detect allergens, pathogens or contaminants in a food production monitoring system, to detect genetically modified organisms, or to perform high through-put screening for pharmaceutical compounds.

Other embodiments of the present invention concenr a recognition complex system that is capable of producing information regarding specific chemical and biological properties of an unknown analyte.

Still other embodiments of the present invention concern a recognition complex system that is capable of producing nucleic acid ligands that bind with high affinity to target analytes. Such high affinity nucleic acid ligands may be used as neutralizing agents to counter adverse biological effects associated with an unknown analyte. High affinity nucleic acid ligands may also be incorporated into devices capable of detecting and identifying analytes under field conditions.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 illustrates a recognition complex system in accordance an exemplary embodiments of the present invention.

FIG. 2A illustrates an exemplary configuration for a recognition complex system, showing a direct current version of a recognition complex positioned between a first and a second electrode.

FIG. 2B illustrates another exemplary configuration for a recognition complex system, showing an alternating current version of a recognition complex positioned between a first and a second electrode.

FIG. 3 illustrates another exemplary embodiment of a recognition complex system, using recognition complexes attached to magnetic beads. The flow chart illustrates the operational relationships between the components of a preferred embodiment of a recognition complex system.

FIG. 4 illustrates a process for separation of recognition complexes, comprising magnetic beads, that bind analyte from those that do not, as well as an iterative process for producing nucleic acid ligands that bind to an analyte with high affinity.

FIG. 5 illustrates a process for viability testing.

FIG. 6 illustrates another exemplary embodiment of a recognition complex system, using flow cells.

FIG. 7 the similarities between the recognition complex system of the present invention and a biological immune system.

FIG. 8A illustrates the increasing specificity of nucleic acid ligands for analyte binding produced by the SELEX technique. The figure shows PCR products detected by gel electrophoresis after each round of SELEX.

FIG. 8B illustrates the increasing specificity of nucleic acid ligands for analyte binding produced by the SELEX technique. The figure shows ECL intensity after each round of SELEX.

FIG. 9A shows the emission spectra (260 nm excitation) of an empty polyacrylamide gel, random 60 mer DNA in a polyacrylamide gel or DALM.

FIG. 9B shows the emission spectra of DALM in the presence or absence of DNA at 360 nm excitation.

FIG. 10 shows a comparison of spatial fluorescence spectra for two different types of recognition complex systems (ligated array versus random 60 mers) before and after addition of various analytes. The DNA arrays were electrophoresed in 10% polyacrylamide gels and fluorescence scanning was performed using an excitation of 260 nm and emission wavelength of 420 nm. SEB Staphylococcal Enterotoxin B, BACA gene probes=*Bacillus anthracis* capsular antigen gene probes, and N6-20=a DNA ladder standard composed of small DNA fragments from 6 to 20 bp.

FIG. 11 shows the reproducibility of the fluorescence emission profile of a ligated nucleic acid ligand array in a polyacrylamide gel after addition of whole cholera toxin, in the presence and absence of DALM.

FIG. 12 illustrates a method employed for producing high affinity nucleic acid ligands against anthrax spores.

FIG. 13 illustrates a PCR method for amplifying selected nucleic acid ligands.

FIG. 14 illustrates ECL and calorimetric based anthrax spore detection using low DNA to spore ratio developed nucleic acid ligands.

FIG. 15 illustrates a method of neutralization using DALM and high affinity nucleic acid ligands against a target analyte.

FIG. 16 illustrates a process for destroying a target analyte using DALM irradiated with light or heat, for example.

FIG. 17 shows the photochemical transduction properties of DALM.

FIG. 18 shows the destruction of an anthrax spore using DALM and a high power microwave pulse.

FIG. 19 illustrates a CIE chromaticity approach to data analysis.

DESCRIPTION OF ILLUSTRATIVE EMBODIMENTS

Definitions

As used herein, "a" or "an" may mean one or more than one of an item.

"Nucleic acid" means either DNA, RNA, single-stranded, double-stranded or triple stranded and any chemical modifications thereof. Virtually any modification of the nucleic acid is contemplated by this invention. Non-limiting examples of nucleic acid modifications are discussed in further detail below. "Nucleic acid" encompasses, but is not limited to, oligonucleotides and polynucleotides. "Oligonucleotide" refers to at least one molecule of between about 3 and about 100 nucleotides in length. "Polynucleotide" refers to at least one molecule of greater than about 100 nucleotides in length. These terms generally refer to at least one single-stranded molecule, but in certain embodiments also encompass at least one additional strand that is partially, substantially or fully complementary in sequence. Thus, a nucleic acid may encompass at least one double-stranded molecule or at least one triple-stranded molecule that comprises one or more complementary strand(s) or "complement (s)." As used herein, a single stranded nucleic acid may be denoted by the prefix "ss", a double stranded nucleic acid by the prefix "ds", and a triple stranded nucleic acid by the prefix "ts."

Within the practice of the present invention, a "nucleic acid" may be of almost any length, from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 40, 45, 50, 55, 60, 65, 70, 75, 80, 85, 90, 95, 100, 110, 120, 130, 140, 150, 160, 175, 200, 225, 250, 275, 300, 400, 500, 600, 700, 800, 900, 1000, 1500, 2000, 2500, 3000, 3500, 4000, 4500, 5000, 6000, 7000, 8000, 9000, 10000, 15000, 20000 or even more bases in length.

The term "nucleic acid" will generally refer to at least one molecule or strand of DNA, RNA or a derivative or mimic thereof, comprising at least one nucleobase. A "nucleobase" refers to a heterocyclic base, for example, a purine or pyrimidine base naturally found in DNA (e.g. adenine "A," guanine "G," thymine "T" and cytosine "C") or RNA (e.g. A, G, uracil "U" and C), as well as their derivatives and mimics. A "derivative" refers to a chemically modified or altered form of a naturally occurring molecule, while "mimic" and "analog" refer to a molecule that may or may not structurally resemble a naturally occurring molecule, but that functions similarly to the naturally occurring molecule. One function of a nucleobase is to hydrogen bond to other nucleobases. Nucleobases can form one or more hydrogen bonds ("anneal" or "hybridize") with at least one naturally occurring nucleobase in manner that may substitute for naturally occurring nucleobase pairing (e.g. the hydrogen bonding between A and T, G and C, and A and U).

A nucleic acid may comprise, or be composed entirely of, at least one nucleobase, a nucleobase linker moiety and/or a backbone moiety. As used herein, a "moiety" generally refers to a smaller chemical or molecular component of a larger chemical or molecular structure, and is encompassed by the term "molecule."

A "nucleoside" is an individual chemical unit comprising a nucleobase covalently attached to a nucleobase linker moiety. An example of a "nucleobase linker moiety" is a sugar comprising 5-carbon atoms (a "5-carbon sugar"), including but not limited to deoxyribose, ribose or arabinose, and derivatives or mimics of 5-carbon sugars. Examples of derivatives or mimics of 5-carbon sugars include 2'-fluoro-2'-deoxyribose or carbocyclic sugars where a carbon is substituted for the oxygen atom in the sugar ring. By way of example, nucleosides comprising purine (i.e. A and G) or 7-deazapurine nucleobases are typically covalently attached at the 9 position of the purine or 7-deazapurine to the 1'-position of a 5-carbon sugar. In another example, nucleosides comprising pyrimidine nucleobases (i.e. C, T or U) are typically covalently attached at the 1 position of the pyrimidine to the 1'-position of a 5-carbon sugar (Kornberg and Baker, DNA Replication, 2nd Ed. (Freeman, San Francisco, 1992). However, other types of covalent attachments of a nucleobase to a nucleobase linker moiety are known in the art.

A "nucleotide" refers to a nucleoside further comprising a "backbone moiety" used for the covalent attachment of one or more nucleotides to another molecule or to each other to form a nucleic acid. The "backbone moiety" in naturally occurring nucleotides typically comprises a phosphorus moiety covalently attached to a 5-carbon sugar. The attachment of the backbone moiety typically occurs at either the 3'- or 5'-position of the 5-carbon sugar. However, other types of attachments are known in the art, particularly when the nucleotide comprises derivatives or mimics of a naturally occurring 5-carbon sugar or phosphorus moiety.

"Nucleic acid ligand" means a non-naturally occurring nucleic acid having a desirable action on a target. A desirable action includes, but is not limited to, binding of the target, catalytically changing the target, reacting with the target in a way that modifies or alters the target or the functional activity of the target, covalently attaching to the target, facilitating the reaction between the target and another molecule, and neutralizing the target. In a preferred embodiment, the action is specific binding affinity for a target molecule, such target molecule being a three dimensional chemical structure. The meaning of "nucleic acid ligand" specifically excludes nucleic acids that bind to another nucleic acid through a mechanism which predominantly depends on Watson/Crick base pairing. The meaning of "nucleic acid ligand" also excludes naturally occurring nucleic acids that have the known physiological function of being bound by the target molecule, such as, for example, binding of transcriptional factors to consensus DNA sequences. In another preferred embodiment, binding of a nucleic acid ligand to a target allows the neutralization of the target. Nucleic acid ligands include, but are not limited to, nucleic acids that are identified by the SELEX process discussed below.

"SELEX" (Systematic Evolution of Ligands by Exponential enrichment) involves the combination of selection of nucleic acid ligands which interact with a target in a desirable manner, for example binding to the target, with amplification of those selected nucleic acid ligands. Iterative cycling of the selection/amplification steps allows selection of one or a small number of nucleic acid ligands which interact most strongly with the target from a pool which contains a very large number of nucleic acid ligands. Cycling of the selection/amplification procedure is continued until a selected goal is achieved. In certain embodiments of the present invention, the goal may be to produce one or more nucleic acid ligands that, for example, can be used to neutralize or destroy a toxin, poison, allergen or biohazardous agent such as a virus, bacterium or spore. In other embodiments, the goal may be to produce one or more nucleic acid ligands that can be used to identify a target analyte.

"Aptamer" means a nucleic acid that binds to another molecule ("target," as defined below). This binding interaction does not encompass standard nucleic acid/nucleic acid hydrogen bond formation exemplified by Watson-Crick basepair formation (e.g., A binds to U or T and G binds to C), but encompasses all other types of non-covalent (or in some cases covalent) binding. Non-limiting examples of non-covalent binding include hydrogen bond formation, electrostatic interaction, Van der Waals interaction and hydrophobic interaction. An aptamer may bind to another molecule by any or all of these types of interaction, or in some cases by covalent interaction. Covalent binding of an aptamer to another molecule may occur where the aptamer or target molecule contains a chemically reactive or photoreactive moiety. The term "aptamer" or "specifically binding nucleic acid" refers to a nucleic acid that is capable of forming a complex with an intended target substance. "Target-specific" means that the aptamer binds to a target analyte with a much higher degree of affinity than it binds to contaminating materials.

"Analyte," "target" and "target analyte" mean any compound or aggregate of interest. Non-limiting examples of analytes include a protein, peptide, carbohydrate, polysaccharide, glycoprotein, lipid, hormone, receptor, antigen, allergen, antibody, substrate, metabolite, cofactor, inhibitor, drug, pharmaceutical, nutrient, toxin, poison, explosive, pesticide, chemical warfare agent, biohazardous agent, prion, radioisotope, vitamin, heterocyclic aromatic compound, carcinogen, mutagen, narcotic, amphetamine, barbiturate, hallucinogen, waste product, contaminant or other molecule. Molecules of any size can serve as targets. "Analytes" are not limited to single molecules, but may also comprise complex aggregates of molecules, such as a virus, bacterium, spore, mold, yeast, algae, amoebae, dinoflagellate, unicellular organism, pathogen or cell. In certain embodiments, cells exhibiting a particular characteristic or disease state, such as a cancer cell, may be target analytes. Virtually any chemical or biological effector would be a suitable target.

"Binding" refers to an interaction or binding between a target and a nucleic acid ligand or aptamer, resulting in a sufficiently stable complex so as to permit separation of nucleic acid ligand:target complexes from uncomplexed nucleic acid ligands under given binding or reaction conditions. Binding is mediated through hydrogen bonding or other molecular forces.

"Organic semiconductor" means a conjugated (alternating double and single bonded) organic compound in which regions of electrons and the absence of electrons (holes or positive charges) can move with varying degrees of difficulty through the aligned conjugated system (varying from insulator to conductor). An organic semiconductor may be thought of as the organic equivalent of a metal, in terms of electrical properties. Organic semiconductors are distinguished from metals in their spectroscopic properties. Organic semiconductors of use in the practice of the instant invention may be fluorescent, luminescent, chemiluminescent, sonochemiluminescent, thermochemiluminescent or electrochemiluminescent or may be otherwise characterized by their absorption, reflection or emission of electromagnetic radiation, including infrared, ultraviolet or visible light.

"Recognition complex" refers to a nucleic acid ligand that is operably coupled to an organic semiconductor. "Operably coupled" means that the nucleic acid ligand and the organic semiconductor are in close physical proximity to each other, such that binding of an analyte to the nucleic acid ligand results in a change in the properties of the organic semiconductor that is detectable as a signal. In preferred embodiments, the signal is an electrochemical signal, such as a photochemical signal, a fluorescent signal, a luminescent signal, a change of color or a change in electrical conductivity. In one preferred embodiment, the signal is a change in the fluorescence emission profile of the organic semiconductor/nucleic acid ligand couplet. Operable coupling may be accomplished by a variety of interactions, including but not limited non-covalent or covalent binding of the organic semiconductor to the nucleic acid ligand. In another embodiment, the nucleic acid ligand may be at least partially embedded in the organic semiconductor. Virtually any type of interaction between the organic semiconductor and the nucleic acid ligand is contemplated within the scope of the present invention, so long as the binding of an analyte to the nucleic acid ligand results in a change in the properties of the organic semiconductor. In one preferred embodiment, the nucleic acid ligand is electrostatically linked to the organic semiconductor by a magnesium ion bridge.

A "recognition complex system" comprises an array of recognition complexes. In preferred embodiments, the array of recognition complexes is operably coupled to a detection unit, such that changes in the electrochemical properties of the organic semiconductor that result from binding of analyte to nucleic acid ligand may be detected by the detection unit. It is contemplated within the scope of the present invention that detection may be an active process or a passive process. For example, in embodiments where the array of recognition complexes is incorporated into a card or badge, the binding of analyte may be detected by a change in color of the card or badge. In other embodiments, detection occurs by an active process, such as scanning the fluorescence emission profile of an array of recognition complexes.

"Electrochemical" is used in a broad sense to mean any process involving a transfer of electrons, including reduction-oxidation chemistry of any sort. "Electrochemical" specifically includes photo-induced oxidation and reduction.

"Photochemical" means any light related or light induced chemistry. A "photochemical signal" specifically includes, but is not limited to, a fluorescent signal, a luminescent signal, a change of color, a change in electrical conductivity, photo-oxidation and photo-reduction.

"Magnetic bead," "magnetic particle" and "magnetically responsive particle" are used herein to mean any particle dispersible or suspendable in aqueous media, without significant gravitational settling and separable from suspension by application of a magnetic field. The particles comprise a magnetic metal oxide core, often surrounded by an adsorptively or covalently bound sheath or coat bearing functional groups to which various molecules, such as DALM or DNA, may be covalently coupled or adsorbed.

Recognition Complex System

An embodiment of the instant invention relates to compositions and apparatus capable of undergoing a process that selectively amplifies nucleic acid ligands that bind to a target analyte. This recognition complex system comprises an array of recognition complexes, each recognition complex comprising a nucleic acid ligand. In various embodiments, the nucleic acid ligand may be attached to an organic semiconductor, such as DALM. In certain embodiments, the recognition complexes are arranged in a two-dimensional array, that may be attached to a glass or other flat surface. In other embodiments, the recognition complexes comprise nucleic acid ligands attached to magnetic bead in a three-dimensional array. In a preferred embodiment, the magnetic beads are suspended in a liquid medium.

The array of recognition complexes is exposed to analyte. Binding of analyte to individual recognition complexes is detected by, for example, changes in the electrical or photochemical properties of the recognition complex upon binding to the analyte. Where the recognition complexes comprise an organic semiconductor, such as DALM, the changes in electrical or photochemical properties may be detected by a variety of techniques, described in detail below.

In certain embodiments, an iterative process may be used to increase the specificity of the array of recognition complexes for the analyte. In each round of iteration, the array is exposed to the analyte. Recognition complexes that bind to the analyte are separated from recognition complexes that do not bind to the analyte. Methods for separating bound from unbound recognition complexes are also described in detail below. The nucleic acid ligands from recognition complexes that bind to the analyte are amplified, for example by PCR, and used to make a new array of recognition complexes. The new array will contain a higher proportion of recognition complexes that bind to the analyte, producing a stronger and more specific electrical or photochemical signal. As discussed below, certain aspects of this process resemble SELEX technology (Tuerk and Gold, 1990; Klug and Famulok, 1994; Tuerk, 1990, 1993, 1997, U.S. Pat. Nos. 5,270,163; 5,475,096; 5,567,588; 5,580,737; 5,595,877; 5,641,629; 5,650,275; 5,683,867; 5,696,249; 5,707,796; 5,763,177; 5,817,785; 5,874,218; 5,958,691; 6,001,577; 6,030,776; each incorporated herein by reference). With each round of iteration, a set of nucleic acid ligands will be produced that bind to the analyte with greater affinity. This iterative process may also be used to produce nucleic acid ligands that bind to the analyte with high affinity. Such high affinity nucleic acid ligands will be useful in numerous applications, described below. One such application involves production of a neutralizing agent that can inactivate or destroy the target analyte.

Embodiments Involving A Chip Type of Array

FIG. 1 illustrates a recognition complex system in accordance with an exemplary embodiment of the present invention. This embodiment of the recognition complex system includes a sample collection unit 105, an analyte isolation unit 110, an organic semiconductor chip based array of recognition complexes 115, a detection unit 120 and a data storage and processing unit 125. In general, the sample collection unit 105 is employed to actively collect or passively receive samples containing the unknown analyte to be identified. The analyte isolation unit 110 is employed to filter the sample and isolate the unknown analyte from other substances or compounds that might be present in the sample. The sample collection unit 105 and the analyte isolation unit 110 may be implemented in accordance with any number of known techniques and/or components known in the art.

The array of recognition complexes 115 comprises one or more individual recognition complexes 130. It will be understood that the array of recognition complexes 115 is shown as comprising 15 recognition complexes for illustrative purposes only. In actuality, the array 115 may contain significantly more than 15 recognition complexes. Within the scope of the invention, the array may comprise approximately 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 125, 130, 140, 150, 160, 170, 175, 180, 185, 190, 200, 225, 250, 275, 300, 325, 350, 375, 400, 425, 450, 475, 500, 550, 600, 650, 700, 750, 800, 850, 900, 950, 1000, 1500, 2000, 2500, 3000, 3500, 4000, 4500, 5000, 6000, 7000, 8000, 9000, 10000, 15000, 20000, 30000, 40000, 50000, 75000, 10000, 20000, 30000, 40000, 50000, 100000, 200000, 500000, $10^6$, $10^7$, $10^8$, $10^9$, $10^{10}$, $10^{11}$, $10^{12}$, $10^{14}$, $10^{16}$, $10^{18}$, $10^{20}$, $10^{22}$, up to $10^{24}$ recognition complexes or any number in between. In certain embodiments, the nucleic acid ligand component of each recognition complex differs in sequence from the nucleic acid ligand component of the other recognition complexes in the array. In other embodiments, some or all of the nucleic acid ligands may be similar or identical in sequence.

Figure 2A:
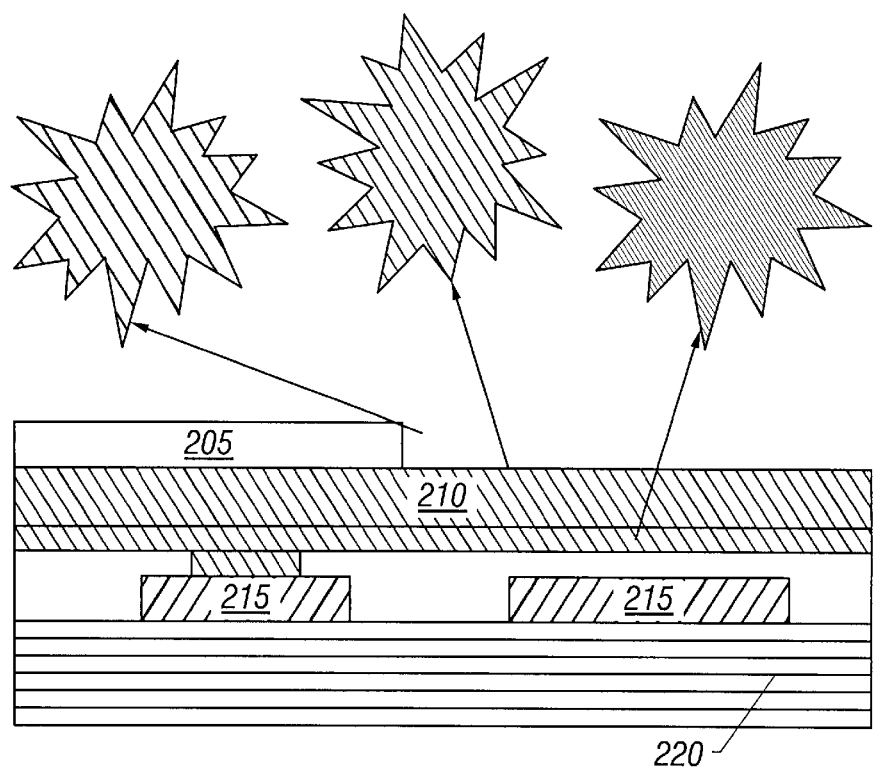

Each of the recognition complexes 130 associated with the array 115 comprises a nucleic acid ligand/organic semiconductor couplet. In a preferred embodiment, the couplet is sandwiched between a pair of electrodes, one of which is preferably transparent, as illustrated in FIG. 2A. The embodiment of the recognition complex system shown in FIG. 2A comprises a transparent electrode 205, one or more nucleic acid ligand/organic semiconductor couplets 210, one or more metal electrodes 215, and a substrate 220. In an exemplary embodiment, the substrate 220 is a glass substrate, although other substrates (e.g., plastic, epoxy, ceramic, composite) are contemplated within the scope of the invention. As indicated in FIG. 2A, in a preferred embodiment the nucleic acid ligand is DNA, although other nucleic acids are contemplated within the scope of the invention. The embodiment of the recognition complex system shown in FIG. 2A is designed for application of a direct current to measure the conductivity of individual recognition complexes.

Figure 2B:
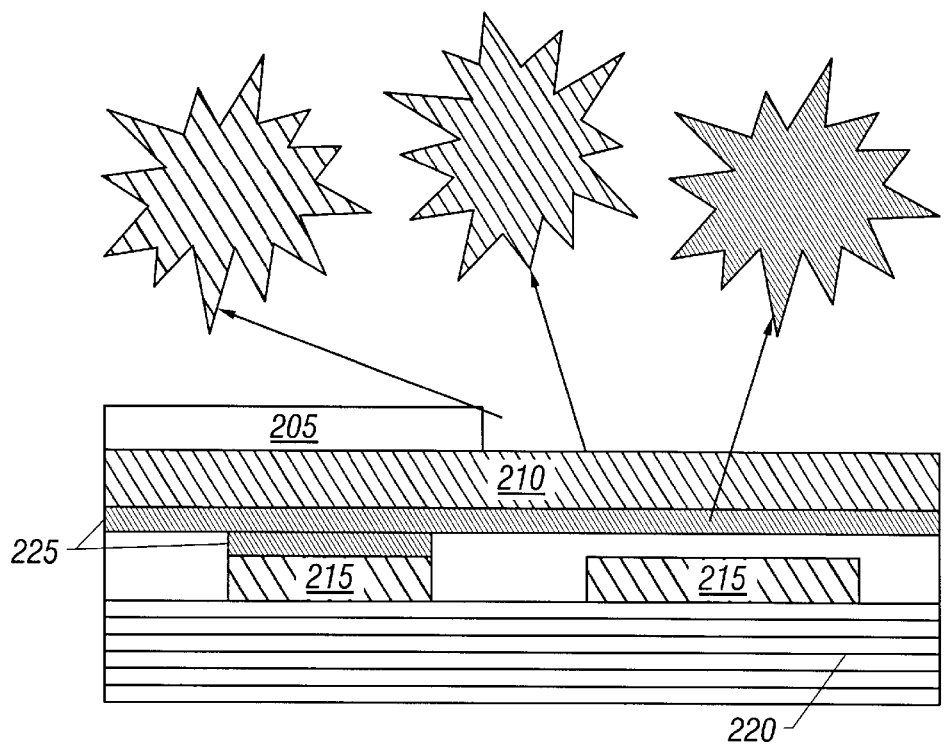

FIGS. 2A and 2B indicate that the recognition complexes may be sandwiched between two electrodes with (for alternating current or forward and reverse DC bias) or without (for DC only) intervening insulating layers 225. This embodiment provides a recognition complex system formed from a miniaturized array of light-emitting diodes. One of the electrodes 205 is transparent and made, for example, of indium tin oxide (ITO) to allow for the passage of light. The other electrode 215 is made of a conductive substance such as copper, aluminum, or gold.

FIG. 2B illustrates an alternative design for a recognition complex system that includes insulation material 225 between each of the two electrodes and the nucleic acid ligand/organic semiconductor couplet. As discussed in greater detail below, it may be desirable to pass current through each of the recognition complexes. In so doing, the various recognition complexes may exhibit characteristics similar to light emitting diodes (LEDs). FIG. 2B represents a configuration for the recognition complex system if alternating current (AC) is employed.

In a preferred embodiment, the organic semiconductor used in diazoluminomelanin (DALM). DALM is a polymer that exhibits slow fluorescent, chemiluminescent, sonochemiluminescent, thermochemiluminescent and electrochemiluminescent properties. However, other organic semiconductors may serve as acceptable substitutes, in particular, polyphenylenes. A non-limiting example of a polyphenylene that might be used within the scope of the instant invention is poly(para-phenylenevinylene) (Kugler et al., 1999).

As shown in FIG. 1, the recognition complex system comprises an array 115 of recognition complexes, such as recognition complex 130. Each of these recognition complexes comprises a nucleic acid ligand/organic semiconductor couplet. Separating each of the recognition complexes is binding material. The nucleic acid ligand sequences present at each of the recognition complexes may be random sequences. In a preferred embodiment, the nucleic acid ligand sequences may be distributed across the array as a function of charge and size, or alternatively as a function of charge and pI (isoelectric point).

After collecting and isolating the unknown analyte, the analyte is applied to each recognition complex associated with the array 115. In those embodiments where the nucleic acid ligand sequences are not identical, some of the nucleic acid ligands will exhibit a high affinity for the analyte, some nucleic acid ligands will exhibit less affinity for the analyte and some nucleic acid ligands will exhibit no affinity for the analyte. The electrical and/or photochemical properties of the nucleic acid ligand/organic semiconductor couplet will change depending on the degree to which the nucleic acid ligands bind to the analyte. The electrical and/or photochemical properties associated with some recognition complexes will change significantly, while the electrical and/or photochemical properties associated with other recognition complexes may change very little, if at all, upon exposure to a given analyte.

In accordance with one exemplary embodiment, one of the electrodes 205 associated with each recognition complex is transparent. The transparency of this electrode permits excitation energy, such as light, to be transmitted through each recognition complex. In a preferred embodiment, ultra-violet light is employed. The passage of ultra-violet or other frequency irradiation through each of the recognition complexes 130 may permit detection unit 120 to more easily detect and quantify any photochemical changes that take place at each recognition complex 130 as a result of binding to the analyte. The photochemical changes may involve changes in the color of the nucleic acid ligand/organic semiconductor couplet and/or changes in the color intensity. In preferred embodiments, the detection unit 120 comprises a charge coupled device (CCD), such as a CCD camera, digital camera, photomultiplier tube or any other functionally equivalent detector.

The photochemical signature of the analyte may consist of a two-dimensional distribution of fluorescence resulting from long-wavelength ultraviolet light excitation. Response of the array 115 at a specific spatial location 130 may be similar for two or more different analytes, but by combining the fluorescence response of many independent measurement locations, specificity can be high. A typical consumer-type CCD-based color video camera has 768×494 discrete detectors. A miniaturized cell utilizing such a camera with a array could have about 380,000 parallel channels (single detectors). Practical considerations would group detectors for lower but less spatially noisy resolution with fewer channels. Hundreds to thousands of channels could easily be achieved. Optimization of the number of channels would minimize channels and thus computational load, while maximizing specificity and classification accuracy.

Analysis of the photochemical signature, by data processing unit 125, may involve a comparison of multiple channels of fluorescence spectral signatures. Use of CIE colorimetry methods may streamline processing by representing spectral distributions at each spatial location as CIE chromaticity coordinates (two numbers). Such methods also provide an analytical technique that is color oriented and relatively independent of intensity. Comparison of signatures by data processing unit 125 may be implemented using artificial neural networks (such as the Qnet v2000 neural net software package from Vesta Services, Inc., 1001 Green Bay Rd., Winnetka, Ill. 60093), look-up tables or various other decision methods, operating on the arrays of two-number (CIE chromaticity) coordinates that are the signatures for identified analytes. This would provide a fast comparison of unknown analytes to a database of previously recorded signatures of known analytes.

Any binding between the analyte and the nucleic acid ligand associated with a given recognition complex may alter the electrical properties of the corresponding nucleic acid ligand/organic semiconductor couplet. In another exemplary embodiment, a voltage is applied across each recognition complex of the array 115 after the analyte has been introduced. The amount of current that is able to flow across each recognition complex is a function of the conductivity of the nucleic acid ligand/organic semiconductor couplet. Changes in conductivity of each couplet upon binding of analyte may be stored and analyzed to identify the analyte.

In certain embodiments, voltage may be applied across each of the recognition complexes in addition to exciting each recognition complex with ultraviolet or other frequency irradiation. In such embodiments, changes in both the electrical properties and the photochemical properties of each recognition complex may be detected and analyzed. These combined data may more readily establish a unique signature for identifying the analyte. In these embodiments, the detection unit 120 would have to include the ability to detect both changes in current and photochemical changes at each of the recognition complexes. Application of a current flowing through the recognition complexes may result in the enhancement of any photochemical changes that take place as a result of analyte/nucleic acid ligand binding, thereby making it easier for the detection unit 120 to detect and quantify those photochemical changes.

In accordance with one aspect of the present invention, unknown chemical and biological analytes may be detected and identified in a single, automated binding step, as the reaction between the analyte and the nucleic acid ligand sequences distributed across the array 115 produces a relatively unique change in the electrical and/or photochemical properties of the array as a whole. However, where two or more analytes share similar chemical structures, they might cause the array 115 to produce a relatively similar electrical and/or photochemical response.

Thus, in accordance with another aspect of the present invention, a more unique electrical and/or photochemical response from the array 115 can be achieved to more clearly distinguish between structurally similar analytes. To accomplish this, the nucleic acid ligands associated with those recognition complexes that bind to the analyte, as indicated by changes in electrical or photochemical properties, may extracted from the array.

In certain embodiments, individual recognition complexes 130 may be detached from the array 115 by heating the array at the location of each such recognition complex. The nucleic acid ligand sequences exhibiting affinity for analyte may be separated from the analyte by washing the nucleic acid ligand bound to analyte with deionized water. The nucleic acid ligand sequences that exhibit no affinity for the analyte can be discarded. The extracted nucleic acid ligand sequences may be amplified and applied to a clean chip to produce a new array 115. Since the new array 115 comprises only those nucleic acid ligand sequences that were identified as binding to the analyte, it should exhibit a greater degree of specificity and a higher binding affinity for the analyte.

As the process of amplification inherently produces some variation in the amplified nucleic acid ligand sequences, due to the normal error rate of DNA or RNA polymerase, the amplified nucleic acid ligands may exhibit some sequences that were not present on the initial array, although they will generally be identical or almost identical in sequence to the original nucleic acid ligands. These sequence variants may also exhibit variability in their binding affinity for the analyte, with some sequence variants exhibiting an increased affinity for analyte. The iterative process may be used to select for nucleic acid ligand sequences that bind to analyte with higher affinity with each round of iteration. The skilled artisan will realize that use of polymerases with a greater inherent error rate, or manipulation of amplification conditions to increase the error rate, may be desirable in certain embodiments of the present invention.

Once a new array chip 115 is produced, analyte may be introduced to each of the array recognition complexes 130, and the electrical and/or photochemical changes across the array may be detected and analyzed, producing an even more unique signature that can be used for analyte identification and to distinguish the analyte from chemically or structurally similar species.

The production of chips for attachment of nucleic acid ligands is well known in the art. The chip may comprise a Langmuir-Bodgett film, functionalized glass, germanium, silicon, PTFE, polystyrene, gallium arsenide, gold, silver, membrane, nylon, PVP, or any other material known in the art that is capable of haying functional groups such as amino, carboxyl, Diels-Alder reactants, thiol or hydroxyl incorporated on its surface. In certain embodiments, these groups may be covalently attached to cross-linking agents so that binding interactions between analyte and recognition complex occur without steric hindrance from the chip surface. Typical cross-linking groups include ethylene glycol oligomer, diamines and amino acids. Any suitable technique useful for immobilizing a recognition complex on a chip is contemplated by this invention, including sialinization. In preferred embodiments, the DALM is attached to the chip surface and nucleic acid ligands are then attached, covalently or non-covalently, to the DALM.

The array-based chip design 115 may be distinguished from conventional biochips (e.g., U.S. Pat. Nos. 5,861,242 and 5,578,832) by a number of characteristics, including the use of an organic semiconductor, such as DALM. Additionally, conventional biochips typically are constructed by attaching or synthesizing nucleic acid ligands having affinities for known analytes on specific identified locations on the chip. The presence of a target analyte in a sample is detected by binding to the specific chip locus containing a nucleic acid ligand with known affinity for that analyte. In contrast, in certain embodiments of the present invention the affinities of the nucleic acid ligand/organic semiconductor couplets for various analytes are unknown at the time they are initially attached to the chip. Target analytes are identified by their pattern of binding to the entire chip, not by their binding to a specific locus on the chip. This system provides greater efficiency and flexibility, in that it is not necessary to prepare nucleic acid ligands of known specificity before construction of the chip. Further, previously unknown analytes may be characterized by their pattern of interaction with the chip, without having to clone and sequence their RNA or DNA or prepare high-affinity aptamers in advance of chip production.

This is not meant to exclude the possibility of selecting for the presence of one or more nucleic acid ligands with higher affinity for the target through use of a SELEX-type process. Such higher affinity nucleic acid ligands may be used to generate a new array 115 with increased affinity or specificity for the target. That capability further distinguishes the present invention from conventional biochips, which do not utilize iterative amplification of selected nucleic acid ligands to generate new chips with higher specificity or affinity for a target analyte.

Embodiments Involving Magnetic Beads

In an alternative embodiment, the nucleic acid ligand sequences may be attached to magnetic beads instead of to a glass or other flat surface. In this case, each recognition complex would comprise a magnetic bead attached to one or more nucleic acid ligands. In a preferred embodiment, each nucleic acid ligand molecule attached to the same magnetic bead will have the same sequence. In other embodiments, the nucleic acid ligand molecules attached to a single bead may have different sequences. In certain preferred embodiments, the nucleic acid ligands will also be attached to an organic semiconductor, such as DALM. Attachment of nucleic acid ligands to DALM would facilitate the detection and quantitation of analyte binding to the nucleic acid ligands, as described above.

The skilled artisan will realize that use of magnetic bead technology would facilitate certain applications of the invention, such as the iterative process for producing nucleic acid ligands of higher specificity and greater binding affinity for the analyte. With magnetic bead technology, the individual recognition complexes are more easily manipulated and separated according to their characteristics. For example, recognition complexes that bind to the analyte may be separated from recognition complexes that do not bind to the analyte by using a magnetic flow cell or filter block, as disclosed in U.S. Pat. No. 5,972,721, incorporated herein by reference in its entirety.

Figure 3:
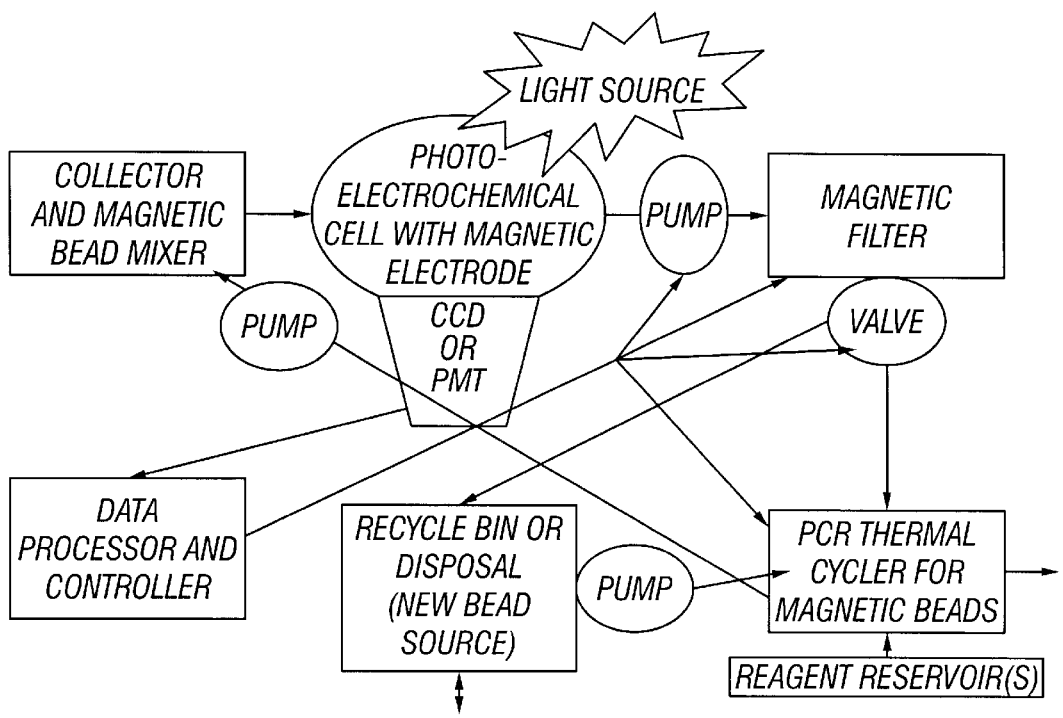

A diagram for use of magnetic beads in a recognition complex system is shown in FIG. 3. Nucleic acid ligands of random or non-random sequence may be synthesized or amplified and attached to magnetic beads. The individual recognition complexes, each corresponding to a magnetic bead attached to one or more nucleic acid ligands, together comprise an array, similar to that described above for FIG. 1. The array is added to the magnetic bead mixer (FIG. 3) and analyte is added and allowed to bind to the nucleic acid ligands. The mixture is then transferred to a photo-electrochemical cell with a magnetic electrode, where the mixture may be exposed to ultraviolet or other irradiation. A CCD, photomultiplier tube, digital camera or other detection device may be used to obtain absorption or emission spectra. As described above, binding of analyte will result in characteristic changes in the photochemical properties of individual recognition complexes. These changes in photochemical properties will be detected and analyzed to produce an analyte signature, as described above. Although the suspension of recognition complexes in the bead mixer is random, the use of a magnetic electrode in the photo-electrochemical cell will provide a spatial distribution of recognition complexes, analogous to the two-dimensional array 115 described above. Beads will deposit and separate on the surface of the magnetic electrode according to their accumulated mass (from binding analyte). This spatial distribution, along with the detected photochemical changes, may be analyzed to produce a unique signature that can be used to identify the analyte.

After detection, the recognition complexes may be transferred to a magnetic filter (FIG. 3), where the recognition complexes that bind to the analyte may be separated from those that do not bind analyte. The recognition complexes that do not bind analyte are transferred to the recycle bin (FIG. 3), where the nucleic acid ligands may be detached from the magnetic beads. The magnetic beads may be disposed of or recycled for attachment to new nucleic acid ligands. Those recognition complexes that bind to the analyte may be transferred to a PCR cycler (FIG. 3), where the nucleic acid ligand sequences may be amplified. The new nucleic acid ligand sequences are attached to magnetic beads and transferred to the magnetic bead mixer (FIG. 3) for another iteration of the process. This iterative process may be used to produce nucleic acid ligands that bind with high affinity to the analyte, or may be used to produce an array with greater specificity for the target analyte. Certain components that may be incorporated into a recognition complex system as shown in FIG. 3 include pumps an valves to facilitate fluid transfer between different components of the recognition complex system. It is anticipated that virtually any pump or valve capable of producing a controlled fluid transfer between one component and another component of the recognition complex system illustrated in FIG. 3 could be used.

Figure 4:
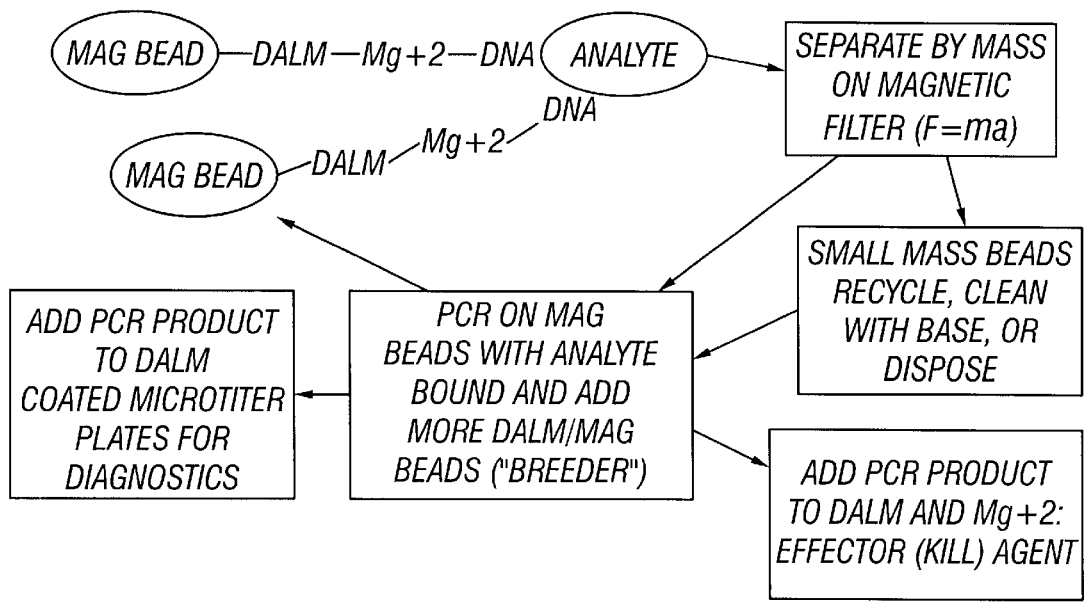

Processes for the coupling of molecules to magnetic beads or a magnetite substrate are well known in the art, i.e. U.S. Pat. Nos. 4,695,393, 3,970,518, 4,230,685, and 4,677,055 herein expressly incorporated by reference. Alternatively, DALM may be attached directly to the magnetic bead (FIG. 4). Nucleic acid ligands, such as DNA, may be attached to DALM by electrostatic interaction with magnesium ion (FIG. 4). This would facilitate detachment of DNA from the DALM/magnetic bead, since DNA would be released by addition of a chelating agent such as EDTA (ethylene diamine tetraacetic acid).

Figure 5:
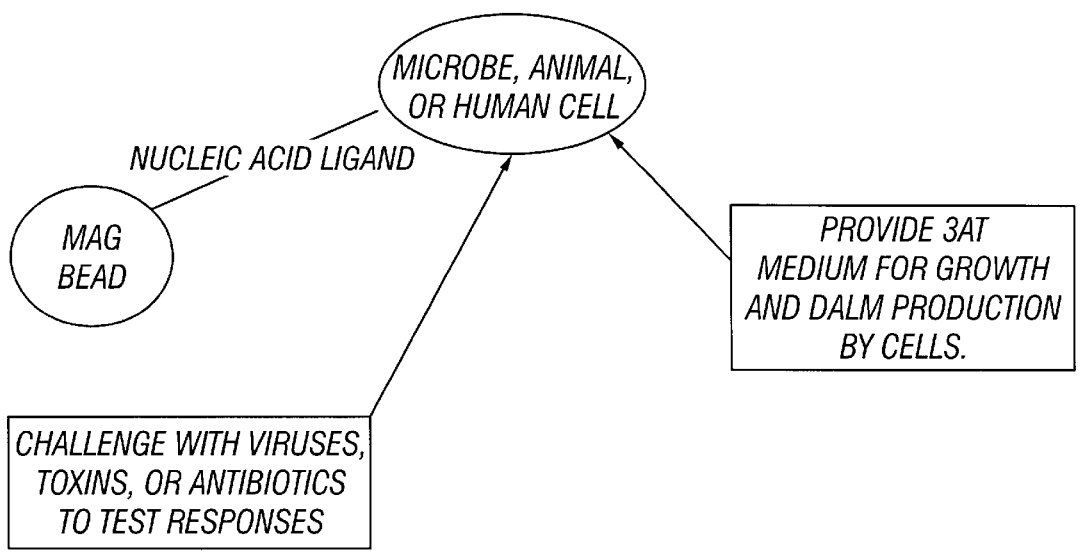

As shown in FIG. 4, the analyte may bind to one or more recognition complexes. Those recognition complexes bound to the analyte may be separated from unbound recognition complexes by mass segregation, using a magnetic filter (see FIG. 3). The nucleic acid ligands (indicated in FIG. 4 as DNA) with affinity for analyte may be amplified by PCR or other methods described below. The amplified nucleic acid ligands may be attached to DALM and/or magnetic beads for another iteration of analyte binding and detection, or may be collected and used for other purposes, such as analyte neutralization or preparation of high-affinity diagnostic devices for detecting analyte in the field (FIG. 4). In one embodiment, the high-affinity nucleic acid ligand, attached to magnetic beads, may be used in a viability assay to determine the sensitivity of eukaryotic or prokaryotic cells to various agents, such as viruses, toxins, antibiotics and other agents (FIG. 5). In a preferred embodiment, viability may be determined by assaying the ability of the cell to manufacture DALM, as described below.

It is envisioned that particles employed in the instant invention may come in a variety of sizes. While large magnetic particles (mean diameter in solution greater than 10 μm) can respond to weak magnetic fields and magnetic field gradients, they tend to settle rapidly, limiting their usefulness for reactions requiring homogeneous conditions. Large particles also have a more limited surface area per weight than smaller particles, so that less material can be coupled to them. In preferred embodiments, the magnetic beads are less than 10 μm in diameter.

Various silane couplings applicable to magnetic beads are discussed in U.S. Pat. No. 3,652,761, incorporated herein by reference. Procedures for silanization known in the art generally differ from each other in the media chosen for the polymerization of silane and its deposition on reactive surfaces. Organic solvents such as toluene (Weetall, (1976)), methanol, (U.S. Pat. No. 3,933,997) and chloroform (U.S. Pat. No. 3,652,761) have been used. Silane deposition from aqueous alcohol and aqueous solutions with acid have also been used.

Ferromagnetic materials in general become permanently magnetized in response to magnetic fields. Materials termed "superparamagnetic" experience a force in a magnetic field gradient, but do not become permanently magnetized. Crystals of magnetic iron oxides may be either ferromagnetic or superparamagnetic, depending on the size of the crystals. Superparamagnetic oxides of iron generally result when the crystal is less than about 300 angstroms (Å) in diameter; larger crystals generally have a ferromagnetic character.

Dispersible magnetic iron oxide particles reportedly having 300 Å diameters and surface amine groups were prepared by base precipitation of ferrous chloride and ferric chloride ($Fe^{2+}/Fe^{3+}=1$) in the presence of polyethylene imine, according to U.S. Pat. No. 4,267,234. These particles were exposed to a magnetic field three times during preparation and were described as redispersible. The magnetic particles were mixed with a glutaraldehyde suspension polymerization system to form magnetic polyglutaraldehyde microspheres with reported diameters of 0.1 μm. Polyglutaraldehyde microspheres have conjugated aldehyde groups on the surface which can form bonds to amino containing molecules such as proteins.

While a variety of particle sizes are envisioned to be applicable in the disclosed method, in a preferred embodiment, particles are between about 0.1 and about 1.5 μm diameter. Particles with mean diameters in this range can be produced with a surface area as high as about 100 to 150 $m^2/gm$, which provides a high capacity for bioaffinity adsorbent coupling. Magnetic particles of this size range overcome the rapid settling problems of larger particles, but obviate the need for large magnets to generate the magnetic fields and magnetic field gradients required to separate smaller particles. Magnets used to effect separations of the magnetic particles of this invention need only generate magnetic fields between about 100 and about 1000 Oersteds. Such fields can be obtained with permanent magnets which are preferably smaller than the container which holds the dispersion of magnetic particles and thus, may be suitable for benchtop use. Although ferromagnetic particles may be useful in certain applications of the invention, particles with superparamagnetic behavior are usually preferred since superparamagnetic particles do not exhibit the magnetic aggregation associated with ferromagnetic particles and permit redispersion and reuse.

The method for preparing the magnetic particles may comprise precipitating metal salts in base to form fine magnetic metal oxide crystals, redispersing and washing the crystals in water and in an electrolyte. Magnetic separations may be used to collect the crystals between washes if the crystals are superparamagnetic. The crystals may then be coated with a material capable of adsorptively or covalently bonding to the metal oxide and bearing functional groups for coupling with nucleic acid ligands or DALM.

Embodiments Involving Flow Cells

In another exemplary embodiment, each of the recognition complexes associated with the array 115 may comprise a flow cell (FIG. 6). The flow cell is designed to be easily removable from the array 115 and to sit directly on an inverted optical microscope. Either transmitted or incident illumination may be used since the flow cell is transparent. The primary purpose for implementing the array 115 using flow cells is to permit more detailed analysis of the analyte and nucleic acid ligand interaction with particulate structures. The flow cell structure described below is exemplary of a preferred embodiment of the invention. The skilled artisan will realize that alternative flow cell designs that will function equivalently are contemplated within the scope of the present invention.

The flow cell volume is about 200 μl (i.e., 0.5 inches in diameter with a thickness of 0.06 inches). The area of maximum light transmission 630 is 0.25 inches in diameter. This area is large enough to include two working electrode areas 650, each of about 2 square millimeters.

The cell has three parts—a body 600 and 655, a window 615 and a clamp. The clamp is an acrylic ring with four 10–40 machine screws 620 through the body 600 and 655. The body may be subdivided into two layers. The top layer 600 is an acrylic disk 3–4 inches in diameter and 0.125 inches thick. The central 0.5 inches of the disk is the reservoir area 660, wherein the reservoir depth is defined by the thickness of the o-ring within an o-ring groove 605. The o-ring groove 605 on the top layer is formed by solvent-gluing two 0.06 inch rings of acrylic to the body. The bottom layer of the body 655 provides mechanical strength. It is an acrylic disk 655 identical to the top layer 600, but with a 0.25 inch hole in the center 630. The light at the working electrode 610 only passes through 0.125 inch acrylic, but 0.25 inch thick acrylic provides mechanical strength at the fluid 640 and electrode ports 635 and 645.

The top 600 and bottom 655 acrylic layers are solvent-cemented together. Through these two disks 600 and 655, around the rim of the 0.25 inch recess 660, are drilled two 0.06 inch holes 640 for movement of fluid in and out. There are also three 0.038 inch holes for electrodes 635 and 645. Two of the holes 635 hold the counter electrode in place (i.e., a loop of 1 mm platinum wire rimming the cell cavity), and 1 hole 645 is for the reference electrode (i.e., a chloridized silver wire).

The window 625 associated with the working electrode is 0.9 mm glass with 20 ohm/square ITO on one side, 1.5 inch square. The ITO is patterned photolithographically and etched to leave two 3 mm wide parallel bars 665, separated by 1 mm and narrowing to a central 2.5×2.5 mm region 650. Aluminum is deposited on these bars 0.2 microns thick, except for the 2.5 mm square 650. Silicon nitride is deposited over the aluminum and the glass, except the central square 650 and the outermost 5 mm on each end. The result is two independent transparent working electrodes that can be independently heated resistively. The ends of the aluminum bars are contacted electrically by brushes imbedded into the surface of the body 610. The platinum counter electrode is a wire positioned in solution in a circle around the perimeter of the flow chamber.

Recognition Complex System Model

Figure 8A:
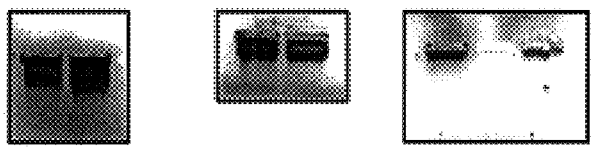
Figure 8B:
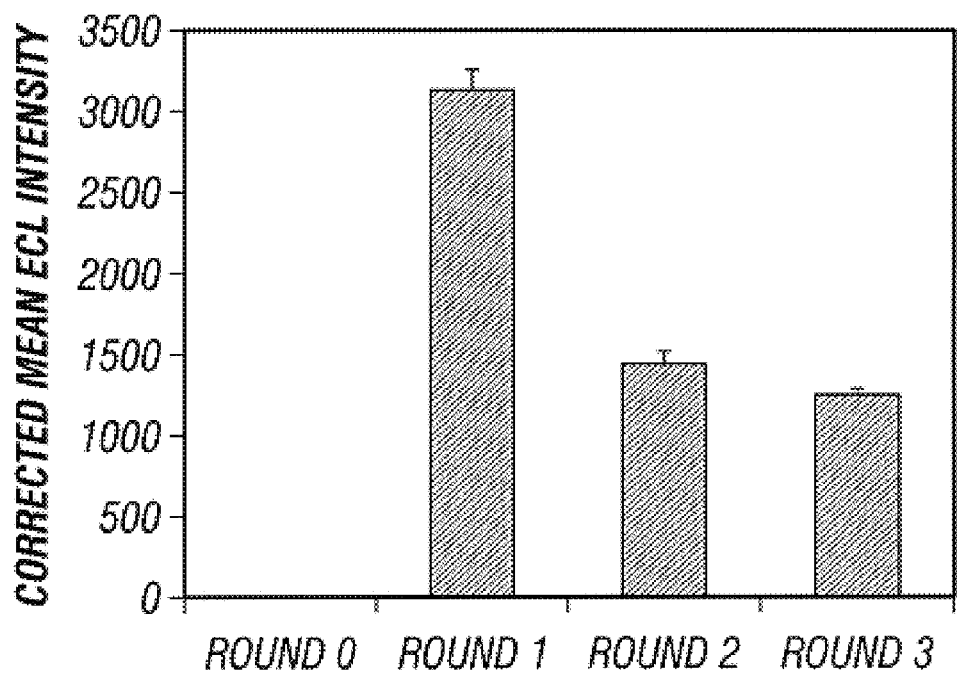

In another embodiment, the nucleic acid ligand sequences that exhibit the greatest degree of affinity for the analyte can be amplified and/or chemically synthesized and employed as an agent to neutralize adverse biological effects associated with the detected analyte. In this aspect, the recognition complex system functions in a manner similar to the human immune system (FIG. 7). The recognition complex system initially generates a somewhat non-specific response, though sufficient to identify previously detected analytes. Following one or more rounds of selection and amplification of nucleic acid ligand sequences that bind to analyte with higher affinity, the recognition complex system responds in a more specific way to neutralize any previously unknown analyte. The increased specificity of amplified nucleic acid ligands for the target analyte with increasing rounds of selection and amplification is shown in FIG. 8. In this figure, a SELEX process has been used to amplify those nucleic acid ligands that bind to analyte. Both the SELEX process and aptamer technology are described in detail below.

Nucleic Acids

Nucleic acid ligands within the scope of the present invention may be made by any technique known to one of ordinary skill in the art. Examples of nucleic acid ligands, particularly synthetic oligonucleotides, include a nucleic acid ligand made by in vitro chemical synthesis using phosphotriester, phosphite or phosphoramidite chemistry and solid phase techniques (EP 266,032, incorporated herein by reference) or via deoxynucleoside H-phosphonate intermediates (Froehler et al., 1986, and U.S. patent Ser. No. 5,705,629, each incorporated herein by reference). Examples of enzymatically produced nucleic acid ligands include those produced by amplification reactions such as PCR™ (e.g., U.S. Pat. No. 4,683,202 and U.S. Pat. No. 4,683,195, each incorporated herein by reference), or the synthesis of oligonucleotides described in U.S. Pat. No. 5,645,897, incorporated herein by reference. Examples of a biologically produced nucleic acid ligand include recombinant nucleic acid production in living cells, such as recombinant DNA vector production in bacteria (e.g., Sambrook et al. 1989, incorporated herein by reference).

Nucleobase, nucleoside and nucleotide mimics or derivatives are well known in the art, and have been described in exemplary references such as, for example, Scheit, Nucleotide Analogs (Joln Wiley, New York, 1980), incorporated herein by reference. Purine and pyrimidine nucleobases encompass naturally occurring purines and pyrimidines and derivatives and mimics thereof. These include, but are not limited to, purines and pyrimidines substituted with one or more alkyl, carboxyalkyl, amino, hydroxyl, halogen (i.e. fluoro, chloro, bromo, or iodo), thiol, or alkylthiol groups. The alkyl substituents may comprise from about 1, 2, 3, 4, or 5, to about 6 carbon atoms.

Examples of purines and pyrimidines include deazapurines, 2,6-diaminopurine, 5-fluorouracil, xanthine, hypoxanthine, 8-bromoguanine, 8-chloroguanine, bromothymine, 8-aminoguanine, 8-hydroxyguanine, 8-methylguanine, 8-thioguanine, azaguanines, 2-aminopurine, 5-ethylcytosine, 5-methylcytosine, 5-bromouracil, 5-ethyluracil, 5-iodouracil, 5-chlorouracil, 5-propyluracil, thiouracil, 2-methyladenine, methylthioadenine, N,N-dimethyladenine, azaadenines, 8-bromoadenine, 8-hydroxyadenine, 6-hydroxyaminopurine, 6-thiopurine, 4-(6-aminohexyl/cytosine), and the like. A list of exemplary purine and pyrimidine derivatives and mimics is provided in Table 1.

TABLE 1

Purine and Pyrimidine Derivatives or Mimics

| Abbr. | Modified base description | Abbr. | Modified base description |
|---|---|---|---|
| ac4c | 4-acetylcytidine | mam5s2u | 5-methoxyaminomethyl-2-thiouridine |
| chm5u | 5-(carboxyhydroxylmethyl)uridine | man q | Beta,D-mannosylqueosine |
| Cm | 2'-O-methylcytidine | mcm5s2u | 5-methoxycarbonylmethyl-2-thiouridine |
| cmnm5s2u | 5-carboxymethylaminomethyl-2-thioridine | mcm5u | 5-methoxycarbonylmethyluridine |
| cmnm5u | 5-carboxymethylaminomethyluridine | mo5u | 5-methoxyuridine |
| D | Dihydrouridine | ms2i6a | 2-methylthio-N6-isopentenyladenosine |
| Fm | 2'-O-methylpseudouridine | ms2t6a | N-((9-beta-D-ribofuranosyl-2 methylthiopurine-6-yl)carbamoyl)threonine |
| gal q | beta,D-galactosylqueosine | mt6a | N-((9-beta-D-ribofuranosylpurine 6-yl)N-methyl-carbamoyl)threonine |
| Gm | 2'-O-methylguanosine | mv | Uridine-5-oxyacetic acid methylester |
| I | Inosine | o5u | Uridine-5-oxyacetic acid (v) |
| i6a | N6-isopentenyladenosine | osyw | Wybutoxosine |
| m1a | 1-methyladenosine | p | Pseudouridine |
| m1f | 1-methylpseudouridine | q | Queosine |
| m1g | 1-methylguanosine | s2c | 2-thiocytidine |
| m1I | 1-methylinosine | s2t | 5-methyl-2-thiouridine |
| m22g | 2,2-dimethylguanosine | s2u | 2-thiouridine |
| m2a | 2-methyladenosine | s4u | 4-thiouridine |
| m2g | 2-methylguanosine | t | 5-methyluridine |
| m3c | 3-methylcytidine | t6a | N-((9-beta-D-ribofuranosylpurine 6-yl)carbamoyl)threonine |
| m5c | 5-methylcytidine | tm | 2'-O-methyl-5-methyluridine |
| m6a | N6-methyladenosine | um | 2'-O-methyluridine |
| m7g | 7-methylguanosine | yw | Wybutosine |

TABLE 1-continued

Purine and Pyrimidine Derivatives or Mimics

| Abbr. | Modified base description | Abbr. | Modified base description |
|---|---|---|---|
| mam5u | 5-methylaminomethyluridine | x | 3-(3-amino-3-carboxypropyl)uridine, (acp3)u |

An example of a nucleic acid ligand comprising nucleoside or nucleotide derivatives and mimics is a "polyether nucleic acid", described in U.S. patent Ser. No. 5,908,845, incorporated herein by reference, wherein one or more nucleobases are linked to chiral carbon atoms in a polyether backbone. Another example of a nucleic acid ligand is a "peptide nucleic acid", also known as a "PNA", "peptide-based nucleic acid mimics" or "PENAMs", described in U.S. patent Ser. Nos. 5,786,461, 5,891,625, 5,773,571, 5,766,855, 5,736,336, 5,719,262, 5,714,331, 5,539,082, and WO 92/20702, each of which is incorporated herein by reference. A peptide nucleic acid generally comprises at least one nucleobase and at least one nucleobase linker moiety that is not a 5-carbon sugar and/or at least one backbone moiety that is not a phosphate group. Examples of nucleobase linker moieties described for PNAs include aza nitrogen atoms, amido and/or ureido tethers (see for example, U.S. Pat. No. 5,539,082). Examples of backbone moieties described for PNAs include an aminoethylglycine, polyamide, polyethyl, polythioamide, polysulfinamide or polysulfonamide backbone moiety.

Peptide nucleic acids generally have enhanced sequence specificity, binding properties, and resistance to enzymatic degradation in comparison to molecules such as DNA and RNA (Egholm et al., Nature 1993, 365, 566; PCT/EP/01219). In addition, U.S. Pat. Nos. 5,766,855, 5,719,262, 5,714,331 and 5,736,336 describe PNAs comprising nucleobases and alkylamine side chains with further improvements in sequence specificity, solubility and binding affinity. These properties promote double or triple helix formation between a target and the PNA.

Various nucleic acid ligand segments may be designed based on a particular nucleic acid sequence, and may be of any length. By assigning numeric values to a sequence, for example, the first residue is 1, the second residue is 2, etc., an algorithm defining all nucleic acid segments can be created:

n to n+y where n is an integer from 1 to the last number of the sequence and y is the length of the nucleic acid segment minus one, where n+y does not exceed the last number of the sequence. Thus, for a 10-mer, the nucleic acid segments correspond to bases 1 to 10, 2 to 11, 3 to 12 . . . and/or so on. For a 15-mer, the nucleic acid segments correspond to bases 1 to 15, 2 to 16, 3 to 17 . . . and/or so on. For a 20-mer, the nucleic segments correspond to bases 1 to 20, 2 to 21, 3 to 22, etc.

The skilled artisan will realize that the present invention is not limited to the examples disclosed herein, but may include nucleobases, nucleotides and nucleic acids produced by any other means known in the art.

Amplification

In certain embodiments, the nucleic acid ligands of the recognition complex system may be amplified to provide a source of high affinity nucleic acid ligands for neutralizing analytes. Amplification may also be of use in the iterative process for generating arrays with greater specificity or binding affinity for the analyte. Within the scope of the present invention, amplification may be accomplished by any means known in the art. Exemplary embodiments are described below.

Primers

The term primer, as defined herein, is meant to encompass any nucleic acid that is capable of priming the synthesis of a nascent nucleic acid in a template-dependent process. Typically, primers are oligonucleotides from ten to twenty base pairs in length, but longer sequences may be employed. Primers may be provided in double-stranded or single-stranded form, although the single-stranded form is preferred.

Amplification Methods

A number of template dependent processes are available to amplify the marker sequences present in a given template sample. One of the best known amplification methods is the polymerase chain reaction (referred to as PCR) which is described in detail in U.S. Pat. Nos. 4,683,195, 4,683,202 and 4,800,159, and in Innis et al., 1990, each of which is incorporated herein by reference in its entirety.

Briefly, in PCR, two primer sequences are prepared which are complementary to regions on opposite complementary strands of, for example, a nucleic acid ligand. An excess of deoxynucleoside triphosphates are added to a reaction mixture along with a DNA polymerase, e.g., Taq polymerase. Examples of polymerases that may be used for purposes of nucleic acid amplification are provided in Table 2 below. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the nucleic acid ligand to form reaction products, excess primers will bind to the nucleic acid ligand and to the reaction products and the process is repeated.

A reverse transcriptase PCR amplification procedure may be performed in order to quantify the amount of mRNA amplified. Methods of reverse transcribing RNA into cDNA are well known and described in Sambrook et al., 1989. Alternative methods for reverse transcription utilize thermostable DNA polymerases. These methods are described in WO 90/07641 filed Dec. 21, 1990. Polymerase chain reaction methodologies are well known in the art. The most preferred methods of RT-PCR are as described herein in Example 1.

Another method for amplification is the ligase chain reaction ("LCR"), disclosed in European Application No. 320 308, incorporated herein by reference in its entirely. In LCR, two complementary probe pairs are prepared, and in the presence of the nucleic acid ligand sequence, each pair will bind to opposite complementary strands of the target such that they abut. In the presence of a ligase, the two probe pairs will link to form a single unit. By temperature cycling, as in PCR, bound ligated units dissociate from the nucleic acid ligand and then serve as templates for ligation of excess probe pairs. U.S. Pat. No. 4,883,750 describes a method similar to LCR for binding probe pairs to a nucleic acid ligand sequence.

Qbeta Replicase, described in PCT Application No. PCT/US87/00880, may also be used as still another amplification method in the present invention. In this method, a replicative sequence of RNA which has a region complementary to that of a nucleic acid ligand is added to a sample in the presence of an RNA polymerase. The polymerase will copy the replicative sequence which may then be detected.

An isothermal amplification method, in which restriction endonucleases and ligases are used to achieve the amplification of nucleic acid ligand molecules that contain nucleotide 5'-[alpha-thio]-triphosphates in one strand of a restriction site may also be useful in the amplification of nucleic acid ligands in the present invention. Walker et al., (1992), incorporated herein by reference in its entirety.

Strand Displacement Amplification (SDA) is another method of carrying out isothermal amplification of nucleic acid ligands which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases may be added as biotinylated derivatives for easy detection. A similar approach is used in SDA. Target specific sequences may also be detected using a cyclic probe reaction (CPR). In CPR, a probe having 3' and 5' sequences of non-specific DNA and a middle sequence of specific RNA is hybridized to DNA which is present in a sample. Upon hybridization, the reaction is treated with RNase H, and the products of the probe identified as distinctive products which are released after digestion. The original template is annealed to another cycling probe and the reaction is repeated.

Still other amplification methods described in GB Application No. 2 202 328, and in PCT Application No. PCT/US89/01025, each of which is incorporated herein by reference in its entirety, may be used in accordance with the present invention. In the former application, "modified" primers are used in a PCR like, template and enzyme dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the nucleic acid ligand sequence is released intact to be bound by excess probe. Cleavage of the labeled probe signals the presence of the nucleic acid ligand sequence.

Other nucleic acid ligand amplification procedures include transcription-based amplification systems (TAS), including nucleic acid sequence based amplification (NASBA) and 3SR. Kwoh el al., (1989) and PCT Application WO 88/10315, incorporated herein by reference in their entirety. In NASBA, the nucleic acid ligands may be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has nucleic acid ligand specific sequences. Following polymerization, DNA/RNA hybrids are digested with RNase H while double stranded DNA molecules are heat denatured again. In either case the single stranded DNA is made fully double stranded by addition of second nucleic acid ligand specific primer, followed by polymerization. The double-stranded DNA molecules are then multiply transcribed by a polymerase such as T7 or SP6. In an isothermal cyclic reaction, the RNA's are reverse transcribed into double stranded DNA, and transcribed once against with a polymerase such as T7 or SP6. The resulting products, whether truncated or complete, indicate nucleic acid ligand specific sequences.

Davey et al., European Application No. 329 822 (incorporated herein by reference in its entirely) disclose a nucleic acid amplification process involving cyclically synthesizing single-stranded RNA ("ssRNA"), ssDNA, and double-stranded DNA (dsDNA), which may be used in accordance with the present invention. The ssRNA is a first template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a second template for a second primer, which also includes the sequences of an RNA polymerase promoter (exemplified by T7 RNA polymerase) 5' to its homology to the template. This primer is then extended by DNA polymerase (exemplified by the large "Klenow" fragment of E. coli DNA polymerase I), resulting in a double-stranded DNA ("dsDNA") molecule, having a sequence identical to that of the original RNA between the primers and having additionally, at one end, a promoter sequence. This promoter sequence may be used by the appropriate RNA polymerase to make many RNA copies of the DNA. These copies may then re-enter the cycle leading to very swift amplification. With proper choice of enzymes, this amplification may be done isothermally without addition of enzymes at each cycle. Because of the cyclical nature of this process, the starting sequence may be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR." Frohman, (1990) and Ohara et al., (1989), each herein incorporated by reference in their entirety.

Methods based on ligation of two (or more) oligonucleotides in the presence of nucleic acid having the sequence of the resulting "di-oligonucleotide", thereby amplifying the di-oligonucleotide, may also be used in the amplification step of the present invention. Wu et al., *Genomics* 4:560 (1989), incorporated herein by reference in its entirety.

Exemplary enzymes useful in the amplification or modification of nucleic acid ligands are set forth in Table 2.

TABLE 2

POLYMERASES AND REVERSE TRANSCRIPTASES

Thermostable DNA Polymerases:

OnmiBase ™ Sequencing Enzyme
Pfu DNA Polymerase
Taq DNA Polymerase
Taq DNA Polymerase, Sequencing Grade
TaqBead ™ Hot Start Polymerase
AmpliTaq Gold
Tfl DNA Polymerase
Tli DNA Polymerase
Tth DNA Polymerase

TABLE 2-continued

POLYMERASES AND REVERSE TRANSCRIPTASES

DNA POLYMERASES:

DNA Polymerase I, Klenow Fragment, Exonuclease Minus
DNA Polymerase I
DNA Polymerase I Large (Klenow) Fragment
Terminal Deoxynucleotidyl Transferase
T4 DNA Polymerase
Reverse Transcriptases:

AMV Reverse Transcriptase
M-MLV Reverse Transcriptase

For certain embodiments, it may be desirable to incorporate a label into nucleic acid ligands, amplification products, probes or primers. A number of different labels may be used, such as fluorophores, chromophores, radio-isotopes, enzymatic tags, antibodies, chemiluminescent, electroluminescent, affinity labels, etc. One of skill in the art will recognize that these and other label moieties not mentioned herein can be used in the practice of the present invention.

Examples of affinity labels include an antibody, an antibody fragment, a receptor protein, a hormone, biotin, DNP, and any polypeptide/protein molecule that binds to an affinity label.

Examples of enzymatic tags include urease, alkaline phosphatase or peroxidase. Colorimetric indicator substrates can be employed with such enzymes to provide a detection means visible to the human eye or spectrophotometrically.

The following fluorophores are contemplated to be useful in practicing the present invention. Alexa 350, Alexa 430, AMCA, BODIPY 630/650, BODIPY 650/665, BODIPY-FL, BODIPY-R6G, BODIPY-TMR, BODIPY-TRX, Cascade Blue, Cy2, Cy3, Cy5,6-FAM, Fluorescein, HEX, 6-JOE, Oregon Green 488, Oregon Green 500, Oregon Green 514, Pacific Blue, REG, Rhodamine Green, Rhodamine Red, ROX, TAMRA, TET, Tetramethylrhodamine, and Texas Red.

Methods of Immobilization

In various embodiments, the nucleic acid ligands of the present invention may be attached to a solid surface ("immobilized"). In a preferred embodiment, immobilization may occur by attachment of DALM to a solid surface, such as a magnetic bead, a plastic microtiter plate or a glass slide. Nucleic acid ligands may be attached to the DALM by electrostatic interaction with magnesium ion (FIG. 4). This system is advantageous in that the attachment of nucleic acid ligand to DALM may be readily reversed by addition of a magnesium chelator, such as EDTA.

Immobilization of nucleic acid ligands may alternatively be achieved by a variety of methods involving either non-covalent or covalent interactions between the immobilized nucleic acid ligand, comprising an anchorable moiety, and an anchor. In an exemplary embodiment, immobilization may be achieved by coating a solid surface with streptavidin or avidin and the subsequent attachment of a biotinylated polynucleotide (Holmstrom, 1993). Immobilization may also occur by coating a polystyrene or glass solid surface with poly-L-Lys or poly L-Lys, Phe, followed by covalent attachment of either amino- or sulfhydryl-modified polynucleotides, using bifunctional crosslinking reagents (Running, 1990; Newton, 1993).

Immobilization may take place by direct covalent attachment of short, 5'-phosphorylated primers to chemically modified polystyrene plates ("Covalink" plates, Nunc) Rasmussen, (1991). The covalent bond between the modified oligonucleotide and the solid phase surface is formed by condensation with a water-soluble carbodiimide. This method facilitates a predominantly 5'-attachment of the oligonucleotides via their 5'-phosphates.

Nikiforov et al. (U.S. Pat. No. 5,610,287 incorporated herein by reference) describes a method of non-covalently immobilizing nucleic acid ligand molecules in the presence of a salt or cationic detergent on a hydrophilic polystyrene solid support containing an —OH, —C=O or —COOH hydrophilic group or on a glass solid support. The support is contacted with a solution having a pH of about 6 to about 8 containing the nucleic acid ligand and the cationic detergent or salt. The support containing the immobilized nucleic acid ligand may be washed with an aqueous solution containing a non-ionic detergent without removing the attached molecules.

Another commercially available method for immobilization is the "Reacti-Bind™ DNA Coating Solutions" (see "Instructions—Reacti-Bind™ DNA Coating Solution" 1/1997). This product comprises a solution that is mixed with DNA and applied to surfaces such as polystyrene or polypropylene. After overnight incubation, the solution is removed, the surface washed with buffer and dried, after which it is ready for hybridization. It is envisioned that similar products, i.e. Costar "DNA-BIND™" or Immobilon-AV Affinity Membrane (IAV, Millipore, Bedford, Mass.) may be used in the practice of the instant invention.

Separation and Quantitation Methods

It may be desirable to separate nucleic acid ligands of different lengths for the purpose of quantitation, analysis or purification.

Gel Electrophoresis

In one embodiment, amplification products are separated by agarose, agarose-acrylamide or polyacrylamide gel electrophoresis using standard methods (Sambrook et al., 1989).

Separation by electrophoresis is based upon the differential migration through a gel according to the size and ionic charge of the molecules in an electrical field. High resolution techniques normally use a gel support for the fluid phase. Examples of gels used are starch, acrylamide, agarose or mixtures of acrylamide and agarose. Frictional resistance produced by the support causes size, rather than charge alone, to become the major determinant of separation. Smaller molecules with a more negative charge will travel faster and further through the gel toward the anode of an electrophoretic cell when high voltage is applied. Similar molecules will group on the gel. They may be visualized by staining and quantitated, in relative terms, using densitometers which continuously monitor the photometric density of the resulting stain. The electrolyte may be continuous (a single buffer) or discontinuous, where a sample is stacked by means of a buffer discontinuity, before it enters the running gel/running buffer. The gel may be a single concentration or gradient in which pore size decreases with migration distance. In SDS gel electrophoresis of proteins or electrophoresis of polynucleotides, mobility depends primarily on size and is used to determined molecular weight. In pulse field electrophoresis, two fields are applied alternately at right angles to each other to minimize diffusion mediated spread of large linear polymers.

Agarose gel electrophoresis facilitates the separation of DNA or RNA based upon size in a matrix composed of a highly purified form of agar. Nucleic acids tend to become oriented in an end on position in the presence of an electric field. Migration through the gel matrices occurs at a rate inversely proportional to the $\log_{10}$ of the number of base pairs (Sambrook et al., 1989).

Polyacrylamide gel electrophoresis (PAGE) is an analytical and separative technique in which molecules are separated by their different electrophoretic mobilities in a hydrated gel. The gel suppresses convective mixing of the fluid phase through which the electrophoresis takes place and contributes molecular sieving.

Chromatographic Techniques

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder, 1982). In yet another alternative, labeled cDNA products, such as biotin or antigen can be captured with beads bearing avidin or antibody, respectively.

Microfluidic Techniques

Microfluidic techniques include separation on a platform such as microcapillaries, designed by ACLARA Bio-Sciences Inc., or the LabChip™ liquid integrated circuits made by Caliper Technologies Inc. These microfluidic platforms require only nanoliter volumes of sample, in contrast to the microliter volumes required by other separation technologies. Miniaturizing some of the processes involved in genetic analysis has been achieved using microfluidic devices. For example, published PCT Application No. WO 94/05414, to Northrup and White, incorporated herein by reference, reports an integrated micro-PCR™ apparatus for collection and amplification of nucleic acids from a specimen. U.S. Pat. Nos. 5,304,487 to Wilding et al., and U.S. Pat. No. 5,296,375 to Kricka et al., discuss devices for collection and analysis of cell containing samples and are incorporated herein by reference. U.S. Pat. No. 5,856,174 describes an apparatus which combines the various processing and analytical operations involved in nucleic acid analysis and is incorporated herein by reference.

Capillary Electrophoresis

In some embodiments, it may be desirable to provide an additional, or alternative means for analyzing nucleic acid ligands. In these embodiment, microcapillary arrays are contemplated to be used for the analysis.

Microcapillary array electrophoresis generally involves the use of a thin capillary or channel that may or may not be filled with a particular separation medium. Electrophoresis of a sample through the capillary provides a size based separation profile for the sample. The use of microcapillary electrophoresis in size separation of nucleic acids has been reported in, e.g., Woolley and Mathies, 1994. Microcapillary array electrophoresis generally provides a rapid method for size-based sequencing, PCRTM product analysis and restriction fragment sizing. The high surface to volume ratio of these capillaries allows for the application of higher electric fields across the capillary without substantial thermal variation across the capillary, consequently allowing for more rapid separations. Furthermore, when combined with confocal imaging methods, these methods provide sensitivity in the range of attomoles, which is comparable to the sensitivity of radioactive sequencing methods. Microfabrication of microfluidic devices including microcapillary electrophoretic devices has been discussed in detail in, e.g., Jacobsen et al., 1994; Effenhauser et al., 1994; Harrison et al., 1993; Effenhauser et al., 1993; Manz et al., 1992; and U.S. Pat. No. 5,904,824, incorporated herein by reference. Typically, these methods comprise photolithographic etching of micron scale channels on silica, silicon or other crystalline substrates or chips, and can be readily adapted for use in the present invention. In some embodiments, the capillary arrays may be fabricated from the same polymeric materials described for the fabrication of the body of the device, using injection molding techniques.

Tsuda et al., 1990, describes rectangular capillaries, an alternative to the cylindrical capillary glass tubes. Some advantages of these systems are their efficient heat dissipation due to the large height-to-width ratio and, hence, their high surface-to-volume ratio and their high detection sensitivity for optical on-column detection modes. These flat separation channels have the ability to perform two-dimensional separations, with one force being applied across the separation channel, and with the sample zones detected by the use of a multi-channel array detector.

In many capillary electrophoresis methods, the capillaries, e.g., fused silica capillaries or channels etched, machined or molded into planar substrates, are filled with an appropriate separation/sieving matrix. Typically, a variety of sieving matrices are known in the art may be used in the microcapillary arrays. Examples of such matrices include, e.g., hydroxyethyl cellulose, polyacrylamide, agarose and the like. Generally, the specific gel matrix, running buffers and running conditions are selected to maximize the separation characteristics of the particular application, e.g., the size of the nucleic acid fragments, the required resolution, and the presence of native or undenatured nucleic acid molecules. For example, running buffers may include denaturants, chaotropic agents such as urea or the like, to denature nucleic acid ligands in the sample.

DALM

In preferred embodiments, DALM is used to attach nucleic acid ligands to a surface and/or to promote photochemical detection of binding of analyte to nucleic acid ligand. Production and use of diazoluminomelanin (DALM) has previously been described in U.S. Pat. Nos. 5,856,108 and 5,003,050, incorporated herein by reference. DALM is prepared by reacting 3AT (3-amino-L-tyrosine) with an alkali metal nitrite, such as sodium nitrite, and thereafter reacting the resulting diazotized product with luminol. At some point in the reaction, the alaninyl portion of the 3AT rearranges to provide the hydroxyindole portion of the final product. It is believed that such rearrangement occurs following coupling of the luminol to the diazotized 3AT.

The reaction between 3AT and the alkali metal nitrite is carried out in aqueous medium. Since diazotization reactions are, in general, exothermic, it may be desirable to carry out this reaction under isothermal conditions or at a reduced temperature, such as, for example, at ice bath temperatures. The reaction time for the diazotization can range from about 1 to 20 minutes, preferably about 5 to 10 minutes.

Because of the relative insolubility of luminol in aqueous medium, the luminol is dissolved in an aprotic solvent, such as dimethylsulfoxide (DMSO), then added, with stirring, to the aqueous solution of diazotized 3AT. This reaction is carried out, at reduced temperature, for about 20 to 200 minutes. The solvent is then removed by evaporation at low pressure, with moderate heating, e.g., about 30° to 37° C.

The reaction mixture is acidic, having a pH of about 3.5. The coupling of the luminol and the diazotized 3AT can be facilitated by adjusting the pH of the reaction mixture to about 5.0 to 6.0.

The product DALM may be precipitated from the reaction mixture by combining the reaction mixture with an excess of a material that is not a solvent for the DALM, e.g., acetone. After centrifuging the precipitate and discarding the supernatant, the solid material may be dried under vacuum.

In general, the quantities of the 3AT, alkali metal nitrite and luminol reactants are equimolar. It is, however, within the scope of the invention to vary the quantities of the reactants. The molar ratio of 3AT:luminol may be varied over the range of about 0.6:1 to 3:1.

DALM is water soluble, having an apparent pKa for solubility about pH 5.0. DALM does not require a catalyst for chemiluminescence. The duration of the reaction is in excess of 52 hours. In contrast, luminol requires a catalyst; with micro peroxidase as the catalyst, luminol has shown peak luminescence at 1 sec and half-lives of light emission of 0.5 and 4.5 sec at pH 8.6 and 12.6, respectively. The chemiluminescence yield of DALM is better at pH 7.4 than at pH 9.5, although it still provides a strong signal at strongly basic pHs. DALM also produces chemiluminescence at pH 6.5 which is about the same intensity as that produced at pH 9.5.

DALM can be used for chemiluminescent immunoassays for biological and chemical agents; in radiofrequency and ionizing radiation dosimeters; and for RNA/DNA hybridization assays for viruses and genetic detection.

Aptamers

In certain preferred embodiments, the nucleic acid ligands to be used in the practice of the invention are aptamers. Methods of constructing and determining the binding characteristics of aptamers are well known in the art. For example, such techniques are described in Lorsch and Szostak (1996) and in U.S. Pat. Nos. 5,582,981, 5,595,877 and 5,637,459, each incorporated herein by reference.

Aptamers may be prepared by any known method, including synthetic, recombinant, and purification methods, and may be used alone or in combination with other aptamers specific for the same target. Further, the term "aptamer" specifically includes "secondary aptamers" containing a consensus sequence derived from comparing two or more known aptamers that bind to a given target.

In general, a minimum of approximately 3 nucleotides, preferably at least 5 nucleotides, are necessary to effect specific binding. The only apparent limitations on the binding specificity of the target/nucleic acid ligand complexes of the invention concern sufficient sequence to be distinctive in the binding nucleic acid ligand and sufficient binding capacity of the target substance to obtain the necessary interaction. Oligonucleotides of sequences shorter than 10 bases may be feasible if the appropriate interaction can be obtained in the context of the environment in which the target is placed. Although the nucleic acid ligands described herein are single-stranded or double-stranded, it is contemplated that aptamers may sometimes assume triple-stranded or quadruple-stranded structures.

The specifically binding nucleic acid ligands need to contain the sequence that confers binding specificity, but may be extended with flanking regions and otherwise derivatized. In preferred embodiments of the invention, aptamer binding sites will be flanked by known, amplifiable sequences, facilitating the amplification of the nucleic acid ligands by PCR or other amplification techniques. In a further embodiment, the flanking sequence may comprise a specific sequence that preferentially recognizes or binds a moiety to enhance the immobilization of the aptamer to a substrate.

The nucleic acid ligands found to bind to the targets may be isolated, sequenced, and/or amplified or synthesized as conventional DNA or RNA molecules. Alternatively, nucleic acid ligands of interest may comprise modified oligomers. Any of the hydroxyl groups ordinarily present in nucleic acid ligands may be replaced by phosphonate groups, phosphate groups, protected by a standard protecting group, or activated to prepare additional linkages to other nucleotides, or may be conjugated to solid supports. The 5' terminal OH is conventionally free but may be phosphorylated. Hydroxyl group substituents at the 3' terminus may also be phosphorylated. The hydroxyls may be derivatized by standard protecting groups. One or more phosphodiester linkages may be replaced by alternative linking groups. These alternative linking groups include, exemplary embodiments wherein P(O)O is replaced by P(O)S, P(O)NR$_2$, P(O)R, P(O)OR', CO, or CNR$_2$, wherein R is H or alkyl (1–20C) and R' is alkyl (1–20C); in addition, this group may be attached to adjacent nucleotides through O or S. Not all linkages in an oligomer need to be identical.

The nucleic acid ligands used as starting materials in the process of the invention to determine specific binding sequences may be single-stranded or double-stranded DNA or RNA. In a preferred embodiment, the sequences are single-stranded DNA. The use of DNA eliminates the need for conversion of RNA aptamers to DNA by reverse transcriptase prior to PCR amplification. Furthermore, DNA is less susceptible to nuclease degradation than RNA. In preferred embodiments, the starting nucleic acid ligand will contain a randomized sequence portion, generally including from about 10 to 400 nucleotides, more preferably 20 to 100 nucleotides. The randomized sequence is flanked by primer sequences that permit the amplification of nucleic acid ligands found to bind to the analyte. The flanking sequences may also contain other convenient features, such as restriction sites. These primer hybridization regions generally contain 10 to 30, more preferably 15 to 25, and most preferably 18 to 20, bases of known sequence.

Both the randomized portion and the primer hybridization regions of the initial oligomer population are preferably constructed using conventional solid phase techniques. Such techniques are well known in the art, such methods being described, for example, in Froehler, et al., (1986a, 1986b, 1988, 1987). Nucleic acid ligands may also be synthesized using solution phase methods such as triester synthesis, known in the art. For synthesis of the randomized regions, mixtures of nucleotides at the positions where randomization is desired are added during synthesis.

Any degree of randomization may be employed. Some positions may be randomized by mixtures of only two or three bases rather than the conventional four. Randomized positions may alternate with those which have been specified. Indeed, it is helpful if some portions of the candidate randomized sequence are in fact known.

SELEX Technology

A preferred method of selecting for nucleic acid ligand specificity involves the SELEX process. The SELEX process is described in U.S. Pat. No. 5,475,096, and U.S. Pat. No. 5,270,163, (see also WO91/19813), which are each specifically incorporated by reference.

The SELEX method involves selection from a mixture of candidate nucleic acid ligands and step-wise iterations of binding, partitioning and amplification, using the same general selection scheme, to achieve virtually any desired criterion of binding affinity and selectivity. Starting from a mixture of nucleic acid ligands, preferably comprising a segment of randomized sequence, the method includes the following steps. Contacting the mixture with the target under conditions favorable for binding. Partitioning unbound nucleic acid ligands from those nucleic acid ligands that have bound specifically to target analyte. Dissociating the nucleic acid ligand-analyte complexes. Amplifying the nucleic acid ligands dissociated from the nucleic acid ligand-analyte complexes to yield mixture of nucleic acid ligands that preferentially bind to the analyte. Reiterating the steps of binding, partitioning, dissociating and amplifying through as many cycles as desired to yield highly specific, nucleic acid ligands that bind with high affinity to the target analyte.

In the SELEX process, a candidate mixture of nucleic acid ligands of differing sequence is prepared. The candidate mixture generally includes regions of fixed sequences (i.e., each of the nucleic acid ligands contains the same sequences) and regions of randomized sequences. The fixed sequence regions are selected to: (a) assist in the amplification steps; (b) mimic a sequence known to bind to the target; or (c) promote the formation of a given structural arrangement of the nucleic acid ligands. The randomized sequences may be totally randomized (i.e., the probability of finding a given base at any position being one in four) or only partially randomized (i.e., the probability of finding a given base at any location can be any level between 0 and 100 percent).

The candidate mixture is contacted with the selected analyte under conditions favorable for binding of analyte to nucleic acid ligand. The interaction between the target and the nucleic acid ligands can be considered as forming nucleic acid ligand-target pairs with those nucleic acid ligands having the highest affinity for the analyte.

The nucleic acid ligands with the highest affinity for the analyte are partitioned from those nucleic acid ligands with lesser affinity. Because only a small number of sequences (possibly only one molecule of nucleic acid ligand) corresponding to the highest affinity nucleic acid ligands exist in the mixture, it is generally desirable to set the partitioning criteria so that a significant amount of nucleic acid ligands in the mixture (approximately 5–50%) are retained during partitioning.

Those nucleic acid ligands selected during partitioning as having higher affinity for the target are amplified to create a new candidate mixture that is enriched in higher affinity nucleic acid ligands.

By repeating the partitioning and amplifying steps, each round of candidate mixture contains fewer and fewer weakly binding sequences. The average degree of affinity of the nucleic acid ligands to the target will generally increase with each cycle. The SELEX process can ultimately yield a mixture containing one or a small number of nucleic acid ligands having the highest affinity for the target analyte.

Nucleic acid ligands produced for SELEX may be generated on a commercially available DNA synthesizer. The random region is produced by mixing equimolar amounts of each nitrogenous base (A,C,G, and T) at each position to create a large number of permutations (i.e., $4^n$, where "n" is the oligo chain length) in a very short segment. Thus a randomized 40 mer (40 bases long) would consist of $4^{30}$ or maximally $10^{24}$ different nucleic acid ligands. This provides dramatically more possibilities to find high affinity nucleic acid ligands when compared to the $10^9$ to $10^{11}$ variants of murine antibodies produced by a single mouse. The random region is flanked by two short Polymerase Chain Reaction (PCR) primer regions to enable amplification of the small subset of nucleic acid ligands that bind tightly to the target analyte.

Another advantage of DNA-based binding is that simple heating to $\geq 94°$ C. can drive off the bound analyte (i.e., BW agent or "antigen"). Two potential technical hurdles associated with SELEX might be: 1) there are potential electrostatic repulsions between the negatively charged phosphate backbone of the nucleic acid ligands and negatively charged target molecules, but this has not been a significant problem in other recognized SELEX work, and 2) cloning, which is necessary to obtain the DNA sequence of each high affinity binding nucleic acid ligand. One final consideration is that many RNA nucleic acids have performed well due to their propensity to form secondary and tertiary structure "binding pockets", but RNAses abound in nature making RNA nucleic acids less desirable for field use. Fortunately, many single and double stranded DNA nucleic acid ligands have also demonstrated specificity and high affinity binding to their intended targets.

Nucleic Acid Chips and Aptamer Arrays

Nucleic acid chips and aptamer array technology provide a means of rapidly screening analytes for their ability to hybridize to a potentially large number of single stranded nucleic acid ligand probes immobilized on a solid substrate. In preferred embodiments, the nucleic acid ligands are DNA. Specifically contemplated are chip-based DNA technologies such as those described by Hacia et al., 1996 and Shoemaker et al., 1996. These techniques involve quantitative methods for analyzing large numbers of samples rapidly and accurately. The technology capitalizes on the binding properties of single stranded DNA to screen samples. (Pease et al., 1994; Fodor et al., 1993; Southern et al., 1994; Travis, 1997; Lipshutz et al., 1995; Matson et al., 1995; each of which is incorporated herein by reference.)

A nucleic acid ligand chip or array consists of a solid substrate upon which an array of single stranded nucleic acid ligand molecules have been attached. For screening, the chip or array is contacted with a sample containing analyte which is allowed to bind. The degree of stringency of binding may be manipulated as desired by varying, for example, salt concentration, temperature, pH and detergent content of the medium. The chip or array is then scanned to determine which nucleic acid ligands have bound to the analyte. Prior to the present invention, DNA chips were typically used to bind to target DNA or RNA molecules in a sample.

A variety of DNA chip formats are described in the art, for example U.S. Pat. Nos. 5,861,242 and 5,578,832 which are expressly incorporated herein by reference. The structure of a nucleic acid ligand chip or array comprises: (1) an excitation source; (2) an array of probes; (3) a sampling element; (4) a detector; and (5) a signal amplification/treatment system. A chip may also include a support for immobilizing the probe.

In particular embodiments, a nucleic acid ligand may be tagged or labeled with a substance that emits a detectable signal, for example, DALM. The tagged or labeled species may be fluorescent, phosphorescent, or luminescent, or it may emit Raman energy or it may absorb energy. When the nucleic acid ligand binds to a targeted analyte, a signal is generated that is detected by the chip. The signal may then be processed in several ways, depending on the nature of the signal.

The nucleic acid ligand may be immobilized onto an integrated microchip that also supports a phototransducer and related detection circuitry. Alternatively, a nucleic acid ligand may be immobilized onto a membrane or filter which is then attached to the microchip or to the detector surface itself.

The nucleic acid ligands may be directly or indirectly immobilized onto a transducer detection surface to ensure optimal contact and maximum detection. The ability to directly synthesize on or attach polynucleotide probes to solid substrates is well known in the art. See U.S. Pat. Nos. 5,837,832 and 5,837,860 both of which are expressly incorporated by reference. A variety of methods have been utilized to either permanently or removably attach the nucleic acid ligands to the substrate. Exemplary methods are described above under the section on immobilization. When immobilized onto a substrate, the nucleic acid ligands are stabilized and may be used repeatedly.

Exemplary substrates include nitrocellulose, nylon membrane or glass. Numerous other matrix materials may be used, including reinforced nitrocellulose membrane, activated quartz, activated glass, polyvinylidene difluoride (PVDF) membrane, polystyrene substrates, polyacrylamide-based substrate, other polymers such as poly(vinyl chloride), poly(methyl methacrylate), poly(dimethyl siloxane) and photopolymers which contain photoreactive species such as nitrenes, carbenes and ketyl radicals capable of forming covalent links with target molecules (U.S. Pat. Nos. 5,405,766 and 5,986,076, each incorporated herein by reference).

Binding of nucleic acid ligand to a selected support may be accomplished by any of several means. For example, DNA is commonly bound to glass by first silanizing the glass surface, then activating with carbodiimide or glutaraldehyde. Alternative procedures may use reagents such as 3-glycidoxypropyltrimethoxysilane (GOP) or aminopropyltrimethoxysilane (APTS) with DNA linked via amino linkers incorporated either at the 3' or 5' end of the molecule during DNA synthesis. DNA may be bound directly to membranes using ultraviolet radiation. With nitrocellulose membranes, the DNA probes are spotted onto the membranes. A UV light source (Stratalinker, from Stratagene, La Jolla, Calif.) is used to irradiate DNA spots and induce cross-linking. An alternative method for cross-linking involves baking the spotted membranes at 80° C. for two hours in vacuum. Further, it is specifically contemplated that the nucleic acid ligand may be bound to an immobilized indicator species. Therefore, in a preferred embodiment of the invention, DALM is immobilized to a solid substrate and the nucleic acid ligands attached to the immobilized DALM. Alternatively, the DALM/nucleic acid ligand complex may be bound via the DALM or the polynucleotide to the substrate.

Specific nucleic acid ligands may first be immobilized onto a membrane and then attached to a membrane in contact with a transducer detection surface. This method avoids binding the nucleic acid ligand onto the transducer and may be desirable for large-scale production. Membranes particularly suitable for this application include nitrocellulose membrane (e.g., from BioRad, Hercules, Calif.) or polyvinylidene difluoride (PVDF) (BioRad, Hercules, Calif.) or nylon membrane (Zeta-Probe, BioRad) or polystyrene base substrates (DNA.BIND™ Costar, Cambridge, Mass.).

CIE Analysis

Colorimetric analysis of a visible light signal (or signature) from an array of recognition complexes may be performed by CIE analysis. This refers to the standard curves for transformation of a spectral power distribution (SPD) into a set of three numbers that specifies a color, adopted in 1931 by the Commission Internationale de L'Eclairage (CIE). The CIE system determines how to convert an SPD into a set of three numerical components (tristimulus values) that are the equivalent of coordinates in 3-dimensional color space. By generating a unique set of coordinates from a array spectral emission, CIE analysis may be used to provide a "signature" for a target analyte. A discussion of CIE 1931 standards and calculation of tristimulus values may be found at the internet site http://kiptron.psyc.virginia.edu/steve_boker/ColorVision2/ColorVision2. htm1.

Figure 19:
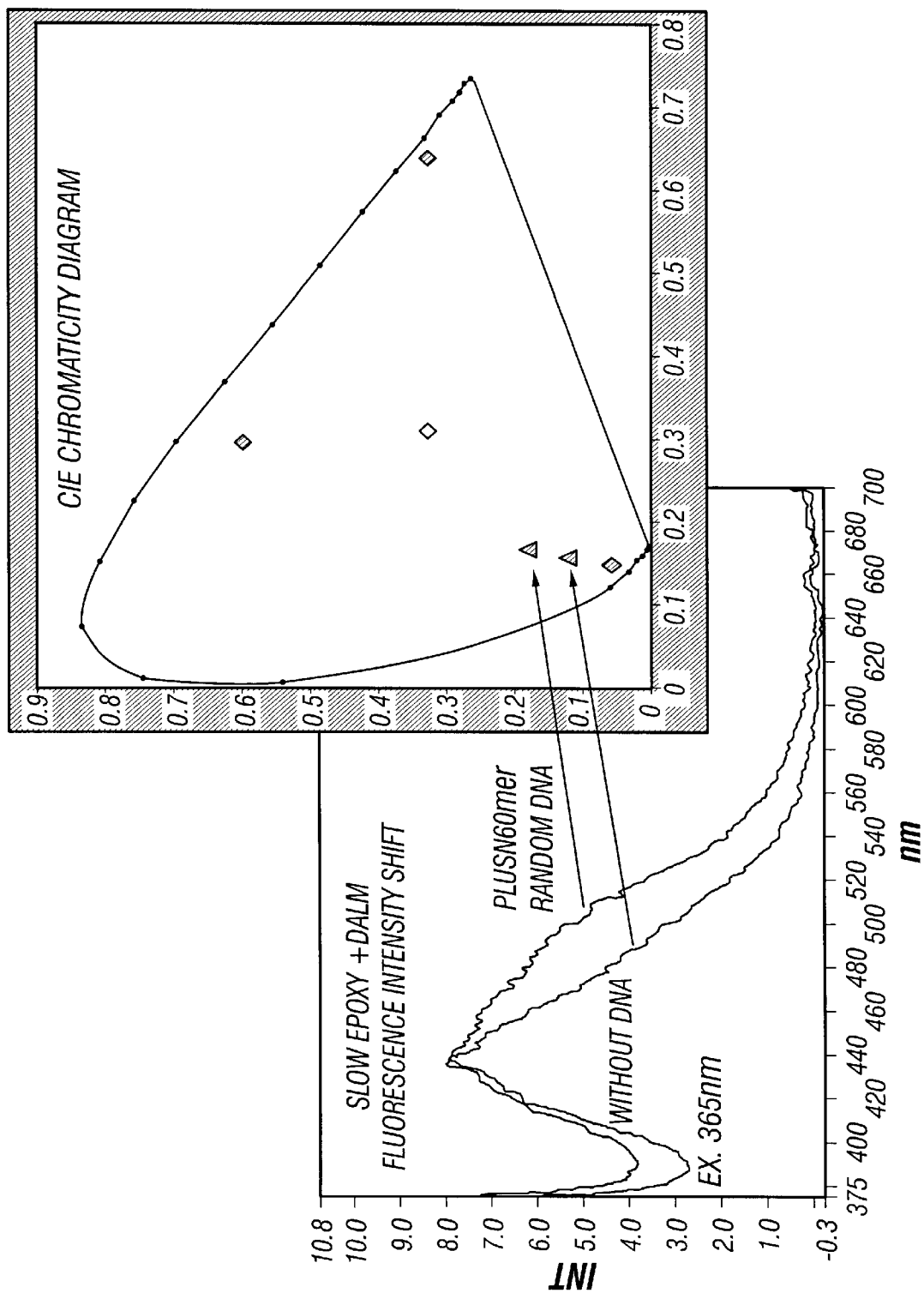

The CIE 1931 standards were based on the work of Wright (1928) and Guild (1931). Guild transformed his and Wright's data into a 3-dimensional coordinate system, with the dimensions corresponding to red (X), green (Y) and blue (Z). If it is assumed that X+Y+Z=1, then Z=1−X−Y, allowing a two-dimensional plot of CIE color space using just the X and Y (two number) coordinates, as illustrated in FIG. 19.

CIE colorimetry tables may be accessed at internet site http://www.hike.te.chiba.u.ac.jp/ikeda/CIE/table/intro.html. They have been published as ISO/CIE 10526–1991, Colorimetric illuminants and ISO/CIE 10527–1991, Colorimetric observers. They may be obtained from the CIE Central Bureau, Kegelgasse 27, A-1030 Vienna, Austria.

Determination of CIE values, analysis of data and the use of neural networks and lookup tables is discussed in U.S. Pat. Nos. 5,376,963; 5,424,545; 5,446,543; 5,818,044; 5,867,265; 6,028,311; 6,043,909; and 6,072,464, the entire text of each of which is incorporated herein by reference.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1
DNA Based Recognition Complex System
Methods and Materials

All oligonucleotides were obtained from Ransom Hill Biosciences, Sigma Chemical Co., or Genosys Corp. The BACA1FI and BACA6RI gene probes were synthesized from published sequences (Reif et al, 1994) for portions of the capsular antigen gene of virulent strains of *Bacillus anthracis*. Precast 4–20% gradient and 10% homogenous polyacrylamide gels made with Tris-Borate-EDTA (TBE) buffer as well as DNA ladder (Amplisize; 50–2,000 bp) standards were run on a mini Protean II electrophoresis system (BioRad). DALM was biosynthesized in *Escherichia coli* strain JM109 bacteria and partially purified as described in Bruno et al., 1998. All polymerase chain reaction (PCR) reagents, including dideoxynucleotides, were from a "Silver Sequence" kit, and SELEX binding buffer (BB) was composed of 0.5M NaCl, 10 mM Tris-HCl, and 1 mM $MgCl_2$ in deionized water (pH 7.5 to 7.6; Bruno, 1997).

Two types of arrays of nucleic acid ligands were generated: 1) a naturally occurring overlapping random (N) 60 mer; and 2) a contiguous or ligated array. In the latter array, nucleic acid ligand diversity was increased, compared to the starting random 60 mers, by truncating longer chains with the addition of dideoxynuclotides during a PCR step and covalently linking non-contiguous DNA chains together with Taq DNA ligase.

The PCR chain termination step involved addition of 6.6 $\mu$g of random (N) 60 mer as a self-priming (due to partial hybridization) PCR template with 8 $\mu$l of each deoxy/dideoxynucleotide (i.e., d/ddA, d/ddC, d/ddG, d/ddT) and 20 $\mu$l (80 units) of Taq polymerase per tube. The tubes were PCR amplified using the following temperature profile: 96° C. for 5 min, followed by 40 cycles of 96° C. for 1 min, 25° C. for 1 min, and 72° C. for 1 min. PCR extension was completed at 72° C. for 7 min and tubes were stored at 4 to 6° C. until electrophoresed. The collection of nucleic acid ligand species present as overlapping random (N) 60 mers or as ligated and truncated DNAs constituted a library of nucleic acid ligands.

For both types of DNA arrays, 3.3 μg (typically 5 to 10 μl) of library DNA was diluted with 2× loading buffer and loaded into each well of precast 10% or 4–20% gradient mini TBE polyacrylamide gels and electrophoresed in cold 1× TBE for 1 h at 100 V per gel. If DNA was to be visualized in the gel, gels were stained with 0.5 μg/ml ethidium bromide in TBE for 10 min, followed by rinsing in deionized water for 30 min and photography on a 300 nm ultraviolet transilluminator using Polaroid type 667 film.

Arrays of nucleic acid ligands were generated from library DNA separated by electrophoresis (size and charge). Analyte binding and nucleic acid hybridization to the nucleic acid ligand arrays were assayed as follows:

Gels were cut into strips containing the one-dimensional DNA arrays of either type and were added to 10 ml of BB. Gel strips were allowed to equilibrate in their respective buffers for 10 min at room temperature (RT) with gentle shaking and were then scanned as described below prior to addition of analytes. All DNA analytes were added at a final concentration of 5 μg/ml and all protein analytes were added at a final concentration of 10 μg/ml in BB for 1 h at RT with gentle shaking. Gels were gently rinsed twice in 10 ml of BB, carefully repositioned and rescanned on a luminescence spectrometer.

To compare the fluorescence emission spectrum of DALM in the presence or absence of DNA, 50 μl drops of slow hardening epoxy resin were placed in black microtiter plate wells and overlaid with 50 μl of undiluted bacterial DALM. The DALM and epoxy were incubated in a covered plate for three to four days at ambient temperature. Excess DALM was removed by five washes with 200 μl of deionized water. All fluid was decanted and emission spectra was acquired before and after the addition of 50 μl (30 μg) of random 60 mer DNA.

A Perkin-Elmer (Beaconsfield, Buckinghamshire, UK) model LS 50B luminescence spectrometer equipped with a plate reader was used in the thin layer chromatography (TLC) plate mode to scan nucleic acid ligand arrays in gel slices before and after addition of various analytes. After minor swelling or shrinkage in each of the reaction buffers, gel strips were generally 95 to 96 mm in length, with the DNA array being contained in the lowermost 65 mm of each gel strip. Gel strips were scanned with an excitation of 260 nm (10 nm slits), emission of 420 nm (10 nm slits) and 1 mm resolution (i.e., scanned in 1 mm increments). In some cases, DALM and random 60 mer DNA were scanned separately and in combination using an excitation wavelength of 360 nm (excitation maximum for DALM).

An alternative method for attaching an array of recognition complexes to glass or other solid surfaces was developed. In this method, DALM was attached directly to a glass slide. Nucleic acid ligands can be attached to DALM using magnesium ion binding as shown in FIG. 4, or by covalent or other attachment techniques discussed above. Glass slides were cleaned with alcoholic potassium hydroxide, washed with DI (deionized water) and dried overnight. To approximately 150 ml of acetone was added 8 ml of water and 12 ml of 3-aminopropyltriethoxysilane. Acetone was added to a final volume of 200 ml. The slides were placed on the bottom of a rectangular plastic storage container and the acetone solution was poured over them. After two hours at room temperature on an orbital shaker (75 rpm) the slides were washed twice with acetone.

The presence of amino groups on the surface of the glass was examined. To 20 ml of saturated sodium borate, 5 ml of 5% w/v 2,4,6-trinitrobenzenesulfonate was added. Slides were placed in the solution and incubated at 37° C. for 2 hours, then rinsed with DI. The presence of amino groups was indicated by a yellow color.

DALM was covalently attached to the amino groups on the surface of the glass. Reduced synthetic DALM (55.2 mg) was dissolved in 2 to 3 ml of 0.1 M NaOH. 0.1 M MOPS buffer (pH 7) was added to a final volume of 50 ml. The DALM solution was poured over the glass slides in the storage container. Additional MOPS buffer was added until all slides were completely covered. EDC (N,N-(3-dimethylaminopropyl)-N'-ethyl-carbodiimide hydrochloride, 130 mg) was dissolved in MOPS buffer and immediately added to the slides, while shaking on an orbital shaker. This addition was repeated every 15 min for an additional four times. After another hour, 200 mg of EDC was added. The slides were incubated at room temperature for another two hours with shaking, then rinsed and dried overnight. DALM was covalently attached to the glass slides. Although glass was used in this example, the skilled artisan will realize that any solid surface capable of being coated with 3-aminopropyltriethoxysilane could be used in the practice of the invention.

Results

Gel electrophoresis of random DNA libraries showed that a high degree of partial hybridization occurs between members of the library, leading to an aggregated collection of hybrids that appear as a smear on electrophoretic gels (data not shown). The electrophoretic migration of the array varied slightly from lane to lane in the gel.

Figure 9A:
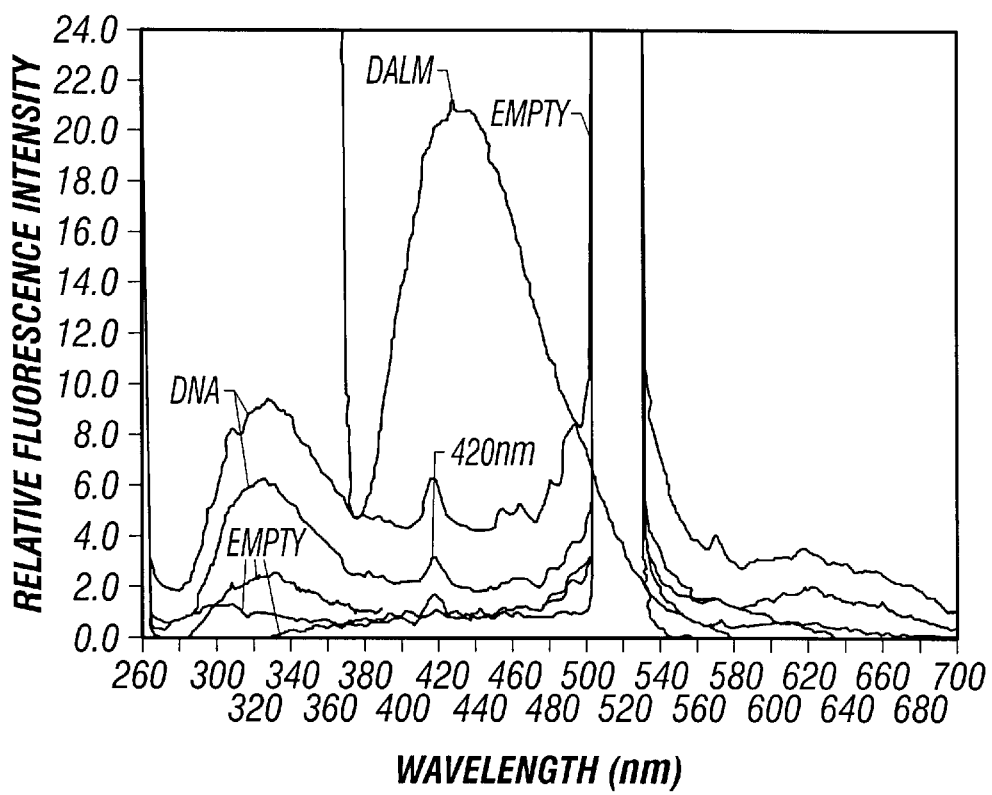

Fluorescence emission of the nucleic acid ligand arrays with or without bound analyte was scanned using a 260 nm excitation to compare baseline fluorescence of the empty TLC plate reader, random N60 mer DNA in a gradient polyacrylamide gel (scanned at a locus with high DNA concentration), and bacterial DALM. FIG. 9A illustrates a comparison of emission spectra at 260 nm excitation for empty 10% polyacrylamide gels versus random 60 mer DNA following electrophoresis in 10% polyacrylamide gels (at loci in the gels rich in DNA), and bacterial diazoluminomelanin (DALM).

Random DNA in a polyacrylamide gel excited at 260 nm returned most of its energy in the ultraviolet region of the spectrum (FIG. 9A). DALM excited at 260 nm yields extensive fluorescence in the blue region of the spectrum (FIG. 9A). Emission wavelengths in the visible region of DALM's emission spectrum that augment the minor visible DNA emission peaks are most desirable for detection of analyte binding. A less prominent emission peak (420 nm) was selected for further analysis. Use of this excitation wavelength also avoided the high background fluorescence from DALM and the TLC plate reader observed between 265 to 370 nm and 500 to 540 nm, respectively.

Figure 9B:
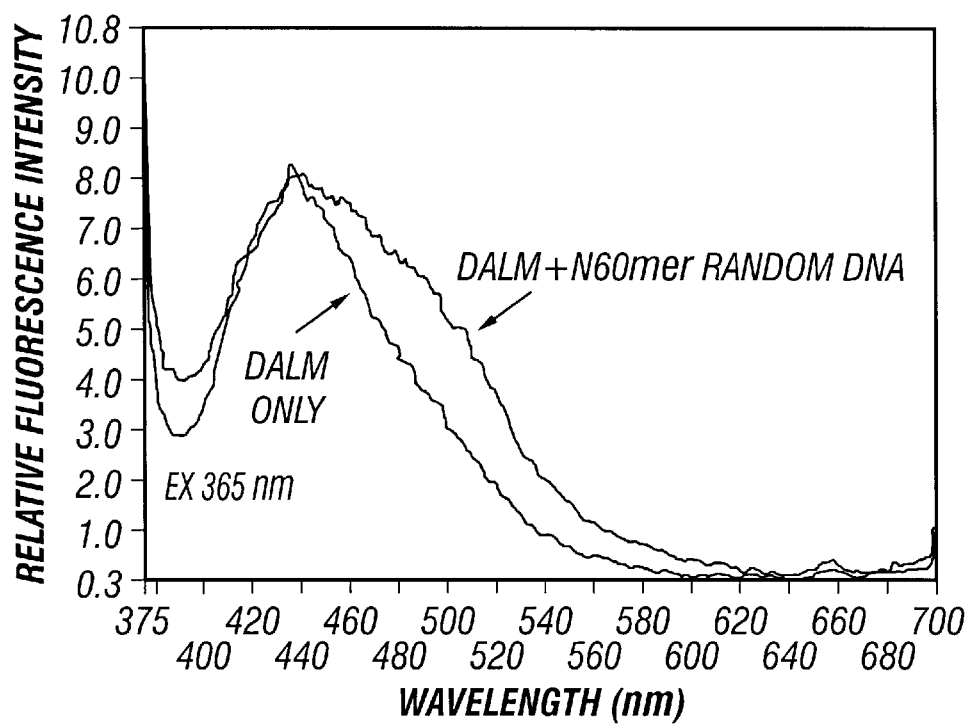
Figure 10A:
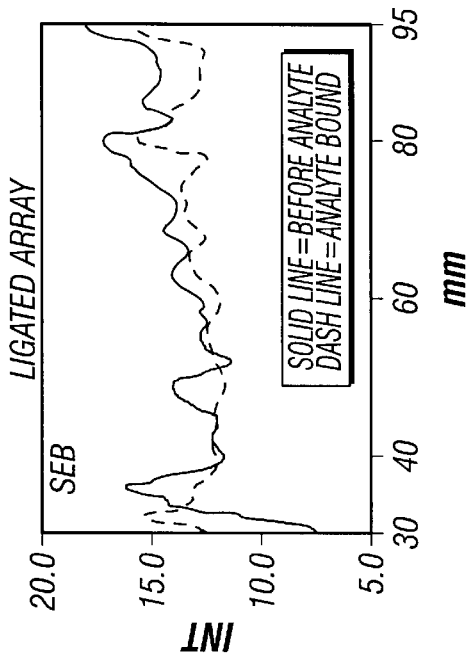
Figure 10B:
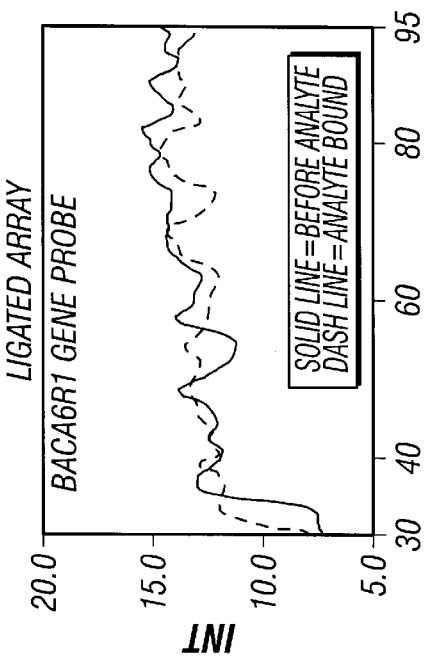
Figure 10C:
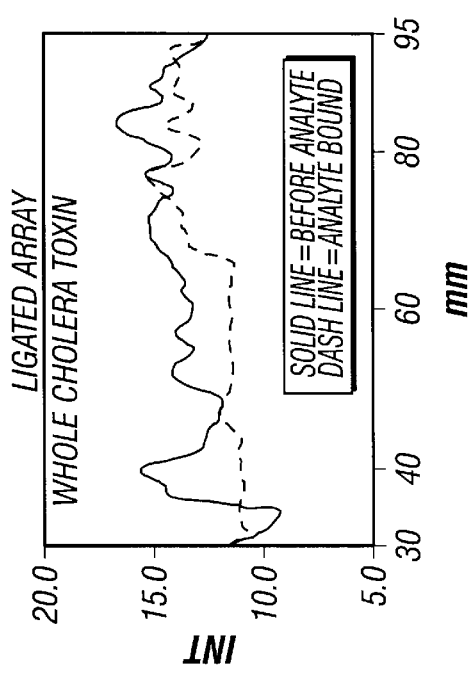
Figure 10D:
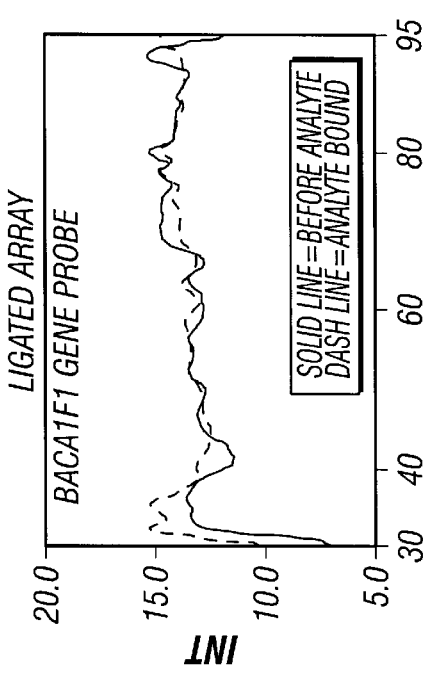
Figure 10E:
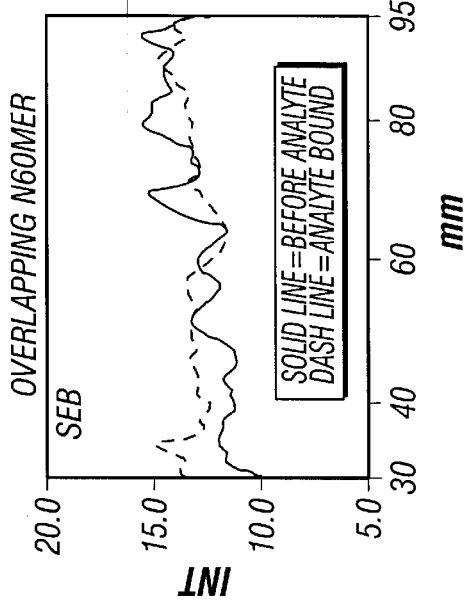
Figure 10F:
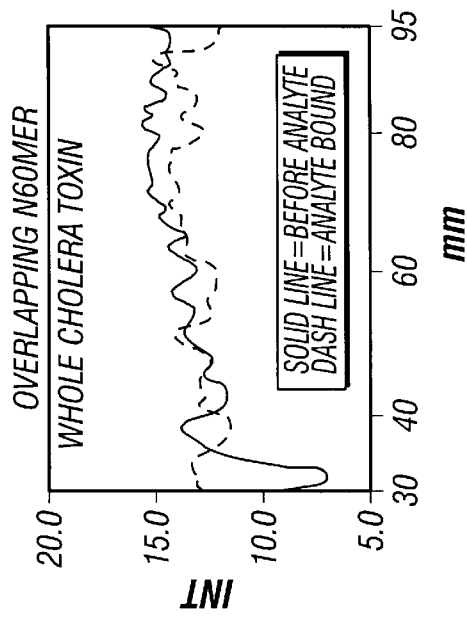
Figure 10G:
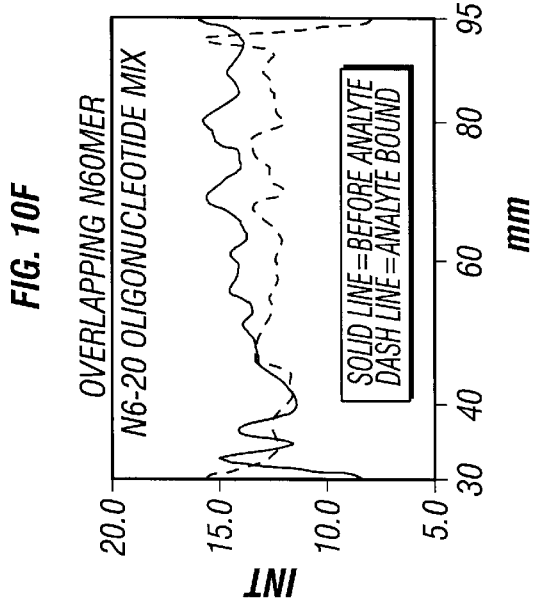
Figure 10H:
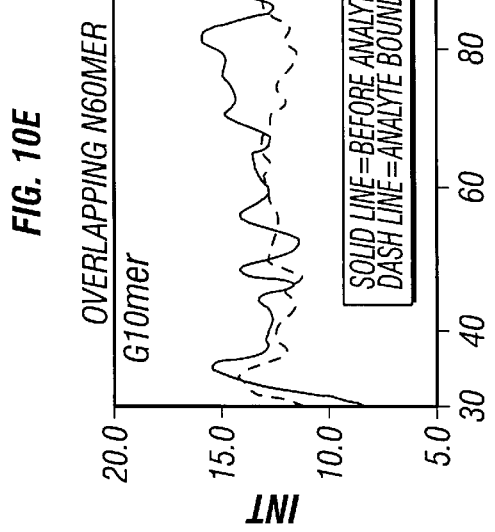

FIG. 9B illustrates a comparison of the fluorescence emission spectra of DALM (attached to an epoxy layer) before and after interaction with random 60 mer DNA. Excitation was performed at 360 nm (excitation maximum of DALM). The fluorescence of DALM with and without added nucleic acid ligands indicated enhanced fluorescence intensity and an emission spectrum shift of DALM after binding DNA (FIG. 9B). This demonstrates a fluorescence energy transfer from DALM to bound DNA and possible fluorescence enhancement of analyte-DNA array interactions in embodiments where DALM is used. In preferred embodiments, DALM serves as a photonic-electronic transducer and conductor for an attached array nucleic acid ligand layer.

FIG. 10 shows a comparison of spatial fluorescence spectra for two different types of nucleic acid ligand arrays (ligated versus random 60 mers) before and after addition of various analytes. The nucleic acid ligand arrays were electrophoresed in 10% polyacrylamide gels and fluorescence scanning was performed using an excitation of 260 nm and emission wavelength of 420 nm.

Spatial fluorescence scans of the different analyte interactions with two differently prepared nucleic acid ligand arrays suggested that the nature of the analyte and the type of array influenced the shape of the resultant scan (FIG. 10). However, some common features (e.g., peaks and valleys) existed between related scans of each array taken before (solid line) and after (dashed line) analyte binding. Most of these shared features appear to be dampened upon interaction with the analyte (FIG. 10), suggesting energy absorption by the DNA array-bound analyte. However, at specific wavelengths the fluorescence emission apparently increased upon binding of analyte (FIG. 10).

It is apparent from FIG. 10 that the ligated array produced an emission spectrum different from the random 60 mer array when identical analytes were added. It is also apparent that for a given nucleic acid ligand array, binding to a different analyte resulted in a different (and apparently unique) fluorescence emission spectrum (compare whole cholera toxin, SEB, BACA1F1 gene probe and BACA6R1 gene probe). These results validate the concept of using a recognition complex array to generate unique electrical and/or photochemical signatures capable of identifying individual analytes.

Example 2
Interaction of Recognition Complex System With Whole Cholera Toxin and DALM
Materials and Methods Randomized 40 mer template DNA flanked by 5' polyA and 3' polyT (10 mer) regions was obtained from Genosys Corp. and PCR amplified in the presence of ddNTPs and 2 units of Taq ligase. Cholera toxin was obtained from Sigma Chemical Co. (St. Louis, Mo.). Ten $\mu$l of PCR product per gel lane was mixed 1:1 with DNA loading buffer and electrophoresed at 100 V in 10% polyacrylamide precast minigels in TBE. Gels were then treated with bacterially synthesized DALM and/or cholera toxin in 1× SELEX binding buffer (BB). Gel lanes were cut and separated and scanned for fluorescence intensity at 260 nm excitation and 420 nm emission, using a Perkin-Elmer LS-50B spectrofluorometer and fiber optic plate reader attached in the TLC plate mode. The gel lanes were scanned before and after the addition of analyte (0.1 mg/ml of cholera toxin for 1 hr. at ambient temperature with mixing). DNA gels were 65 mm long and care was taken to place gels in precisely the same position before and after mixing with analyte.

Results

Figure 11:
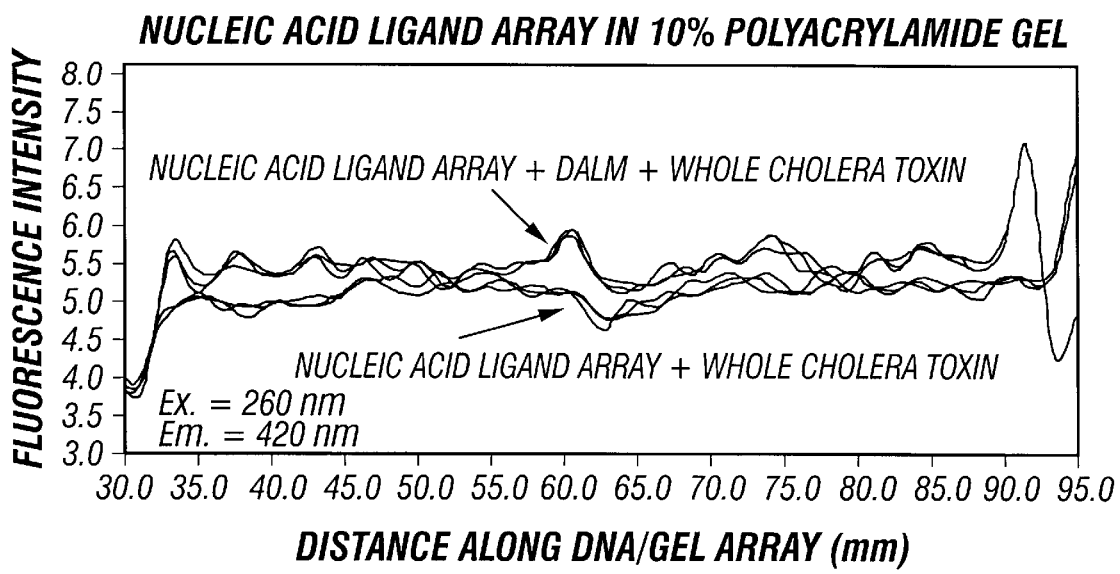

FIG. 11 illustrates differences in spatial fluorescence patterns for nucleic acid ligand arrays in 10% polyacrylamide gels with 0.1 mg/ml whole cholera toxin with and without DALM augmentation. Multiple (3 each) scans of the same DNA array in the presence and absence of analyte and/or DALM resulted in reproducible fluorescence emission profiles (FIG. 11). Addition of DALM primarily amplified the low-level fluorescence of the array DNA array and additionally changed the spatial fluorescence characteristics.

These results demonstrate the reproducibility of the photochemical signature resulting from analyte binding to an array of recognition complexes. It further demonstrates that recognition complex arrays, comprising nucleic acid ligands operatively linked to DALM, show enhanced fluorescence signals depending on the specific interaction between analyte and the individual nucleic acid ligand species.

Example 3
Alternative Recognition Complex Array
Materials and Methods

Lyophilized random DNA oligonucleotides of 40–60 bases (50 O.D. units) in length were obtained from Ransom Hill Bioscience, Inc. (Ramona, CA) and rehydrated in 1 ml autoclaved deionized water. Random oligomers were placed on ice and allowed to anneal for >1 hr. prior to electrophoresis. Ten $\mu$l of undiluted DNA oligomers were loaded across the wells of 10–20% Tris-glycine gradient polyacrylamide minigels (BioRad, Hercules, Calif.) and electrophoresed in cold 1× TBE buffer at 200 V, 150 mA, and 35W max for 75 min. Polyacrylamide gels were removed and imprints of the gels were cut with one-half of DNA Bind™ (Coming-CoStar, NOS coated) microtiter plates in a procedure hereafter referred to as the molecular cookie cutter approach. This generated small circular plugs of gel containing spatially resolved regions of the electrophoresed random DNA molecules.

These gel plugs were cut out and placed into the appropriate wells of the microtiter plate to ensure a spatial replica of the original gel. The DNA in each plug was eluted out of the gel plug onto the DNA Bind™ plate and immobilized onto the plate surface by addition of a DNA hybridization buffer (HB, 200 $\mu$L per well) at 37° C. for 2 hr.

Results

Several biotinylated target DNAs were hybridized to immobilized DNA in a DNA Bind™ plate. Plates were washed three times in HB. Hybridization patterns of the biotinylated target DNAs were detected by addition of 1:500 streptavidin-peroxidase (Southern Biotechnologies, Birmingham, Ala.) in 2% bovine serum albumin (BSA)-HB solution for 30 min at room temperature (RT). Plates were washed three more times in HB and exposed to 200 $\mu$l tetramethyl benzidine (TMB; Kirkegaard Perry Laboratories, Gaithersburg, Md.) containing hydrogen peroxide for approximately 10 min at RT to visually detect hybridization patterns. The results (not shown) demonstrate that this is an alternative approach to generating a recognition complex array.

Strong adsorption of DALM to polystyrene microtiter wells was observed at low pH (pH 5.0 or lower). This non-covalent binding was stable in the neutral pH (7 to 7.5) range, but not in alkaline pH. It is contemplated that DALM may also be immobilized using N-oxy-succinimide (NOS) treated polystyrene surfaces. An alternative method would be to link a diamino-aliphatic chain such as 1,5-diaminopentane (cadaverine), 1,6-hexane, or poly-L-lysine to the NOS and then to DALM via a carbodiimide linkage with carboxyl groups in DALM.

Figure 12:
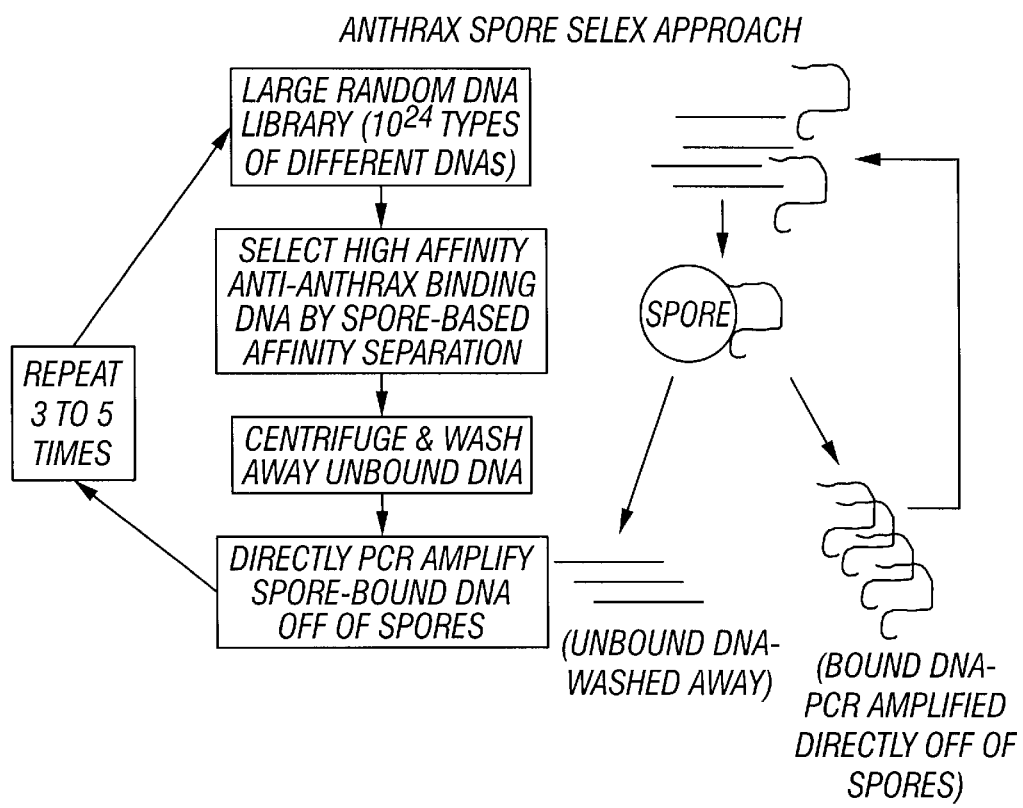

Example 4
Production of Nucleic Acid Ligands With High Affinity For Anthrax Spores Using SELEX and Magnetic Beads Systematic Evolution of Ligands by EXponential enrichment (SELEX) was used to select and PCR amplify nucleic acid ligands capable of binding to and detecting nonpathogenic Sterne strain *Bacillus anthracis* spores. A simplified affinity separation approach was employed, in which autoclaved anthrax spores were used as the separation matrix. An nucleic acid ligand-magnetic bead-electrochemiluminescence sandwich assay scheme was devised for detecting anthrax spores. The general scheme used to produce nucleic acid ligands having high affinity for anthrax spores is illustrated in FIG. 12.

Materials and Methods

Primers and Templates—The SELEX technique was used to amplify and select for analyte-binding nucleic acid ligands, using whole anthrax spores as the analyte. Primers and two sets of templates were designed to simplify PCR amplification by utilizing mirrored ends to allow amplification of the nascent strand using a single type of free primer (Bruno, 1997). Both templates consisted of 60 mers. These were composed of 5'-poly A and 3' poly T 10 mers, sandwiching a random (N) 40 mer. One set of DNA molecules (hereafter the "capture" set) consisted of templates with an amino-six carbon linker ($NH_2$-C6) attached to their 5' ends for conjugation to tosyl-activated magnetic microbeads (M-280; 2.8 $\mu$m diameter, Dynal Corp., Lake Success, N.Y.), and free unlabeled poly A 10 mer primers (FIG. 13). The other DNA set (hereafter the "reporter" set) was identical to the capture set, except that both the template and the primer were 5'-biotinylated (FIG. 13) to afford detection by binding of labeled avidin.

All oligonucleotides were obtained from Ransom Hill Biosciences, Inc. (Ramona, Calif.). All PCR reagents, except Taq polymerase, were obtained from Perkin-Elmer Corp. Taq polymerase was obtained from Fisher Scientific Corp. (Pittsburgh, Pa.).

Anthrax Spores—Sterne strain veterinary vaccine anthrax spores (Thraxol-2, Mobay Corp., Shawnee, Kans.) were streaked onto blood agar plates and incubated at 37° C. for 5 days to promote extensive sporulation and autolysis of vegetative cells. Colonies were gently washed and scraped from blood agar plates into 10 ml of filter-sterilized deionized water. The resultant suspension consisted almost exclusively of spores. Vegetative cell debris appeared to be largely removed by three washes in 10 ml of filter-sterilized deionized water with resuspension and centrifugation at 9,300× G for 10 min, as determined by phase-contrast microscopy. Spores were resuspended in 50 ml of filter-sterilized deionized water and autoclaved at 134° C. for 60 min to produce the dead stock spore suspension used in nucleic acid ligand development and detection assays. The effectiveness of autoclaving on the spore suspension was confirmed by the absence of growth on blood agar. Stock spore suspension concentration was determined by the average of four hemocytometer counts to be $6.5 \times 10^6$ spores/ml (standard deviation=$0.24 \times 10^6$) using phase-contrast microscopy at 600× magnification.

Detection—Streptavidin (Southern Biotechnology Associates Inc., Birmingham, Ala.) was labeled with N-hydroxysuccinimide-Ru(bpy)$_3^{2+}$ (IGEN International Inc., Gaithersburg, Md.) in a 15:1 protein to N-hydroxysuccinimide ECL label molar ratio as described by Gatto-Menking et al. (1995). Avidin-biotin complex reagent from a "Vectastain Elite ABC"-peroxidase kit was from Vector Laboratories, Inc. (Burlingame, Calif.). ABTS (2,2'-azino-di(3-ethyl-benzthiazoline-6-sulphonic acid) was obtained as a mixture with $H_2O_2$ added from Kirkegaard and Perry Laboratories (Gaithersburg, Md.) for colorimetric detection of spore-bound biotinylated nucleic acid ligands.

PCR Amplification—PCR was carried out prior to exposure of the nucleic acid ligand library to anthrax spores to empirically optimize the annealing temperature. A 600 $\mu$l PCR master mix consisted of 1 ng of either capture or reporter DNA templates, 1 $\mu$M final concentration of appropriate primer (free or biotinylated polyA 10 mer), 10 mM of each deoxynucleotide, 5 mM $MgCl_2$, 10 mM Tris-HCl, 50 mM KCl and 50 units of Taq polymerase in autoclaved, deionized water. Fifty $\mu$l of master mix per tube was used for empirical determination of annealing temperature using a Stratagene Corp. (La Jolla, Calif.) RoboCycler® model 96 thermal cycler with a "hot top" assembly. PCR annealing temperature was run at between 36° C. and 58° C. (data not shown). Optimal PCR conditions were determined to be: initial denaturation at 96° C. for 5 min; 40 cycles of 96° C. for 1 min, 47° C. for 1 min. 72° C. for 1 min; and final extension at 72° C. for 7 min.

SELEX Procedures—Two different SELEX procedures were employed. These methods were designated: 1) low SELEX DNA to spore exposure ratio (154 ng DNA/$10^6$ spores); and 2) high SELEX DNA to spore exposure ratio (10,256 ng DNA/$10^6$ spores). The low ratio method involved immediate addition of hot (96° C.) DNA (either capture or reporter templates) to $6.5 \times 10^6$ anthrax spores in 400 $\mu$l of sterile 2× binding buffer (2× BB, 1M NaCl, 40 mM Tris-HCl and 2 mM $MgCl_2$ in autoclaved, deionized water, pH 7.5–7.6), (Ellington & Szostak, 1990; Bruno, 1997) at ambient temperature with immediate mixing for 1 h. The high ratio procedure was identical, but involved the addition of a greater amount (10,256 ng) of heated capture or reporter DNA templates per million spores. Spore suspensions were pelleted by centrifugation at 9,300× G for 10 min. Supernatants were siphoned and discarded. Spores bound to nucleic acid ligands were resuspended in 1 ml of sterile 1× BB at room temperature. Spores were pelleted and washed twice more in 1× BB.

The spore pellet was overlaid with 100 $\mu$l of 1× BB and heated to 96° C. for 5 min to heat-liberate the bound nucleic acid ligands. The hot supernatant (100 $\mu$l) was siphoned from the spore pellet and 90 $\mu$l of the supernatant was PCR amplified in a master mix (600 $\mu$l total volume) as previously described. The remaining 10 $\mu$l of hot supernatant was electrophoresed in 2% agarose at 80 V in cold 1× Tris-borate-EDTA (TBE) buffer for 30 min. Gels were stained in 0.5 $\mu$g/ml of ethidium bromide in 1× TBE for 10 min followed by a 30 min wash in deionized water and were photographed using a 312 nm UV transilluminator and Polaroid type 667 film. Four rounds of SELEX were performed for both the low and high DNA to spore ratio methods. Fresh aliquots of the stock spore suspension were used for each round.

Nucleic acid ligand-magnetic bead preparation, ECL and calorimetric binding assays. A sandwich ECL assay scheme was designed using capture and reporter nucleic acid ligands obtained from the low DNA to spore ratio SELEX method. Capture nucleic acid ligands (100 $\mu$l of round four PCR product) were conjugated to 400 $\mu$l of stock tosyl-activated Dynal M-280 magnetic beads (approximately $2.6 \times 10^8$ beads) in the presence of 1 ml of sterile 50 $\mu$M sodium borate (pH 9.5). Conjugation was performed for 2 h at 37° C. with periodic agitation, followed by additional coupling overnight at 4° C. Magnetic microbeads were collected for 10 min using a Corning Corp. (Corning, N.Y.) magnetic separator (60 tube capacity model). Beads were washed once in 3 ml of sterile 1× BB and resuspended in 2 ml of sterile 1% bovine serum albumin (BSA), 50 $\mu$M sodium borate buffer for 2 h at 37° C. to neutralize any unreacted tosyl groups. Beads were washed three times in 3 ml of 1× BB and resuspended in 2 ml of 1× BB. The stock nucleic acid ligands-magnetic bead suspension was stored at 4° C. until used in ECL assays.

Figure 14:
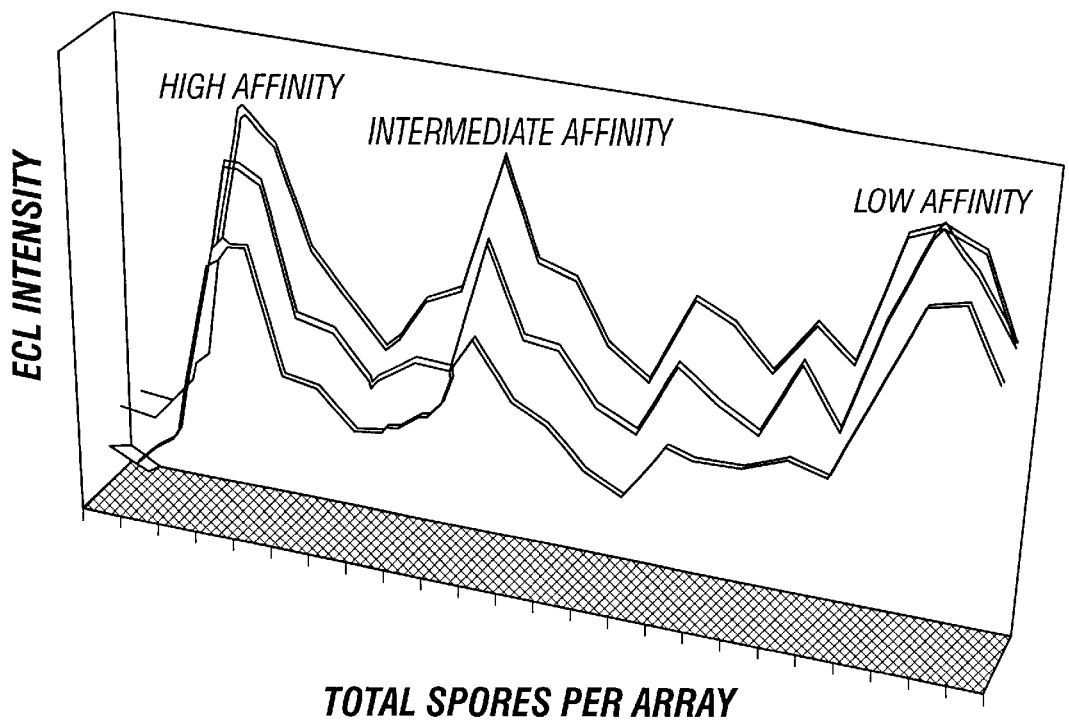

Results using heated, single stranded (ss) round four nucleic acid ligands were compared to ambient temperature, double stranded (ds) round four nucleic acid ligands in separate ECL assays. For the ss nucleic acid ligand assay, capture and reporter nucleic acid ligands were heated to 96° C. for 5 min in a water bath, immediately added to spores, and allowed to cool to ambient temperature. Two-fold dilutions of washed anthrax spores were made in 1× BB, beginning with $6.5\times10^6$ spores per assay (250 μl assay volume) and progressing to an estimated one spore per assay in a series of siliconized 12×75 mm glass tubes. Twenty μl of stock ss or ds nucleic acid ligand-magnetic bead suspensions (approximately $2.6\times10^6$ beads per assay) were added to each of the tubes, which were gently shaken for 30 min at ambient temperature.

One hundred μl of ss or ds biotinylated round four reporter nucleic acid ligands diluted 1:100 in 1× BB were added and tubes were gently shaken for 30 min at room temperature. Beads were then magnetically separated from solution and washed in 1 ml of 1× BB. One hundred μl of 1:100 1× BB-diluted streptavidin-$Ru(bpy)_3^{2+}$ was added per assay and tubes were shaken for 30 min. Beads were magnetically separated, washed once more in 1× BB and resuspended in 1 ml of 0.2 M tripropylamine (TPA) assay buffer as described previously (Gatto-Menking et al., 1995; Bruno & Yu, 1996; Yu & Bruno, 1996). Controls were run in which various individual and multiple components of the sandwich assay were deleted. ECL measurements were obtained with an Origen® analyzer (IGEN International Inc.) using an assay gain setting of 1,000 and all other parameters as previously reported (Gatto-Menking et al., 1995; Bruno & Yu, 1996; Yu & Bruno, 1996).

Colorimetric detection of nucleic acid ligand binding to spores from the high ratio DNA to spore assay was achieved by addition of 200 μl of Vectastain Elite avidin-biotin complex (ABC)-peroxidase reagent in 1× BB to resuspended spore pellets from each round of SELEX (including a pre-SELEX control). After for 30 min at ambient temperature, spores were centrifuged and washed three times in 1 ml of 1× BB. Spore pellets were resuspended in 400 μl of ABTS for 15 min. Four 100 μl aliquots from each tube were placed into microtiter wells and absorbance at 405 nm was determined using an automated plate reader.

Results

The present example employed a simplified PCR scheme, in which only one type of template and primer were required, because the nascent strand is synthesized with mirrored ends (FIG. 13) and is capable of binding the polyA 10 mer primer to initiate the next round of PCR. Annealing temperature is especially critical when random template regions are employed, as any free primer sequence may encounter a partially or completely complementary sequence with which to hybridize in the random region (Tuerk, 1990, 1993, 1997; Bruno, 1997). Partial hybridization of the random regions with themselves can be self-priming for Taq polymerase and leads to high molecular weight PCR products (Tuerk, 1990, 1993, 1997; Bruno, 1997).

The most abundant PCR product was obtained at an annealing temperature of 47° C., but surprisingly the apparent molecular weight of the PCR product did not decrease with annealing temperatures beyond 47° C. (i.e., increased stringency by temperature did not alter the size of the PCR product). Addition of Taq polymerase at >80° C. (i.e., "hot start" technique) also did not alter the apparent molecular weight of the PCR product. Thus, 47° C. was selected as the standard annealing temperature.

Another consideration was that genomic anthrax DNA might be present in the spore preparation (Reif et al., 1994), which might be amplified by hybridizing to the primer or template. Control experiments were run in which baseline levels of genomic DNA in the spore preparation and possible PCR amplification of genomic DNA from the spore preparation (spores plus Taq polymerase with and without SELEX templates or primers) were evaluated. While a minute amount of genomic DNA was barely detectable in gels and could be mildly amplified from spore preparations, the levels of endogenous DNA were insufficient to account for the levels of PCR products seen after each round of SELEX. Genomic DNA from the spore preparations was different from the SELEX PCR product in its gel electrophoretic migratory pattern. Thus, it is clear that PCR amplification of nucleic acid ligands from the spore surface dominated the pool of amplified DNA.

ECL-based and colorimetric binding assays (FIG. 8 and FIG. 14) were employed to assess nucleic acid ligand binding to anthrax spores. Double stranded low DNA-to-spore ratio nucleic acid ligands produced no detectable binding to anthrax spores (data not shown). When heat-denatured (96° C.) to produce single-stranded forms and then cooled to room temperature in the presence of spores, binding to spore components became detectable using the ECL sandwich detection scheme (FIG. 14). Spores were not observed to bind directly to nucleic acid ligand-conjugated magnetic beads by microscopy. Thus, detection limits probably reflect detection of spore components shed from an equivalent amount of spores indicated at each datapoint. Despite the lack of observed spore binding, the data suggest a broad dynamic range from <10 to >$6\times10^6$ anthrax spores for this assay (FIG. 14).

FIG. 14 also demonstrates the existence of at least three distinct populations of aptamers having low, intermediate and high affinity spore epitope binding capacities. This heterogeneous binding affinity behavior is analogous to that observed from polyclonal antisera (Roitt et al., 1985). Controls, in which one or more of the components of the ECL assay were deleted to evaluate background ECL levels were consistently at or below the background levels seen in FIG. 14 (data not shown). The three independent trials depicted in FIG. 14 demonstrate the reproducibility of heterogeneous binding behavior of this family of anti-anthrax spore nucleic acid ligands.

The nucleic acid ligands developed by the low DNA to spore ratio method was consistently heat-liberated at 96° C. from spore pellets after each round of SELEX. However, in the high DNA to spore ratio SELEX, a set of nucleic acid ligands was developed after three rounds of SELEX that apparently could not be heat-eluted off the spore surface even at 99° C. for 5 min (FIG. 8A). These ultrahigh affinity nucleic acid ligands were detectable by way of their biotinylated tails via streptavidin-Ru(bpy) ECL and avidin-peroxidase methods (data not shown). Round 4 SELEX PCR product is not shown in FIG. 8A because no PCR product was detected following two separate amplification attempts.

The decreasing levels of PCR products (especially the lower molecular weight bands) as a function of SELEX round, shows that tighter binding nucleic acid ligands were selected after each round, which led to lesser amounts of detectable PCR products. The data in FIG. 8A demonstrates that eventually nucleic acid ligands with such high binding affinity were achieved that they could no longer be heat-eluted, at least not by a conventional thermal cycler. However, nucleic acid ligands DNA was still bound to the spore surface, because the biotinylated tails of the nucleic acid ligands were detectable by two avidin-based methods (not shown). It was later shown that these high affinity nucleic acid ligands could be eluted from the spore surface by resuspension of the pellet in deionized water or 2 mM EDTA (Ellington & Szostak, 1990; 1992).

When compared to binding assay results obtained from nucleic acid ligands developed by the low DNA to spore ratio method (FIG. 14), these results show that DNA to analyte (spore) ratio may be an important factor in determining the eventual affinity of the resulting nucleic acid ligand population. These results show that nucleic acid ligands with high affinity for target analytes can be generated using the methods of the instant invention.

Example 5
Neutralization Of Biohazardous Agents Using DALM

In a preferred embodiment of the instant invention, nucleic acid ligands with high affinity for a target analyte are produced and purified using the disclosed methods. Such nucleic acid ligands may be used to neutralize biohazardous agents, such as viruses, microbes, spores or potentially single molecules.

Figure 15:
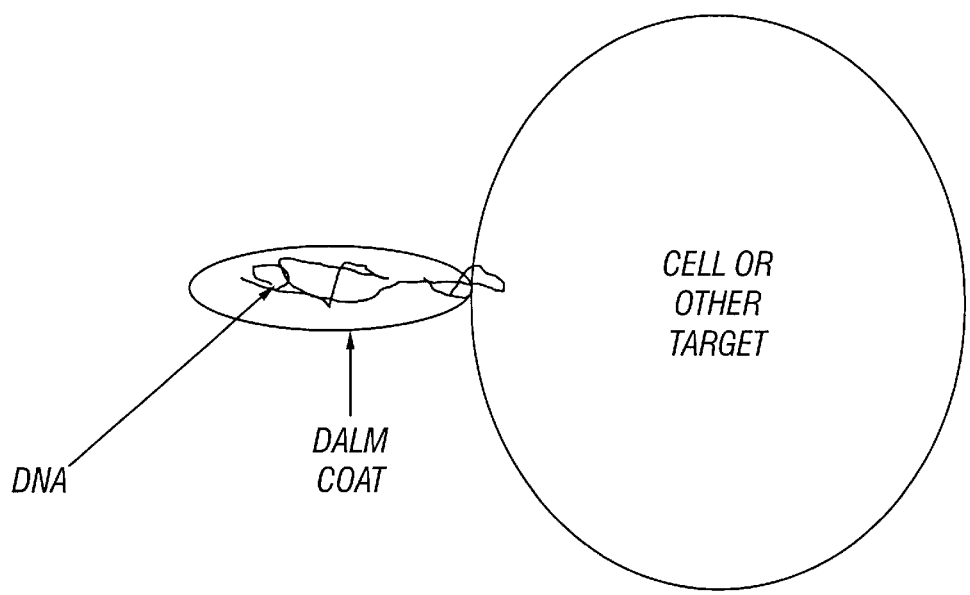
Figure 16:
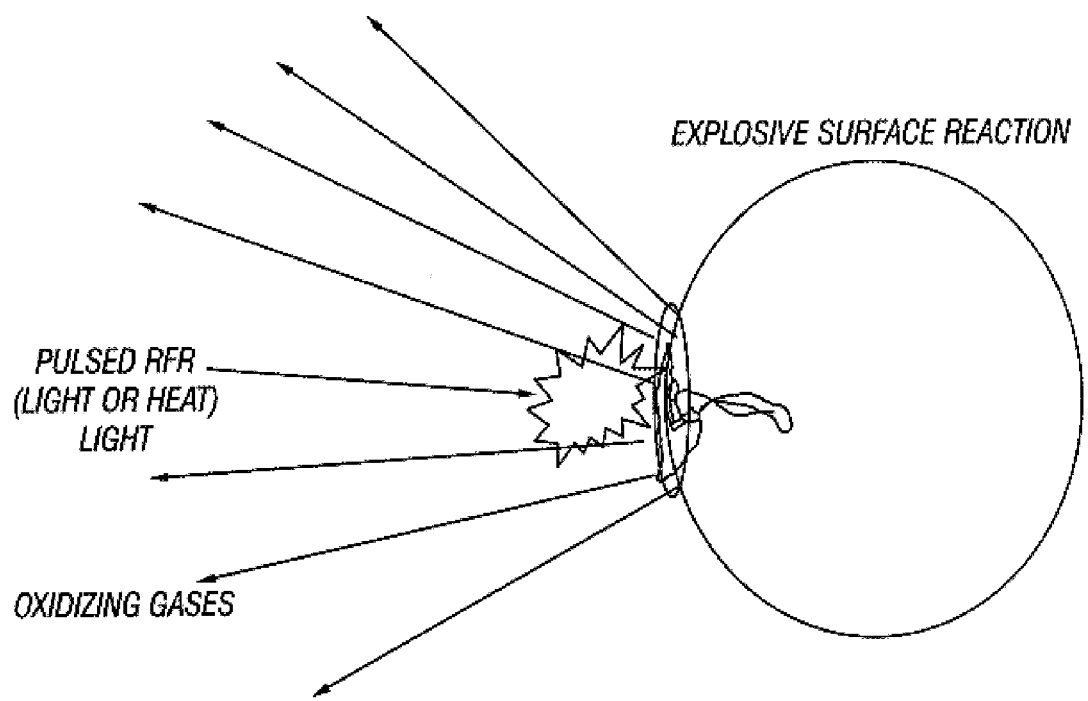
Figure 17:
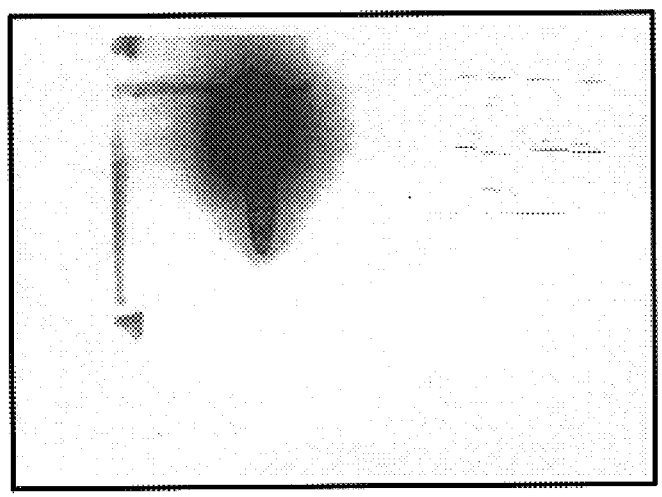
Figure 18A:
Figure 18B:
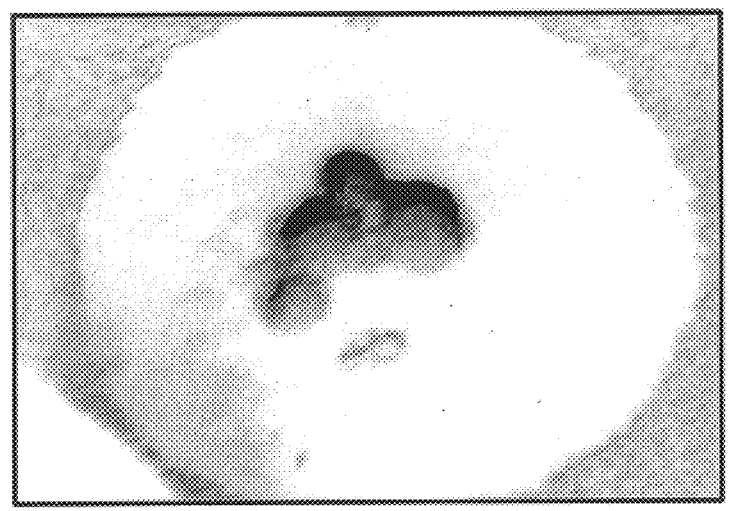

A general approach to this process is illustrated in FIG. 15. High affinity nucleic acid ligands may be produced as disclosed in the preceding examples. Such nucleic acid ligands may be attached to a compound such as DALM. The nucleic acid ligand provides specificity of binding to the target. The DALM-nucleic acid ligand couplet is then used essentially as a photochemical transducer, as shown in FIG. 16.

DALM is capable of absorbing electromagnetic radiation within a broad range of wavelengths and transmitting the absorbed energy to molecules or targets to which it is attached. In FIG. 16, DALM attached to a target via a bound nucleic acid ligand is irradiated with a pulse of electromagnetic radiation. In the figure, the radiation is transmitted in the form of visible light or infrared radiation, but other forms of irradiation, such as microwave, laser or radiofrequency are contemplated within the scope of the present invention. Irradiation results in absorption of energy by DALM, which is transmitted to the target. The resulting heating and production of reactive chemical species produces an explosive surface reaction that destroys the target.

DALM activated by hydrogen peroxide and bicarbonate and pulsed with microwave radiation acts as a photochemical transducer, releasing an intense pulse of visible light (FIG. 17). High power pulsed microwave radiation (HPM), applied to solutions containing dissolved carbon dioxide (or bicarbonate), hydrogen peroxide and DALM generates sound, pulsed luminescence and electrical discharge. Microbes exposed to these conditions experience damage comparable to short time, high temperature insults, even though measurable localized temperatures were insufficient to cause the observed effects.

Materials and Methods

*Bacillus anthracis* spores were incubated with DALM and exposed to a high power microwave (HPM) pulse. *Bacillus anthracis* (BA; Steme strain) spore vaccine (Thraxol™, Mobay Corp., Animal Health Division, Shawnee, Kans. 66201) was centrifuged, the supernatant decanted and the button washed with chilled deionized water. Dilute powdered milk solution was made to a concentration of 25 mg of powdered milk solids/ml of deionized water, filtered through a 0.2 micron filter. The BA button was resuspended in 1 ml of sterile milk solution to form a BA suspension.

For pulsed microwave exposure, 0.5 ml of BA spore suspension was placed into 0.2 micron-filter centrifuge tubes (Microfilterfuge™, Rainin Instrument Co., Inc., Woburn, Mass. 01888-4026). The spores were centrifuged onto the filter at 16,000× g for 15 min. The tubes were refilled with 1.5 ml of a reaction mixture consisting of 0.9 ml saturated sodium bicarbonate/luminol solution, 0.1 ml of 1:10 biosynthetic DALM, 0.6 ml of 1:10 diazoluminol, and 0.33 ml 3% hydrogen peroxide. All dilutions were made in saturated sodium bicarbonate/luminol solution. The final dilution of DALM was 1:1000. A detailed description of the reaction mixture has been published (Kiel et al., 1999a; Kiel et al., 199b).

The filter, with the BA spores, was inserted into the tube to a level just below the meniscus of the fluid. The solution was exposed to 10 pulses per second of HPM (1.25 GHz, 6 $\mu$s pulse, 2 MW peak incident power), starting at 3 minutes and 22 seconds after placing the reaction mixture in front of the microwave waveguide. The exposure lasted for 13 min and 28 sec. Total radiation exposure was for 48 msec. The temperature of the sample, continuously monitored with a non-perturbing, high-resistance temperature probe (Vitek™), began at 25.3° C. and reached an end point of 64° C., below the lethal temperature for anthrax spores.

Results

FIG. 18 shows the result of this procedure. The control spore on the left was exposed to HPM in the absence of DALM. It remained intact. The anthrax spore on the right of FIG. 18 was exposed to HPM in the presence of DALM. The spore lysed, with its contents spread around the remnants of the spore (FIG. 18). The effect of HPM and DALM on anthrax spores shows that DALM may be used to neutralize biohazardous agents against which high affinity nucleic acid ligands are prepared by the methods disclosed herein.

Example 6

PCR Amplification of Nucleic Acid Ligands Attached to DALM/Magnetic Beads

Materials and Methods

A plasmid (pSV2neo NR103Xgal) was constructed with the barley nitrate reductase 1.1 kb fragment inserted into the EcoRl site and the 3.1 kb Xgal cartridge inserted into the BamHl site of the 5.8 kb pSV2neo plasmid. The resulting plasmid was approximately 10 kb in size.

DALM was attached to magnetic beads by a modification of the method of Guiot and Couvreur (1986). A solution of 150 ml of 0.67 M $FeSO_4$ and 100 ml of 1.0 M $Fe_2(SO_4)_3$ was mixed and shaken, followed by addition of 128 ml of 250 g/l NaOH. After neutralization at 35° C., the pH was adjusted to between 11 and 12 with NaOH solution. The neutralized solution was shaken for 20 min and then cooled. The pH was adjusted to 5.5 with 1 N HCl. After 10 times washing with excess water and decantation, the particles were filtered and dried to form a magnetic powder. The magnetic powder was resuspended in aqueous medium. DALM was added to freshly prepared magnetic particles and was adsorbed onto the particles.

Plasmid DNA (3 $\mu$g) was added to the DALM/magnetic beads in the presence of either 0.4 or 4.0 mM $MgCl_2$ (final concentration) in 25 $\mu$l of aqueous solution. Samples as indicated below were boiled for 10 min in a water bath, then removed and all samples were placed in an incubator at 37° C. for 30 min. Treatments used were: [1] boil DNA, 4.0 mM $MgCl_2$ and beads; [2] boil DNA, 0.4 mM $MgCl_2$ and beads; [3] boil DNA, then add 4.0 mM $MgCl_2$ and beads; [4] boil DNA, then add 0.4 mM $MgCl_2$ and beads; [5] boil DNA and 4.0 mM $MgCl_2$, then add beads; [6] boil DNA and 0.4 mM $MgCl_2$, then add beads; [7] no boiling, incubate DNA, 4.0 mM $MgCl_2$ and beads; [8] no boiling, incubated DNA 0.4 mM $MgCl_2$ and beads.

After incubation, samples were centrifuged and supernatant removed. A 10 $\mu$l aliquot of supernatant was taken and 1:100 and 1:10,000 dilutions were made. PCR was performed on undiluted supernatant, 1:100 and 1:10,000 dilutions. The remainder of the supernatant was ethanol precipitated using 35 $\mu$l ethanol and 1.5 $\mu$l sodium acetate and left at −20° C. overnight. After centrifugation the DNA pellet was dissolved in 20 $\mu$l water and 1 $\mu$l was taken for PCR.

The beads were resuspended in 20 μl of water. One μl was diluted 1:100 and 1 μl of this was diluted again 1:100 to give a 1:10,000 dilution. One μl of undiluted beads or 5.0 μl of each dilution was used for PCR.

PCR amplification of a 949 bp fragment of the nitrite reductase gene was performed for 35 cycles at 94° C. for 45 sec; 65° C. for 45 sec; 72° C. for 2 min, followed by 72° C. for 5 min. Sample (1–5 μl) was added to 5 μl of 10× PCR buffer (Display TAQ), 10 mM dNTPs, Display TAQ polymerase (5 U/μl, Display Systems Biotech, Inc.), 20 μM primer (Sigma Genosys) and water added to 50 μl. Forward and reverse primers were designed to amplify the 949 bp fragment of the nitrite reductase gene, as shown below.

Forward:
5'-ACAACTCCGACAACTCGGTGCACGGTGGGT-3' (SEQ ID NO:1)

Reverse:
5'-GGCAGCTCCATGCTACCTATGAGTAGGTAC-3' (SEQ ID NO:2)

Results

Since diluted beads showed activity in a number of treatments and undiluted beads did not, controls were run with the 1.1 kb nitrate reductase (0.5 ng/sample) added to the tube to determine if the beads themselves were inhibiting PCR. Products of expected size was seen with 1:100 and 1:10,000 dilutions, but not with undiluted beads, suggesting that the beads were adsorbing all the PCR reagents and preventing PCR amplification.

The results showed that DNA binds to DALM/magnetic beads in the presence of magnesium ion (not shown). A PCR product from treatment #5, 1:100 dilution of beads was Southern blotted and probed with 948 bp nitrate reductase fragment labeled with $^{32}$P dCTP. Results confirmed that the PCR product is the nitrate reductase fragment (not shown). These results show that DALM can be attached to magnetic beads and that DNA binds to DALM in the presence of magnesium ion, providing an alternate embodiment for a recognition complex system in which recognition complexes are attached to magnetic beads. Nucleic acid ligands can be released from the DALM/magnetic beads by incubation with a magnesium chelator, such as EDTA.

Example 7

Autoradiograpy of Nucleic Acids Attached to DALM/Magnetic Beads

Materials and Methods

Plasmid pSV2neo NR1.1Xgal, constructed by standard techniques as described above, was nick translated using [P]$^{32}$-dCTP to provide a radiolabeled nucleic acid. One microgram of plasmid DNA was incubated with the following, diluted with distilled water to a volume of 25 μl.

(a) DALM/magnetic beads+Mg$^{2+}$ (4 mM)

(b) magnetic beads+Mg$^{2+}$ (4 mM)

(c) Mg$^{2+}$ (4 nM)

Samples were boiled for 10 minutes and cooled for 30 minutes at 37° C. After centrifugation to pellet the beads the distribution of radiolabeled DNA was determined with a BIOSCAN/QC.4000 XER. The cpm (counts per minute) in pellet and supernatant were:

|     | Pellet  | Supernatant |
| --- | ------- | ----------- |
| (a) | 116,584 | 5,299       |
| (b) | 64,741  | 11,628      |
| (c) | —       | 42,854      |

The addition of DALM resulted in an increased attachment of DNA to the magnetic beads in the presence of magnesium. After washing with 200 μl of buffer, beads were resuspended and subjected to PCR amplification as described above. Only sample (c) showed an amplification product using primers to the barley nitrate reductase gene (not shown). It is unknown if the absence of an amplification product in the bead-containing samples was due to the adsorption of primers and/or DNA template on to the beads. Samples were loaded on an agarose gel, subjected to electrophoresis and then autoradiographed. Radiolabeled DNA was present at the bottoms of the sample wells from samples containing beads (not shown), demonstrating that DNA bound to the magnetic particles. This study was repeated using DNA from *Bacillus anthracis* (Sterne strain) with similar results (not shown).

Example 8

DALM/DNA Binding to Magnetic Beads and PCR Amplification

Materials and Methods

Twenty five μg of lambda DNA was digested with Sau3A1 restriction enzyme in 100 μl reaction mix. The digest was ethanol precipitated and dissolved in 100 μl of DNA buffer (10 mM tris pH 8.0/1 mM EDTA. Dilutions (1:10 and 1:100) were made of DALM/magnetite beads (DM beads) in DNA buffer. A mixture of 10 μl each DM bead suspension, 1.0 μl MgCl2 (1M) and 50 μl of Sau3A1 digested lambda DNA was boiled for 10 min and cooled for 30 min at 37° C. A 10 μl aliquot was removed from the mixture and luminescence was determined on the Turner Luminometer using 100 μl 0.3 M sodium carbonate and 50 μl hydrogen peroxide. Luminescence was observed from the samples showing that the DNA had not quenched the signal completely. A 3 μl sample of each mixture was subjected to agarose gel electrophoresis to check the Sau3A1 DNA digest and the beads after boiling.

Fifty μg of *Bacillus anthracis* DNA was added to the remaining mixture. An aliquot of 3 μl was removed for PCR, and the remaining sample was boiled for 10 min and then cooled at 37° C. for 30 min. After cooling, the beads were washed three times with 100 μl DNA buffer, the washes were retained and 5 μl aliquots of the washes and 1 μl of 1:10 dilution of beads before and after boiling were subjected to PCR using conditions described above. An aliquot of 10 μl was used for agarose gel electrophoresis.

The primers used for PCR amplification of the PA (protective antigen) DNA were:

Forward:
5'-ATCACCAGAGGCAAGACACCCCCTTGTGGC-3' (SEQ ID NO:3)

Reverse:
5'-GTCAACTGATTCTTGATATTTTGAGATGTT-3' (SEQ ID NO:4)

PCR amplification was performed after an initial strand separation (96° C. for 2 min) for 35 cycles at 94° C. for 1 min, 60° C. for 1 min, and 72° C. for 1 min, followed by a final elongation at 72° C. for 5 min.

Results

The Sau3A1 digest of lambda DNA alone showed distinct bands of size range 1.5 kb to 100 bp on staining with ethidium bromide. After boiling and ethidium bromide staining, the digested lambda DNA in the presence of DM beads showed a smear of DNA from the loading well to an apparent size of 100 bp, with a strong signal seen in the gel well, showing that much of the DNA remained in the well. A brown precipitate due to the DM beads was observed in the well after the gel was run. Most of the ethidium bromide signal was seen in the well, showing that the DNA was attached to the beads.

PCR amplification of the *B. anthracis* DNA showed that all samples except the 1:10 dilution of beads after boiling contained a PCR product of the size expected from the PA antigen of the pXO1 plasmid carried by the Sterne strain *B. anthracis* used in this study. The lack of product in the 1:10 dilution of beads is consistent with previous results where no product was seen where the bead concentration was high. The beads were washed for a total of 14 times as described and product was still observed. After 10 washes, dilution of the 1:10 beads at ratios of 1:10, 1:50, 1:100 and 1:200 gave product in the first 3 dilutions, but not in the 1:200. A 2 µl aliquot was used for the PCR. PCR of 2 additional washes of the diluted beads before the PCR was performed showed no product. These results were consistent with earlier findings that dilution of beads is important, but also show the feasibility of detecting of *B. anthracis* DNA attached to DM beads. PCR, using the same conditions, was also performed on 250 and 500 ng samples of lambda DNA to eliminate the possibility that any PCR product may be due to this DNA and not from the *B anthracis*. *B. anthracis* PA antigen can be detected using 250 ng of *B. anthracis* genomic DNA. No product was seen with the lambda DNA template.

Example 9
CIE Colorimetry Analysis

The addition of an analyte in solution, such as DNA, RNA, lipids, carbohydrates, proteins, metals, aromatic or polycyclic hydrocarbons to the recognition complex changes its conductive and photochemical properties. By irradiating the array of nucleic acid ligand/DALM couplets and bound analyte with long wavelength ultraviolet light (360–400 nm), the change in fluorescence spectra, effected by the binding, can be observed by a charged couple device camera, chip, the eye, or other photodetector, such as a photomultiplier tube with appropriate optical filters or grating to detect spectral shifts. The total color pattern change of the array can be represented as its chromaticity, giving a color emission and intensity map peculiar to the analyte/DNA/DALM triplets.

The characteristic signature of an analyte consists of the two-dimensional distribution of fluorescence resulting from long-wavelength-light excitation. Response of the sensor at a specific spatial location may be similar for two or more different analytes, but by combining the fluorescence response of many independent measurement locations, specificity can be high. Analysis of signatures is essentially a comparison of multiple channels of fluorescence spectral signatures. Use of standard CIE colorimetry methods streamlines processing by representing spectral distributions at each spatial location as CIE chromaticity coordinates (two numbers), and provides a means that is color oriented and relatively independent of intensity. Comparison of signatures could readily be implemented using artificial neural networks (e.g., Qnet v2000 neural net software package from Vesta Services, Inc., 1001 Green Bay Rd., Winnetka, Ill. 60093) or other decision methods, operating on the arrays of two-number (CIE chromaticity coordinates) that are the signatures. This provides a fast comparison among analytes to a growing database of previously recorded signatures. DALM could be linked to surfaces and nucleic acid ligands specific for the binding of known agents applied so that the chip could be read visually by color or fluorescence change with a UV lamp or hand-held or remote laser. The DALM/nucleic acid ligand couplets could also be applied as a "paint" to various surfaces and equipment to be read in such a passive way as aforementioned.

One exemplary method of data analysis would involve the use of standard color CCD camera chips to measure red (R), green (G) and blue (B) values of the light emitted from each recognition complex of a array array. In an illustrative embodiment, the fluorescence intensity spectra for DALM in the presence or absence of random 60 mer DNA were compared (FIG. 19). The two spectra were encoded as CIE tristimulus values arbitrarily using the CIE 1931 color matching functions. From the tristimulus values, $RGB_{709}$ values were computed to simulate capture of RGB values using a standard color CCD chip (video or digital camera). Chromaticity values were computed to map the spectra into a standard color space. Measurement of brightness in addition to RGB would provide a third (in addition to CIE (xy) coordinates) parameter for better discrimination.

FIG. 19 shows the two spectra analyzed (left) and the resulting CIE chromaticity diagram (right). The CIE diagram shows the locus of the standard white $D_{65}$ point (white diamond), the $RGB_{709}$ values (solid diamonds) and the points representing the two spectral distributions (solid triangles).

A group of such points, one for each sensor location, comprises the signature associated with an unknown analyte. Association of unknown composite, multispot signatures with known signatures from a reference set can be performed by artificial neural network (e.g., Qnet v2000 neural net software package from Vesta Services, Inc., 1001 Green Bay Rd., Winnetka, Ill. 60093) or other computational decision means known in the art. Colorimetry provides a significant data compression that will facilitate high speed detection and identification of analytes, using compact, low power instrumentation.

All of the COMPOSITIONS, METHODS and APPARATUS disclosed and claimed herein can be made and executed without undue experimentation in light of the present disclosure. While the compositions and methods of this invention have been described in terms of preferred embodiments, it will be apparent to those of skill in the art that variations may be applied to the COMPOSITIONS, METHODS and APPARATUS and in the steps or in the sequence of steps of the methods described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Bruno and Yu, Immunomagnetic-electrochemiluminescent detection of *Bacillus anthracis* spores in soil matrices. *Appl. Environ. Microbiol.* 62: 3474–76, 1996.

Bruno, In vitro selection of DNA to chloroaromatics using magnetic microbead-based affinity separation and fluorescence detection. *Biochim. Biophys. Res. Comm.* 234, 117–120, 1997.

Bruno et al., Preliminary electrochemiluminescence studies of metal ion-bacterial diazoluminomelanin (DALM) interactions. *J. Biolumin. Chemilumin.* 13: 117–123, 1998.

Effenhauser, et al. *Anal. Chem.*, 66:2949–2953, 1994.

Effenhauser, et al. *Anal. Chem.*, 65:2637–2642, 1993.

Egholm et al., *Nature*, 365:566, 1993.

Ellington and Szostak, In vitro selection of RNA molecules that bind specific ligands. *Nature* 346: 818–822, 1990.

Ellington and Szostak, Selection in vitro of single stranded DNA molecules that fold into specific ligand-binding structures. *Nature* 355: 850–52, 1992.

Fodor et al., Multiplexed biochemical assays with biological chips. *Nature* 364, 555–556, 1993.

Freifelder, *Physical Biochemistry Applications to Biochemistry and Molecular Biology*, 2nd ed. Wm. Freeman and Co., New York, N.Y., 1982.

Froehler, B., *Tet Lett.* 27:5575–5578, 1986a.

Froehler, B., et al., *Nucleic Acids Research*, 14:5399–5467, 1986b.

Froehler, B., et al. *Nucleosides and Nucleotides*, 6:287–291, 1987.

Froehler, B., et al. *Nucleic Acids Research*, 16:4831–4839, 1988.

Frohman, In: PCR™ Protocols: *A Guide To Methods And Applications*, Academic Press, N.Y., 1990.

Gatto-Menking et al., Sensitive detection of biotoxoids and bacterial spores using an immunomagnetic electrochemiluminescence sensor. *Biosensors Bioelectronics* 10: 501–507, 1995.

Guild, The colorimetric properties of the spectrum. *Philosophical Transactions of the Royal Society*, A, 230:149–187, 1931.

Guiot and Couvreur (eds), *Polymeric Nanoparticles and Microspheres*, CRC Press, pp. 97–103, 1986.

Hacia et al., *Nature Genetics*, 14:441–447, 1996.

Harrison et al., *Science*, 261:895–897, 1993.

Holmstrom, K. et al., *Anal. Biochem.* 209:278–283, 1993.

Innis et al., PCR *Protocols*, Academic Press, Inc., San Diego Calif., 1990.

Jacobson, et al., *Anal. Chem.*, 66:1107–1113, 1994.

Jayasena, S. D., Aptamers: An Emerging Class of Molecules That Rival Antibodies in Diagnostics. *Clin. Chem.* 45: 1628–1650, 1999.

Kiel et al. "Luminescent radio frequency radiation dosimetry." *Bioelectromagnetics* 20:46–51, 1999a.

Kiel et al, "Pulsed microwave induced light, sound, and electrical discharge enhanced by a biopolymer." *Bioelectromagnetics* 20:216–223, 1999b.

Klug and Famulok, All you wanted to know about SELEX. *Mol. Biol.* Reports 20: 97–107, 1994.

Kornberg and Baker, DNA Replication, 2d Ed., (Freeman), San Francisco, 1992.

Kwoh et al., *Proc. Nat. Acad. Sci.* USA, 86: 1173, 1989.

Kugler et al., "Photoelectron spectroscopy and quantum chemical modeling applied to polymer surfaces and interfaces in light-emitting devices." *Accounts of Chemical Research* 32:225–234, 1999.

Lipshutz et al., Using oligonucleotide probe arrays to access genetic diversity. *Biotechniques* 19: 442–447, 1995.

Lorsch and Szostak, In vitro selection of nucleic acid sequences that bind small molecules. In: *Combinatorial Libraries: Synthesis, Screening and Application Potential.* (R. Cortese, ed.) Walter de Gruyter Publishing Co., New York, pp. 69–86, 1996.

Manz, et al., *J. Chromatogr.*, 593:253–258, 1992.

Matson et al., Biopolymer synthesis on polypropylene supports: oligonucleotide arrays. *Anal. Biochem.* 224: 110–116, 1995.

Newton, et al. *Nucl. Acids Res.* 21:1155–1162, 1993.

Ohara et al., *Proc. Nat'l Acad. Sci.* USA, 86:5673–5677, 1989.

Pease et al., Light-generated oligonucleotide arrays for rapid DNA sequence analysis. *Proc. Natl. Acad. Sci.* USA 91: 5022–26, 1994.

Rasmussen, et al., *Anal. Biochem*, 198:138–142, 1991.

Reif et al., Identification of capsule-forming *Bacillus anthracis* spores with the PCR and a novel dual-probe hybridization format. *Appl. Environ. Microbiol.* 60:1622–25, 1994.

Roitt et al., In: *Immunology*, pp. 5–6, Gower Medical Publishing Ltd., London, 1985.

Running. J. A. et al., *BioTechniques* 8:276–277, 1990.

Sambrook et al., In: *Molecular Cloning: A Laboratory Manual*, 2d Ed., Cold Spring Harbor Laboratory Press, Cold Spring Harbor, N.Y., 1989.

Scheit, Nucleotide Analogs, John Wiley, New York, 1980.

Shoemaker et al., *Nature Genetics* 14:450–456, 1996.

Southern et al., Arrays of complementary oligonucleotides for analyzing the hybridization behaviour of nucleic acids. *Nucleic Acids Res.* 22: 1368–73, 1994.

Travis, Chips ahoy: microchips covered with DNA emerge as powerful research tools. *Science News* 151: 144–45, 1997.

Tsuda et al., *Anal. Chem.*, 62:2149–2152, 1990.

Tuerk, Systematic evolution of ligands by exponential enrichment: RNA ligands to bacteriophage T4 DNA polymerase. *Science* 249: 505–510, 1990.

Tuerk, In vitro evolution of functional nucleic acids: high-affinity RNA ligands of HIV-1 proteins. *Gene* 137: 33–39, 1993.

Tuerk, Using the SELEX combinatorial chemistry process to find high affinity nucleic acid ligands to target molecules. *Meth. Mol. Biol.* 67: 219–30, 1997.

Walker et al., *Proc. Natl. Acad. Sci.* USA, 89:392–396 1992.

Weetall, H. W. in: *Methods in Enzymology*, K. Mosbach (ed.), 44:134–148, 140, 1976.

Woolley and Mathies, *Proc Natl Acad Sci U S A*, 91:11348–52, 1994.

Wright, A re-determination of the trichromatic coefficients of the spectral colours. *Transactions of the Optical Society, London*, 30:141–164, 1929.

Wu et al., *Genomics*, 4:560, 1989.

Yu and Bruno, Immunomagnetic-electrochemi-luminescent detection of *Escherichia coli* 0157 and *Salmonella typhimurium* in foods and environmental water samples. *Appl. Environ. Microbiol.* 62: 587–92, 1996.

U.S. Pat. No. 3,652,761
U.S. Pat. No. 3,970,518
U.S. Pat. No. 3,933,997
U.S. Pat. No. 4,230,685
U.S. Pat. No. 4,267,234
U.S. Pat. No. 4,677,055
U.S. Pat. No. 4,683,195
U.S. Pat. No. 4,683,202
U.S. Pat. No. 4,695,393
U.S. Pat. No. 4,800,159
U.S. Pat. No. 4,883,750
U.S. Pat. No. 5,003,050

U.S. Pat. No. 5,270,163
U.S. Pat. No. 5,296,375
U.S. Pat. No. 5,304,487
U.S. Pat. No. 5,376,963
U.S. Pat. No. 5,405,766
U.S. Pat. No. 5,424,545
U.S. Pat. No. 5,446,543
U.S. Pat. No. 5,475,096
U.S. Pat. No. 5,539,082
U.S. Pat. No. 5,567,588
U.S. Pat. No. 5,578,832
U.S. Pat. No. 5,580,737
U.S. Pat. No. 5,582,981
U.S. Pat. No. 5,595,877
U.S. Pat. No. 5,610,287
U.S. Pat. No. 5,637,459
U.S. Pat. No. 5,641,629
U.S. Pat. No. 5,645,897
U.S. Pat. No. 5,650,275
U.S. Pat. No. 5,670,637
U.S. Pat. No. 5,683,867
U.S. Pat. No. 5,696,249
U.S. Pat. No. 5,705,629
U.S. Pat. No. 5,707,796
U.S. Pat. No. 5,714,331
U.S. Pat. No. 5,719,262
U.S. Pat. No. 5,736,336
U.S. Pat. No. 5,763,177
U.S. Pat. No. 5,766,855
U.S. Pat. No. 5,773,571
U.S. Pat. No. 5,786,461
U.S. Pat. No. 5,789,157
U.S. Pat. No. 5,817,785
U.S. Pat. No. 5,818,044
U.S. Pat. No. 5,837,832
U.S. Pat. No. 5,837,860
U.S. Pat. No. 5,843,653
U.S. Pat. No. 5,856,108
U.S. Pat. No. 5,856,174
U.S. Pat. No. 5,861,242
U.S. Pat. No. 5,864,026
U.S. Pat. No. 5,867,265
U.S. Pat. No. 5,874,218
U.S. Pat. No. 5,891,625
U.S. Pat. No. 5,904,824
U.S. Pat. No. 5,908,845
U.S. Pat. No. 5,958,691
U.S. Pat. No. 5,972,721
U.S. Pat. No. 5,986,076
U.S. Pat. No. 5,989,823
U.S. Pat. No. 6,001,577
U.S. Pat. No. 6,028,311
U.S. Pat. No. 6,030,776
U.S. Pat. No. 6,043,909
U.S. Pat. No. 6,072,464
GB App. No. 2,202,328
EPO App. No. 266,032
EPO App. No. 320,308
EPO App. No. 329,822
PCT/EP/01219
PCT App. No. US 87/00880
PCT App. No. US 89/01025
PCT App. No. WO 88/10315
PCT App. No. WO 89/06700
PCT App. No. WO 90/07641
PCT App. No. WO 91/19813
PCT App. No. WO 92/20702
PCT App. No. WO 94/05414
PCT App. No. WO 99/31275

---

What is claimed is:

1. A recognition complex comprising a nucleic acid ligand operably coupled to an organic semiconductor.

2. The recognition complex of claim 1, wherein said nucleic acid ligand comprises random DNA sequences.

3. The recognition complex of claim 1, wherein said nucleic acid ligand is between 20 and 100 bases in length.

4. The recognition complex of claim 1, wherein said nucleic acid ligand is between 100 and 300 bases in length.

5. The recognition complex of claim 1, wherein said nucleic acid ligand is operably coupled to said organic semiconductor by electrostatic binding, non-covalent binding or covalent binding.

6. The recognition complex of claim 5, wherein said electrostatic binding is mediated by magnesium ion.

7. The recognition complex of claim 1, wherein said organic semiconductor is diazoluminomelanin (DALM).

8. The recognition complex of claim 1, wherein said organic semiconductor is a polyphenylene.

9. The recognition complex of claim 1, wherein said organic semiconductor produces an electrochemical signal when an analyte is bound to said nucleic acid ligand.

10. The recognition complex of claim 9, wherein said electrochemical signal is a photochemical signal, a fluorescent signal, a luminescent signal, a change of color or a change in electrical conductivity.

11. The recognition complex of claim 1, wherein said nucleic acid ligand is an aptamer.

12. The recognition complex of claim 1, wherein said nucleic acid ligand is selected for its ability to bind to a specific analyte.

13. The recognition complex of claim 1, wherein said nucleic acid ligand is selected for its ability to neutralize a specific analyte.

14. The recognition complex of claim 1, wherein said nucleic acid ligand is produced by amplification of nucleic acids that bind to a specific analyte.

15. A recognition complex system, comprising one or more recognition complexes according to claim 1, operably coupled to a detection unit.

16. The recognition complex system of claim 15, further comprising a data processing unit.

17. The recognition complex system of claim 16, further comprising a sample collector and an isolator.

18. The recognition complex system of claim 15, wherein said detection unit comprises a charge coupled device (CCD), a CCD camera, a photomultiplier tube, a spectrophotometer or a fluorometer.

19. The recognition complex system of claim 15, wherein said recognition complexes are attached to a surface.

20. The recognition complex system of claim 19, wherein said surface comprises a Langmuir-Bodgett film, functionalized glass, germanium, silicon, PTFE, polystyrene, gallium arsenide, gold, silver, membrane, nylon or PVP.

21. The recognition complex system of claim 19, wherein each recognition complex is positioned between a first and a second electrode.

22. The recognition complex system of claim 21, wherein the first electrode is transparent.

23. The recognition complex system of claim 21, further comprising a detection unit that is capable of detecting conductivity changes in each recognition complex.

24. The recognition complex system of claim 16, further comprising system memory for storing the signals produced by each recognition complex for each of a number of known analytes.

25. The recognition complex system of claim 24, wherein the data processing unit is capable of identifying unknown analytes by comparing the signal produced by each recognition complex for the unknown analyte with the stored signals for known analytes.

26. The recognition complex system of claim 16, wherein the data processing unit comprises a neural network or look up tables.

27. The recognition complex system of claim 18, wherein said recognition complexes are attached to magnetic beads.

28. The recognition complex system of claim 27, wherein said organic semiconductor is DALM and said DALM is covalently or non-covalently attached to said magnetic beads.

29. The recognition complex system of claim 28, wherein said nucleic acid ligands are electrostatically attached to said DALM.

30. The recognition complex system of claim 29, wherein said electrostatic attachment is mediated by magnesium ion.

31. The recognition complex system of claim 28, further comprising a data processing unit, a magnetic electrode and a magnetic filter.

32. The recognition complex system of claim 28, further comprising a thermal cycler, a reagent reservoir, a new bead source, a collector and magnetic bead mixer, and one or more pumps.

33. The recognition complex system of claim 16, wherein said recognition complexes are embedded in a matrix.

34. The recognition complex system of claim 33, wherein said matrix is agarose, polyacrylamide or cellulose.

35. A method for identifying an analyte comprising the steps of:

a) generating a recognition complex system comprising one or more recognition complexes each recognition complex comprising a nucleic acid ligand operably coupled to an organic semiconductor;

b) contacting each recognition complex with the analyte;

c) quantifying an electrochemical signal produced by one or more recognition complexes following contact with the analyte, wherein the signal produced by a recognition complex is a function of the affinity the analyte has for the nucleic acid ligand; and d) identifying the analyte based on the signals produced by the one or more recognition complexes.

36. The method of claim 35, further comprising the steps of:

a) transmitting ultraviolet light through each of the recognition complexes after contacting the recognition complexes with the analyte;

b) measuring the electrochemical signals produced by the recognition complexes; and c) generating a unique signature for the analyte based on the signals produced by the recognition complexes.

37. The method of claim 35, wherein the signal is a photochemical signal, a fluorescent signal, a luminescent signal, a change of color or a change in electrical conductivity.

38. A method for producing one or more nucleic acid ligands that bind with high affinity to an analyte comprising the steps of:

a) generating multiple recognition complexes, each recognition complex containing a nucleic acid ligand operably coupled to DALM, wherein each nucleic acid ligand contains a random DNA sequence;

b) contacting the recognition complexes with the analyte;

c) separating those recognition complexes that bind to the analyte from those recognition complexes that do not bind to the analyte;

d) amplifying the nucleic acid ligands from the recognition complexes that bind to the analyte;

e) using the amplified nucleic acid ligands to generate a new set of recognition complexes; and f) repeating steps (b) through (e) until one or more nucleic acid ligands that bind with high affinity to the analyte are produced.

39. The method of claim 38, wherein the recognition complexes are attached to magnetic beads.

40. The method of claim 39, wherein the separating step comprises using a magnetic flow cell, wherein beads attached to recognition complexes that bind to the analyte are separated in the flow cell from beads attached to recognition complexes that do not bind to the analyte.

41. A method for neutralizing an analyte comprising the steps of:

a) producing one or more nucleic acid ligands that bind with high affinity to the analyte;

b) amplifying the one or more nucleic acid ligands;

c) using the amplified nucleic acid ligands to prepare one or more recognition complexes, each recognition complex containing a nucleic acid ligand attached to DALM;

d) contacting the analyte with the recognition complexes under conditions effective to bind the nucleic acid ligand to the analyte; and e) activating the DALM;

wherein activation of the DALM attached to the nucleic acid ligand is effective to neutralize the analyte.

42. The method of claim 41, wherein the activation comprises exposing the DALM to sunlight, heat, laser radiation, ultraviolet radiation, infrared radiation, radiofrequency radiation or microwave radiation.

43. The method of claim 42, wherein said analyte is a biowarfare agent or a chemical warfare agent.

44. The method of claim 43, wherein said analyte is an anthrax spore.

45. The method of claim 35, wherein the analyte is a pharmaceutical, a toxin, a poison, an explosive, a pesticide, a bacterium, a virus, a mold, a yeast, a spore, an algae, an amobae, a dinoflagellate, a unicellualr organism, an allergen, a chemical warfare agent, a biohazardous agent, a protein, a lipid, a carbohydrate, a prion, a radiosotope, a vitamin, a heterocyclic aromatic compound, a carcinogen, a mutagen, a narcotic, an amphetamine, a barbiturate, a hallucinogen, a waste product or a contaminant.

46. The method of claim 35, further comprising detecting explosives or illegal drugs in an airport detection system.

47. The method of claim 35, further comprising detecting air-borne pathogens in an air conditioner monitoring system.

48. The method of claim 35, further comprising detecting water-borne pathogens, carcinogens, teratogens or toxins in a water quality monitoring system.

49. The method of claim 35, further comprising detecting pathogens in an operating room monitoring system.

50. The method of claim 35, further comprising detecting allergens, pathogens or contaminants in an food production monitoring system.

51. The method of claim 35, further comprising detecting genetically modified organisms.

52. The method of claim 35, further comprising performing high through-put screening for pharmaceutical compounds.

53. The method of claim 52, wherein said recognition complex comprises a nucleic acid ligand that is selected to bind specifically to a known agonist or antagonist of an enzyme, receptor protein, transport protein, cytokine, transcription factor, protein kinase or structural protein.

54. The method of claim 53, further comprising screening a library of small molecule drug candidates, wherein binding of said candidate to said nucleic acid ligand indicates an affinity of said candidate for said enzyme, receptor protein, transport protein, cytokine, transcription factor, protein kinase or structural protein.

55. The recognition complex system of claim 19, wherein said surface is part of a card or badge.

56. The recognition complex system of claim 55, wherein binding of an analyte to one or more recognition complexes is detectable as a change in color.

57. The recognition complex system of claim 55, wherein binding of an analyte to one or more recognition complexes is detectable as an electrical signal.

58. The recognition complex system of claim 57, wherein said electrical signal activates an alarm.

59. The recognition complex system of claim 58, wherein said alarm is transmitted to a remote location.

60. The recognition complex system of claim 55, wherein said nucleic acid ligands are selected to bind specifically to a biowarfare agent or a chemical warfare agent.

61. The recognition complex system of claim 60, wherein said biowarfare agent is an anthrax spore.

62. The method of claim 35, further comprising performing high through-put screening for pharmaceutical compounds.

* * * * *

SEQUENCE LISTING

<160> NUMBER OF SEQ ID NOS: 4

<210> SEQ ID NO 1
<211> LENGTH: 30
<212> TYPE: DNA
<213> ORGANISM: Hordeum vulgare

<400> SEQUENCE: 1
acaactccga caactcggtg cacggtgggt                30

<210> SEQ ID NO 2
<211> LENGTH: 30
<212> TYPE: DNA
<213> ORGANISM: Hordeum vulgare

<400> SEQUENCE: 2
ggcagctcca tgctacctat gagtaggtac                30

<210> SEQ ID NO 3
<211> LENGTH: 30
<212> TYPE: DNA
<213> ORGANISM: Bacillus anthracis

<400> SEQUENCE: 3
atcaccagag gcaagacacc cccttgtggc                30

-continued

```
<210> SEQ ID NO 4
<211> LENGTH: 30
<212> TYPE: DNA
<213> ORGANISM: Bacillus anthracis

<400> SEQUENCE: 4
gtcaactgat tcttgatatt ttgagatgtt                                  30
```